(12) United States Patent
King et al.

(10) Patent No.: US 12,378,304 B2
(45) Date of Patent: Aug. 5, 2025

(54) THERAPEUTIC POLYPEPTIDE

(71) Applicants: Paul Thomas King, Glen Iris (AU); Ashley Maurice Buckle, Richmond (AU)

(72) Inventors: Paul Thomas King, Glen Iris (AU); Ashley Maurice Buckle, Richmond (AU)

( * ) Notice: Subject to any disclaimer, the term of this patent is extended or adjusted under 35 U.S.C. 154(b) by 0 days.

(21) Appl. No.: 18/903,864

(22) Filed: Oct. 1, 2024

(65) Prior Publication Data
US 2025/0092119 A1    Mar. 20, 2025

Related U.S. Application Data

(63) Continuation of application No. PCT/AU2024/050430, filed on May 3, 2024.

(30) Foreign Application Priority Data

May 5, 2023   (AU) ............................... 2023901357

(51) Int. Cl.
| C07K 14/81 | (2006.01) |
| A61K 38/00 | (2006.01) |
| C12N 15/70 | (2006.01) |

(52) U.S. Cl.
CPC .......... C07K 14/8125 (2013.01); C12N 15/70 (2013.01); *A61K 38/00* (2013.01)

(58) Field of Classification Search
CPC ..... C07K 14/8125; C12N 15/70; A61K 38/00
See application file for complete search history.

(56) References Cited

U.S. PATENT DOCUMENTS

2015/0104410 A1* 4/2015 Eckelman .......... C07K 14/8121
                                                          424/134.1

FOREIGN PATENT DOCUMENTS

| WO | WO 1994/026781 A1 | 11/1994 | |
| WO | WO 2009/066807 A1 | 5/2009 | |
| WO | WO-2016069574 A1 * | 5/2016 | ............. A61K 38/55 |
| WO | WO 2019/148848 A1 | 8/2019 | |
| WO | WO-2020092448 A1 * | 5/2020 | ............. A61K 38/00 |
| WO | WO 2020/152653 A1 | 7/2020 | |

OTHER PUBLICATIONS

Scott et al., 2020, Engineering the serpin alpha1-antitrypsin: A diversity of goals and techniques, Protein Science, 29: 856-871.*
Sosulski et al., 2020, Gene therapy for alpha 1-antitrypsin deficiency with an oxidant-resistant human alpha 1-antitrypsin, JCI Insight, 5(1): e135951 (16 pages).*
Lior et al., 2018, Point Mutation of a Non-Elastase-Binding Site in Human alpha1-Antitrypsin Alters Its Anti-Inflammatory Properties, Frontiers in Immunology, 9: 759 (12 pages).*
Taggart et al., 2000, Oxidation of either Methionine 351 or Methionine 358 in alpha1-Antitrypsin Causes Loss of Anti-neutrophil Elastase Activity, The Journal of Biological Chemistry, 275(35): 27258-27265.*
Hamada et al., 2021, Stepwise Reversion of Multiply Mutated Recombinant Antitrypsin Reveals a Selective Inhibitor of Coagulation Factor Xia as Active as the M358R Variant, Frontiers in Cardiovascular Medicine, 8: 647405 (12 pages).*
Vidaud et al., 1992, Met 358 to Arg Mutation of Alpha1-Antitrypsin Associated with Protein C deficiency in a Patient with Mild Bleeding Tendency, J Clin Invest, 89: 1537-1543.*
Basak, 2004, Inhibitors of proprotein convertases, J Mol Med, 83: 844-855.*
Bachman, "Site-directed mutagenesis," (2013) Ch. 19, Methods in Enzymology, 1st ed. Elsevier Inc 529:241-248.
Bai et al., "Hypothesis: Alpha-1-antitrypsin is a promising treatment option for COVID-19," (2021) Medical Hypotheses 146:110394 (8 pages).
Cabrita et al., "A family of *E. coli* expression vectors for laboratory scale and high throughput soluble protein production," (2006) BMC Biotechnology 6(12):1-8.
Dousha et al., "Assessing Respiratory Immune Responses to Haemophilus Influenzae," (2021) J Vis Exp.
Dunvanloo et al., "Cloning and expression of the gene for bacteriophage T7 RNA polymerase," (1984) Proc Natl Acad Sci 81(7):2035-2039.
Gottesman et al., "Role of sulA and sulB in Filamentation by Lon Mutants of *Escherichia coli* K-12," (1981) Journal of Bacteriology 148(1):265-273.
Grant et al., "Differential plasmid rescue from transgenic mouse DNAs into *Escherichia coli* methylation-restriction mutants," (1990) 87(12):4645-4649.
Greenfield, "Using circular dichroism collected as a function of temperature to determine the thermodynamics of protein unfolding and binding interactions," (2009) Nat Protoc 1(6):2527-2535.
Horvath et al., "Methods to measure the kinetics of protease inhibition by serpins," (2011) Ch. 11, Methods Enzymology 1st ed. Elsevier Inc 501:223-235.
Janciauskiene et al., "The Multifaceted Effects of Alpha1-Antitrypsin on Neutrophil Functions," (2018) Front Pharmacol 9(341):1-13.
Jha et al., "Single amino acid substitutions in recombinant plant-derived human α1-proteinase inhibitor confer enhanced stability and functional efficacy," (2014) Biochimica et Biophysica Acta 1840:416-427.
John et al., "Van't Hoff enthalpies without baselines," (2000) Protein Science 9(7):1416-1419.
King et al., "Deoxyribonuclease 1 reduces pathogenic effects of cigarette smoke exposure in the lung," (2017) Sci Rep 7(12128):2-9.

(Continued)

*Primary Examiner* — Amber D Steele
(74) *Attorney, Agent, or Firm* — Haynes and Boone LLP

(57) ABSTRACT

This disclosure provides an alpha-1 antitrypsin (AAT) polypeptide as defined herein. Also provided herein are pharmaceutical compositions comprising the polypeptide, nucleic acids encoding the polypeptide, vectors comprising the nucleic acid, cells, and methods of producing the AAT polypeptide and method of using the AAT polypeptide in therapy.

18 Claims, 21 Drawing Sheets
Specification includes a Sequence Listing.

(56) References Cited

OTHER PUBLICATIONS

King et al., "Nontypeable Haemophilus influenzae induces sustained lung oxidative stress and protease expression," (2015) PLoS One 10(3):e012037 (pp. 1-17).
King et al., "Phagocyte extracellular traps in children with neutrophilic airway inflammation," (2021) ERJ Open Res 7(2) (10 pages).
Kwon et al., "Refolding of alpha 1-antitrypsin expressed as inclusion bodies in *Escherichia coli*: characterization of aggregation," (1995) Biochim Biophys Acta 12479179-84.
Levina et al., "Expression, purification and characterization of recombinant Z α1-Antitrypsin—The most common cause of α1-Antitrypsin deficiency," (2009) Protein Expr Purif 68(2):226-232.
Matthews et al., "Enhanced protein thermostability from site-directed mutations that decrease the entropy of unfolding," (1987) Proc Natl Acad Sci 84:6663-6667.
Pearce et al., "Production of Recombinant Serpins in *Escherichia coli*," (2011) Methods in Enzymology 1st ed., Elsevier Inc 501:13-28.
Seo et al., "Concerted regulation of inhibitory activity of α1-antitrypsin by the native strain distributed throughout the molecule," (2002) J Biol Chem 277(16):14216-14220.
Studier et al., "Use of Bacteriophage T7 RNA Polymerase to Direct Selective High-level Expression of Cloned Genes," (1986) Journal of Molecular Biology 189(1):113-130.

* cited by examiner

Figure 1

SEQ ID NO: 1
Human AAT

```
                                                            50
MPSSVSWGIL LLAGLCCLVP VSLAEDPQGD AAQKTDTSHH DQDHPTFNKI TPNLAEFAFS
                                       100
LYRQLAHQSN STNIFFSPVS IATAFAMLSL GTKADTHDEI LEGLNFNLTE IPEAQIHEGF
                            150
QELLRTLNQP DSQLQLTTGN GLFLSEGLKL VDKFLEDVKK LYHSEAFTVN FGDTEEAKKQ
                 200
INDYVEKGTQ GKIVDLVKEL DRDTVFALVN YIFFKGKWER PFEVKDTEEE DFHVDQVTTV
       250                                                 300
KVPMMKRLGM FNIQHCKKLS SWVLLMKYLG NATAIFFLPD EGKLQHLENE LTHDIITKFL
                                       350
ENEDRRSASL HLPKLSITGT YDLKSVLGQL GITKVFSNGA DLSGVTEEAP LKLSKAVHKA
                            400                           418
VLTIDEKGTE AAGAMFLEAI PMSIPPEVKF NKPFVFLMIE QNTKSPLFMG KVVNPTQK
```

SEQ ID NO: 2
Part-Sequence of AAT

```
                                                            50
DQDHPTFNKI TPNLAEFAFS LYRQLAHQSN STNIFFSPVS IATAFAMLSL GTKADTHDEI
                                       100
LEGLNFNLTE IPEAQIHEGF QELLRTLNQP DSQLQLTTGN GLFLSEGLKL VDKFLEDVKK
                            150
LYHSEAFTVN FGDTEEAKKQ INDYVEKGTQ GKIVDLVKEL DRDTVFALVN YIFFKGKWER
                 200
PFEVKDTEEE DFHVDQVTTV KVPMMKRLGM FNIQHCKKLS SWVLLMKYLG NATAIFFLPD
       250                                                 300
EGKLQHLENE LTHDIITKFL ENEDRRSASL HLPKLSITGT YDLKSVLGQL GITKVFSNGA
                                       350
DLSGVTEEAP LKLSKAVHKA VLTIDEKGTE AAGAMFLEAI PMSIPPEVKF NKPFVFLMIE
                 378
QNTKSPLFMG KVVNPTQK
```

Figure 1 Continued

SEQ ID NO: 3
sAAT (produced in *E. Coli* expression system)

```
                                                            50
MENLYFQGAA SDQDHPTFNK ITPNLAEFAF SLYRQLAHQS NSTNIFFSPV SIATAFAMLS
                                                           100
LGTKADTHDE ILEGLNFNLT EIPEAQIHEG FQELLRTLNQ PDSQLQLTTA NGLFLSEGLK
                                                           150
LVDKFLEDVK KLYHSEAFTV NFGDTEEAKK QINDWVEKGT QGKIVDLVKE LDRDTVFALV
                                                           200
NAIFFKGKWE RPFEVKDTEE EDFHVDQVTT VKVPMMKRLG MFNIQHCKKL SSWVLLMKYL
           250                                             300
GNATAIFFLP DEGKLQHLEN ELTHDIITKF LENEDRRSAS LHLPKFKIEG TYDLKSVLGQ
                                                           350
LGITKVFSNG ADLSGVTEEA PLKLSKAVHK AVLEVNEEGT EAAGAMFLEA IPMSIPPEVK
                                 389
FNKPFVFLII EQNTKSPLFM GKVVNPTQK
```

SEQ ID NO: 4
sAAT (produced in CHO expression system)

```
                                                            50
MPSSVSWGIL LLAGLCCLVP VSLAEDPQGD AAQKTDTSHH DQDHPTFNKI TPNLAEFAFS
                                                           100
LYRQLAHQSN STNIFFSPVS IATAFAMLSL GTKADTHDEI LEGLNFNLTE IPEAQIHEGF
                                                           150
QELLRTLNQP DSQLQLTTAN GLFLSEGLKL VDKFLEDVKK LYHSEAFTVN FGDTEEAKKQ
                                                           200
INDWVEKGTQ GKIVDLVKEL DRDTVFALVN AIFFKGKWER PFEVKDTEEE DFHVDQVTTV
           250                                             300
KVPMMKRLGM FNIQHCKKLS SWVLLMKYLG NATAIFFLPD EGKLQHLENE LTHDIITKFL
                                                           350
ENEDRRSASL HLPKFKIEGT YDLKSVLGQL GITKVFSNGA DLSGVTEEAP LKLSKAVHKA
                                            400                418
VLEVNEEGTE AAGAMFLEAI PMSIPPEVKF NKPFVFLIIE QNTKSPLFMG KVVNPTQK
```

Figure 1 Continued

SEQ ID NO: 5
uAAT (produced in *E. Coli* expression system)

```
                                                              50
MENLYFQGAA SDQDHPTFNK ITPNLAEFAF SLYRQLAHQS NSTNILFSPV SIAAAFAMLS
                                         100
LGAKGDTHDE ILEGLNFNLT EIPEAQIHEG FQELLRTLNQ PDSQLQLTTA NGLFLSEGLK
                       150
LVDKFLEDVK KLYHSEAFTV NFGDTEEAKK QINDWVEKGT QGKIVDLVKE LDRDTVFALV
             200
NAIFFKGKWE RPFEVKDTEE EDFHVDQVTT VKVPMMKRLG MFNIQHCKKL SSWVLLMKYL
  250                                                         300
GNATAIFFLP DEGKLQHLEN ELTHDIITKF LENEDRRSAS LHLPKFKIEG TYDLKSVLGQ
                                            350
LGITKVFSNG ADLSGVTEEA PLKLSKAVHK AVLEVNEEGT EAAGAMFLEA IPMSIPPEVK
                             389
FNKPFVFLII EQNTKAPLFM GRVVNPTQK
```

SEQ ID NO: 6
uAAT (produced in CHO expression system)

```
                                                              50
MPSSVSWGIL LLAGLCCLVP VSLAEDPQGD AAQKTDTSHH DQDHPTFNKI TPNLAEFAFS
                                         100
LYRQLAHQSN STNILFSPVS IAAAFAMLSL GAKGDTHDEI LEGLNFNLTE IPEAQIHEGF
                       150
QELLRTLNQP DSQLQLTTAN GLFLSEGLKL VDKFLEDVKK LYHSEAFTVN FGDTEEAKKQ
             200
INDWVEKGTQ GKIVDLVKEL DRDTVFALVN AIFFKGKWER PFEVKDTEEE DFHVDQVTTV
  250                                                         300
KVPMMKRLGM FNIQHCKKLS SWVLLMKYLG NATAIFFLPD EGKLQHLENE LTHDIITKFL
                                            350
ENEDRRSASL HLPKFKIEGT YDLKSVLGQL GITKVFSNGA DLSGVTEEAP LKLSKAVHKA
                                          400                418
VLEVNEEGTE AAGAMFLEAI PMSIPPEVKF NKPFVFLIIE QNTKAPLFMG RVVNPTQK
```

Figure 1 Continued

SEQ ID NO: 7

N-terminal *E. coli* sequence in uAAT and sAAT

```
          11
MENLYFQGAA S
```

SEQ ID NO: 8

N-terminal sequence in humans and CHO-expressed uAAT and sAAT

```
                                40
MPSSVSWGIL LLAGLCCLVP VSLAEDPQGD AAQKTDTSHH
```

SEQ ID NO: 9

N-terminal sequence

```
          25
MPSSVSWGIL LLAGLCCLVP VSLAE
```

A) Control
B) IAV
C) IAV and sAAT
D) IAV
E) IAV and sAAT
F) Control

A)

B)

THERAPEUTIC POLYPEPTIDE

CROSS REFERENCE TO RELATED APPLICATIONS

This application is a bypass continuation of International Application No. PCT/AU2024/050430, filed May 3, 2024, which claims priority benefit of the foreign filing date of AU Patent Application No. 2023901357, filed May 5, 2023, the disclosures of which are herein incorporated by reference in their entireties.

SEQUENCE LISTING

The instant application contains a Sequence Listing which has been submitted electronically in XML format and is hereby incorporated by reference in its entirety. Said XML copy, created on Sep. 30, 2024, is named GRF-0001-C1-US ST26 SL.xml and is 19 kilobytes in size.

FIELD

The present disclosure relates to an alpha-1 anti-trypsin (AAT) polypeptide. The disclosure also relates to pharmaceutical compositions comprising the polypeptide, nucleic acids encoding the polypeptide, vectors comprising the nucleic acid, cells, and methods of producing the AAT polypeptide and methods of using the AAT polypeptide in therapy.

BACKGROUND

The lung is constantly exposed to a variety of infectious and environmental substances, which are potentially damaging to the lung. This induces an immune response with associated inflammation. This inflammatory response is protective against these threats, but if excessive may contribute to lung damage and clinical disease; some important examples of this include chronic obstructive pulmonary disease (COPD)/emphysema, cystic fibrosis (CF), pulmonary fibrosis, air pollution (responsible for about 9 million deaths per year) and a variety of infections such as bacterial (e.g., *Haemophilus influenzae*) and viral (e.g., influenza).

The inflammatory/immune response in the lung is complex but a key pathway is the production of proteases such as neutrophil elastase (NE). Excessive production of proteases and/or a deficiency of inhibitors results in protease imbalance and lung damage. This protease imbalance is also relevant to other inflammatory conditions elsewhere in the body such as sepsis and also to certain cancers (e.g., lung cancer).

An important mechanism of protease expression in the lung is the formation of extracellular traps. Extracellular traps are expressed by phagocytes such as neutrophils (NETs) and also by other cells such as macrophages (METs) and are antimicrobial. Traps are comprised of extracellular chromatin (DNA) and co-expressed mediators such as NE. NETs have an important role in activating the inflammatory response to clear such infections. However, components of traps such as proteases may be damaging to host tissues. Recent studies suggest that NETs can cause significant tissue damage in other inflammatory diseases.

One of the key anti-proteases produced in the body is the serpin alpha-1 antitrypsin (AAT). AAT inactivates serine proteases such as NE and trypsin (and also downregulates other proteases such as metalloproteinase 9).

Whilst AAT acts against proteases, it also has broader anti-inflammatory effects which are not fully understood or well categorized. These effects include reducing the effect of cytokines such as interleukin 8 (IL8) and tumour necrosis factor, inflammatory intracellular signalling pathways and apoptosis. With its effect on NE and IL8 and signalling pathways AAT has particular effects to downregulate inflammation driven by neutrophils. In contrast to other cellular pathways such as those driven by eosinophils there are minimal biologic-based therapies which specifically target the effect of neutrophils.

AAT also has direct anti-viral effects by interfering with host proteases which viruses such as influenza and coronavirus use to infect respiratory epithelium. As such AAT is not only an anti-inflammatory agent but also could be considered to be an antiviral for some infections.

AAT is one of the most prevalent proteins in human serum/plasma and blood-derived AAT has been used for many years in the United States (and other countries) as a chronic replacement therapy for patients with congenital deficiency and clinical manifestations such as emphysema. In this context it has been shown to be very safe and well tolerated. AAT is approved for use in patients by the Therapeutic Goods Administration of. AAT is not used as an anti-inflammatory agent.

Whilst AAT as a therapy has great potential for a variety of prevalent medical conditions it is rarely used. Significant issues that restrict its usage are that as it is derived from blood donors, the availability is strictly limited and it is very expensive (cost about $100,000 per year in Australia). It is also very heterogeneous and unstable.

Not all proteins fold into the most thermodynamically stable conformation, instead they pause folding once reaching a particular intermediate. AAT folds into a metastable native conformation, and uses this metastability to drive its function, which involves undergoing an irreversible, but thermodynamically favourable structural transition to the more stable, cleaved state (known as the S-to-R transition). Due to the inherent metastability of the native, functional state, AAT is susceptible to misfolding and aggregation under various conditions, including heat and the presence of mutations. Therefore, increasing the stability of the metastable native state (both thermodynamically and kinetically) could prevent misfolding and aggregation, all while not affecting its inhibitory function. Improving AAT protein stability is important for the development of novel AAT therapies, as protein stability is an important factor for AAT therapies particularly with administration routes requiring aerosol delivery.

AAT is a therapy (in addition to the established indication of replacement treatment in patients with congenital deficiency) that has a vast array of inflammatory lung (e.g., COPD, CF, pulmonary fibrosis, air pollution and infections such as influenza and *Haemophilus influenzae*) and extra-pulmonary conditions in which it may be beneficial, but is currently unavailable. It would be desirable to develop a recombinant form of AAT that could be used for one or more of these conditions. Further, it would be desirable to understand the effects of different mutations on AATs metastability. It would further be desirable to provide engineered AATs having improved stability and folding properties that are useful in therapy, which are relatively homogenous and/or which can be manufactured commercially in adaquate quantities at a competitive cost.

SUMMARY

In one aspect, there is provided an alpha-1 antitrypsin (AAT) polypeptide, comprising: an amino acid sequence having at least 90% sequence identity to SEQ ID NO: 2; wherein the amino acid sequence differs from SEQ ID NO: 2 in that it includes 3 or more amino acid substitutions from SEQ ID NO: 2 which are independently selected from the group consisting of G99A, Y144W, Y171A, L275F, S276K, T278E, T323E, I324V, D325N, K327E, and M358I.

In some embodiments, the amino acid sequence has one, two or all of the following groups of amino acid substitutions from SEQ ID NO: 2:
S276K, T278E, T323E, D325N and K327E;
L275F, I324V and M358I; and
G99A, Y144W and Y171A.

In some embodiments, the amino acid sequence has 5 or more, or 6 or more, or 8 or more amino acid substitutions from SEQ ID NO: 2 which are independently selected from the group consisting of G99A, Y144W, Y171A, L275F, S276K, T278E, T323E, I324V, D325N, K327E, and M358I.

In some embodiments, the amino acid sequence includes each of the following amino acid substitutions from SEQ ID NO: 2: G99A, Y144W, Y171A, L275F, S276K, T278E, T323E, I324V, D325N, K327E, and M358I.

In some embodiments, the amino acid sequence includes 1 or more further amino acid substitutions from SEQ ID NO: 2 which are independently selected from the group consisting of F35L, T43A, T52A, A54G, S365A, and K371R.

In some embodiments, the amino acid sequence includes 2 or more, or 3 or more, or 4 or more, or 5 or more, or each of the following further amino acid substitutions from SEQ ID NO: 2: F35L, T43A, T52A, A54G, S365A, and K371R.

In some embodiments, the amino acid sequence has at least 91%, at least 92%, at least 93%, at least 94% or at least 95% sequence identity to SEQ ID NO: 2.

In some embodiments, the amino acid sequence has not more than 35, not more than 30, not more than 25, not more than 20 amino acid modifications from SEQ ID NO:2.

In some embodiments, the amino acid sequence has not more than 10, not more than 5, or no amino acid modifications from SEQ ID NO: 2, other than:
including 3 or more amino acid substitutions from SEQ ID NO: 2 which are independently selected from the group consisting of G99A, Y144W, Y171A, L275F, S276K, T278E, T323E, I324V, D325N, K327E, and M358I; and
optionally including 1 or more further amino acid substitutions from SEQ ID NO: 2 which are independently selected from the group consisting of F35L, T43A, T52A, A54G, S365A, and K371R.

In some embodiments, the polypeptide comprises additional N-terminal and/or C-terminal amino acid sequence.

In some embodiments, prior to the amino acid sequence, the AAT polypeptide comprises the N-terminal sequence MENLYFQGAAS (SEQ ID NO: 7) or MPSSVSWGILLLAGLCCLVPVSLAEDPQGDAAQKTDTSHH (SEQ ID NO: 8).

In some embodiments, the AAT polypeptide has the amino acid sequence of SEQ ID NO: 3, SEQ ID NO: 4, SEQ ID NO: 5 or SEQ ID NO: 6.

In some embodiments, the AAT polypeptide has improved thermal stability compared to wild-type human AAT.

In some embodiments, the AAT polypeptide has improved re-fold yield compared to wild-type AAT.

In some embodiments, the AAT polypeptide comprises a modification selected from the group consisting of glycosylation, PEGylation, prenylation, acylation, a biotinylation, phosphorylation, and conjugation to a lipid moiety.

In another aspect, there is provided a nucleic acid molecule encoding the AAT polypeptide as defined herein.

In another aspect, there is provided a vector comprising a nucleic acid sequence encoding the AAT polypeptide as defined herein.

In some embodiments, the nucleic acid sequence is linked to an expression control sequence suitable for expression in a host cell.

In another aspect, there is provided a cell comprising a nucleic acid as defined herein.

In some embodiments, the cell comprises a vector as defined herein.

In some embodiments, the cell is a mammalian cell or a bacterial cell.

In some embodiments, the cell is a DH5α, BL21 (DE3) pLysS, SG13009 or Rosetta Blue DE3 cell.

In another aspect, there is provided a method of producing an AAT polypeptide as defined herein, comprising:
a. transfecting a host cell with a nucleic acid sequence encoding the AAT polypeptide as defined herein;
b. culturing the transfected host cell in a cell culture media and expressing the AAT polypeptide, and
c. recovering the AAT polypeptide from the cell culture media.

In another aspect, there is provided a pharmaceutical composition comprising: the AAT polypeptide as defined herein; and a pharmaceutically acceptable excipient.

In some embodiments, the pharmaceutical composition retains at least 80%, or at least 90%, or at least 95% of its initial neutrophil elastase inhibitory activity upon storage at 4° C. for a period of 3 months, or for a period of 6 months.

In another aspect, there is provided an AAT polypeptide as defined herein, or a pharmaceutical composition as defined herein, for use as a medicament.

In some embodiments, the AAT polypeptide or pharmaceutical composition is for use in preventing or treating AAT deficiency, or a disease or disorder associated with AAT deficiency.

In some embodiments, the AAT polypeptide or pharmaceutical composition is for use in treating or preventing an inflammatory disease, a respiratory disease, a cancer and/or a viral infection.

In some embodiments, the inflammatory disease, respiratory disease and/or viral infection is selected from the group consisting of: sepsis, autoimmune disease (e.g. inflammatory arthritis, vasculitis), acute respiratory disease, emphysema, pulmonary fibrosis, chronic obstructive pulmonary disease, asthma, emphysema, a respiratory disease associated with air pollution, a cancer associated with protease activity (e.g. lung cancer), influenza A virus (IAV) and highly pathogenic avian influenza (HPAI).

In another aspect, there is provided a method of preventing or treating AAT deficiency, or a disease or disorder associated with AAT deficiency, in a subject, comprising administering an effective amount of an AAT polypeptide as defined herein, or a pharmaceutical composition as defined herein, to the subject.

In some embodiments, the method is for treating or preventing an inflammatory disease, a respiratory disease, a cancer and/or a viral infection.

In some embodiments, the inflammatory disease, respiratory disease and/or viral infection is selected from the group consisting of: sepsis, autoimmune disease (e.g. inflammatory arthritis, vasculitis), acute respiratory disease, emphysema, pulmonary fibrosis, chronic obstructive pulmonary disease, asthma, emphysema, a respiratory disease associated with air pollution, a cancer associated with protease activity (e.g. lung cancer), influenza A virus (IAV) and highly pathogenic avian influenza (HPAI).

In another aspect, there is provided use of an AAT polypeptide as defined herein, for the manufacture of a medicament for preventing or treating AAT deficiency, or a disease or disorder associated with AAT deficiency.

In some embodiments, the medicament is for treating or preventing an inflammatory disease, a respiratory disease, a cancer and/or a viral infection.

In some embodiments, the inflammatory disease, respiratory disease and/or viral infection is selected from the group consisting of: sepsis, autoimmune disease (e.g. inflammatory arthritis, vasculitis), acute respiratory disease, emphysema, pulmonary fibrosis, chronic obstructive pulmonary disease, asthma, emphysema, a respiratory disease associated with air pollution, a cancer associated with protease activity (e.g. lung cancer), influenza A virus (IAV) and highly pathogenic avian influenza (HPAI).

In some embodiments, the method, use, or AAT polypeptide or pharmaceutical composition for use, achieves one or more of the following: reduced cytokine levels in a subject, reduced formation of extracellular traps in an organ of a subject, reduced protease activity, and reduced leukocyte infiltrate in an organ of a subject.

In some embodiments, the disease or disorder is an inflammatory disease or disorder, and is a neutrophil-associated inflammatory disease or disorder.

In some embodiments, the method, use or AAT polypeptide or pharmaceutical composition for use involves administration of the AAT polypeptid or pharmaceutical composition in combination with a further therapeutic agent.

BRIEF DESCRIPTION OF THE DRAWINGS

FIG. 1 shows sequence information relevant to the present disclosure.

Amino acid sequence for wildtype human AAT (wtAAT) is shown in SEQ ID NO: 1.

Amino acid sequence for the section of wtAAT sequence upon which the AAT polypeptides of the present disclosure is based, is shown in SEQ ID NO: 2.

Amino acid sequence for an exemplary AAT polypeptide, sAAT, is shown in SEQ ID NO: 3. Differences from the corresponding sequence of wtAAT are illustrated in bold. The sequence has an *E. coli* N-terminus tag.

Amino acid sequence for an exemplary AAT polypeptide, sAAT, is shown in SEQ ID NO: 4. Differences from the corresponding sequence of wtAAT are illustrated in bold. The sequence has a CHO N-terminus tag.

Amino acid sequence for a further exemplary AAT polypeptide, uAAT, are shown in SEQ ID NO: 5. Differences with wtAAT are illustrated in bold. The sequence has an *E. coli* N-terminus tag.

Amino acid sequence for a further exemplary AAT polypeptide, uAAT, is shown in SEQ ID NO: 6. Differences from the corresponding sequence of wtAAT are illustrated in bold. The sequence has a CHO N-terminus tag.

Amino acid sequence for the N-terminal *E. coli* sequence used in two exemplary AAT polypeptides of the present disclosure, sAAT and uAAT, is shown in SEQ ID NO: 7.

Amino acid sequence for the N-terminal sequence of wild type human AAT, and N-terminal sequence used in two exemplary AAT polypeptides of the present disclosure, sAAT and uAAT, produced in a CHO expression system, is shown in SEQ ID NO: 8.

Amino acid sequence for additional N-terminal sequence used in embodiments of the present disclosure is shown in SEQ ID NO: 9.

Figure 2:
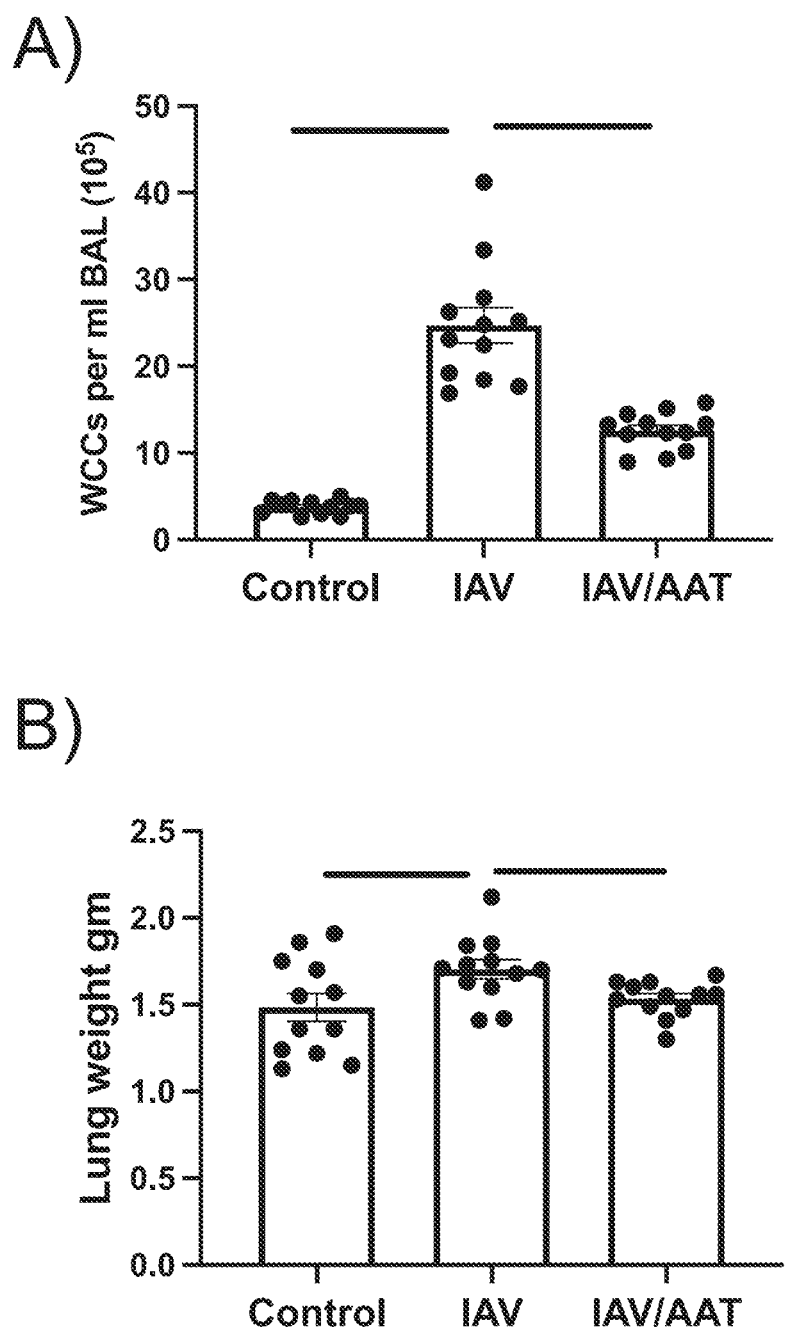

FIG. 2 shows the results of in vitro and in vivo models using nebulised wtAAT which demonstrate that it has potent anti-inflammatory effects. FIG. 2A shows the effect of administration of wtAAT on white cell count (WCC), FIG. 2B shows the effect of administration of wtAAT on lung weight.

Figure 3A:
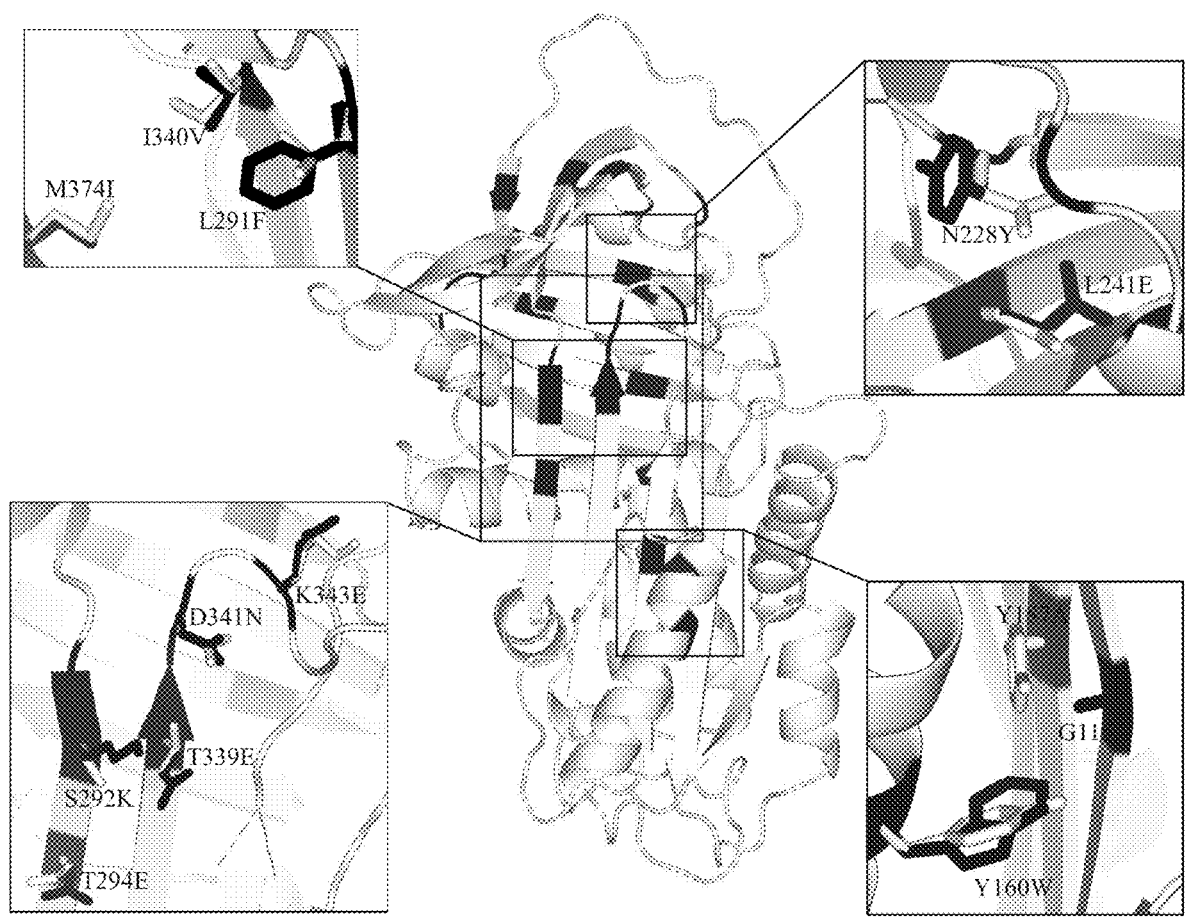

FIG. 3A is an illustration showing the front view of regions grafted onto wtAAT (PDB ID: 3NE4). Each region grafted onto wtAAT contributes to biophysical properties, such as improved thermostability and/or kinetic stability and/or reduced aggregation propensity, and/or to improved colloidal properties through various favourable interactions. Mutated residues are shown as sticks (wtAAT=white, mutated residue=black). Top Left: F51: Improved packing against β-sheet A; Top Right: Citrate-binding: Stabilises the native state; Bottom Left: Breach: Increased salt bridges improving stability; Bottom Right: Helix-F Improved packing, add rigidity.

Figure 3B:

FIG. 3B is an illustration showing the back view of which regions grafted onto wtAAT (PDB ID: 3NE4). Each region grafted onto wtAAT is hypothesized to contribute to ideal biophysical properties through various favourable interactions. Mutated residues are shown as sticks (wtAAT=white, mutated residue=black). Top Left: β-Sheet C stapling: Additional salt bridge, stabilising sheet; Top Right: Helix-H: Improve packing, addition salt bridge for further stabilisation; Bottom Left: T59: Favourable polar and non-polar interactions; Bottom Right: B/C barrel: Improve hydrophobic packing.

Figure 4:
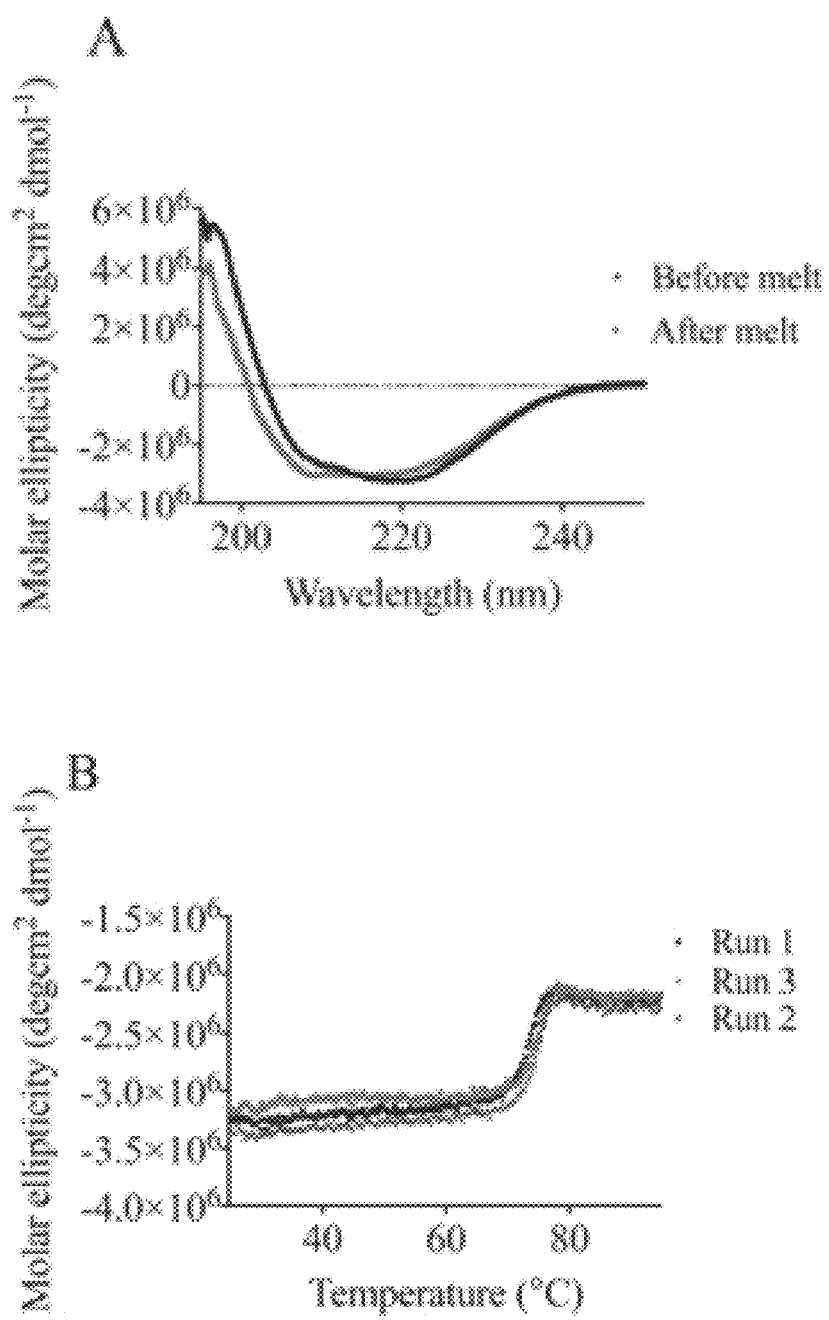
Figure 4:
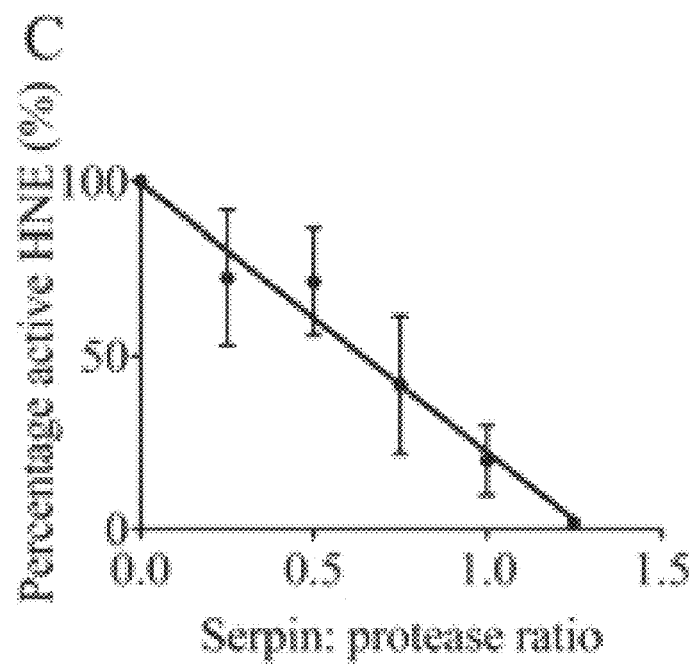
Figure 4:
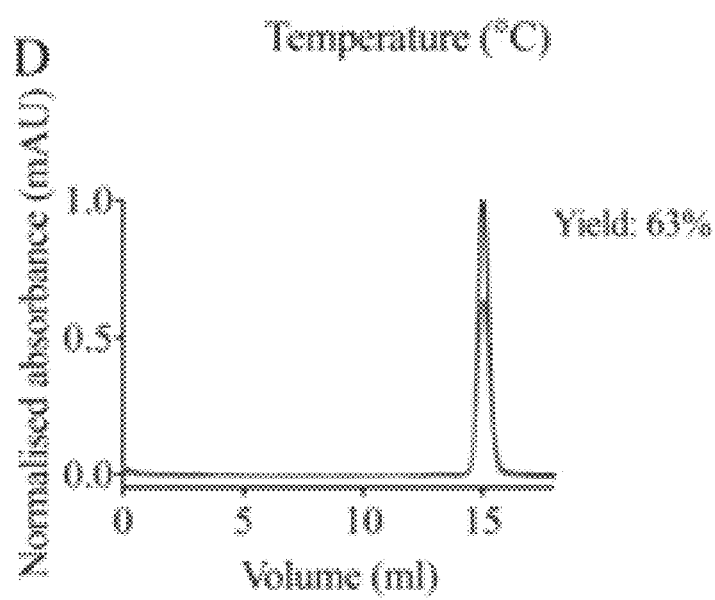
Figure 4:
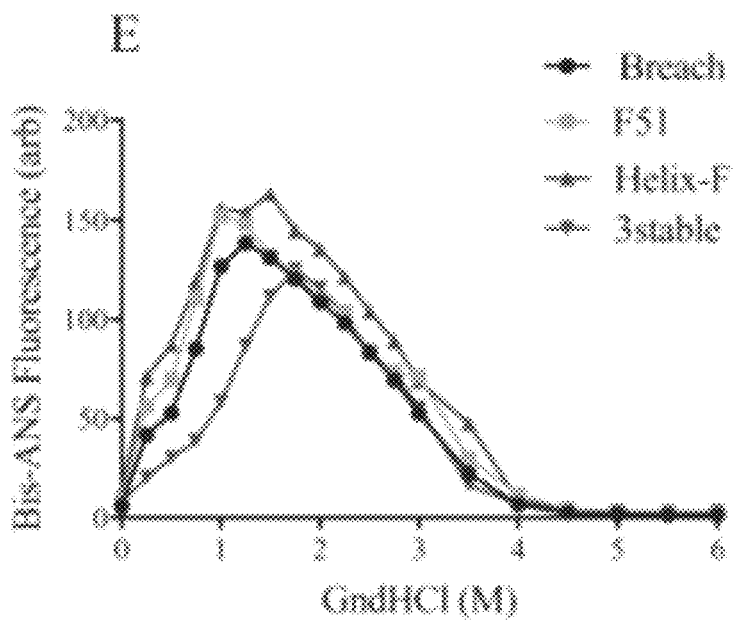

FIG. 4 illustrates the results of biophysical analysis of an AAT polypeptide according to the present disclosure, sAAT, which was produced in a CHO expression system. A. Spectral scans before and after thermal denaturation indicate structural changes post melt. B. Thermal denaturation curve of each triplicate, producing a midpoint of melting (Tm) of 73.4° C. C. Inhibitory activity against HNE indicates the sAAT graft is active against HNE. D. The yield of monomeric protein is higher than wtAAT and each of the individual thermal stable grafts. E. Extrinsic fluorescence show a folding intermediate becoming populated at a higher denaturation concentration for the sAAT graft.

Figure 5:
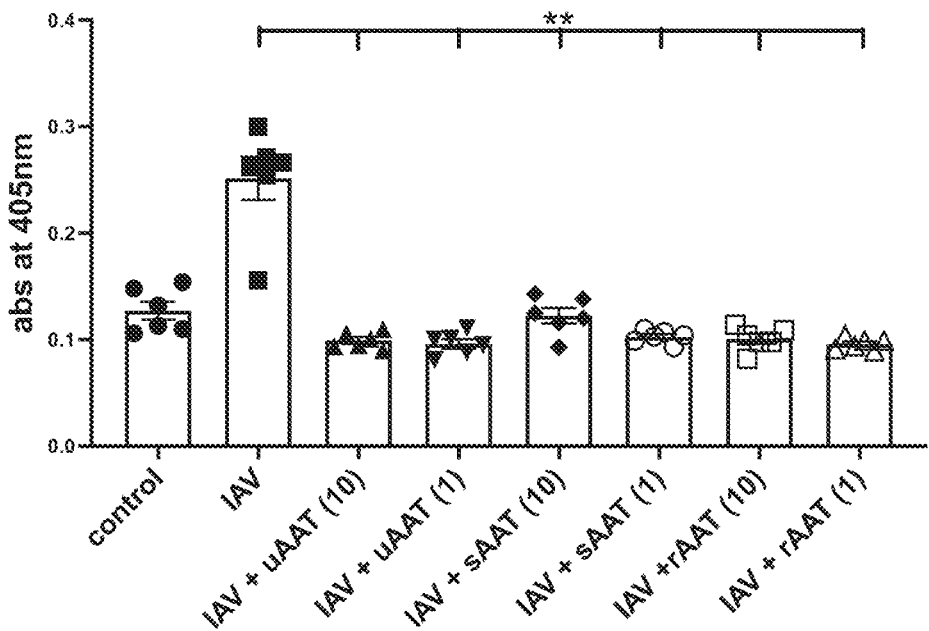

FIG. 5 shows effect of 3 different forms of AAT polypeptides produced in a CHO expression system, designated as uAAT, sAAT and rAAT and their ability to reduce NE activity in neutrophils infected with IAV. All 3 forms of AAT produced a similar significant reduction in NE activity.

Figure 6:
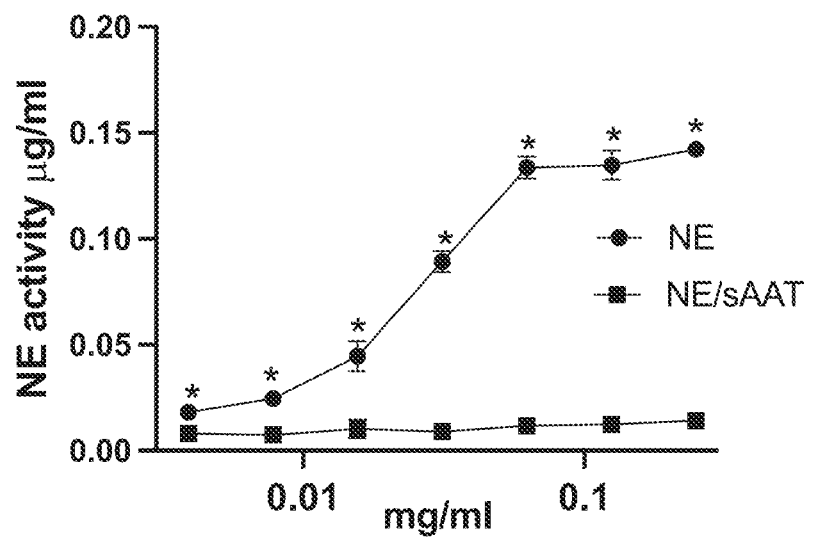

FIG. 6 shows a graph showing change in neutrophil elastase activity on administration of an AAT polypeptide according to the present disclosure, referred to as sAAT, which was produced in an *E. coli* expression system. The standard curve shows neutrophil elastase activity is reduced by sAAT (n=6, *p<0.05).

Figure 7:
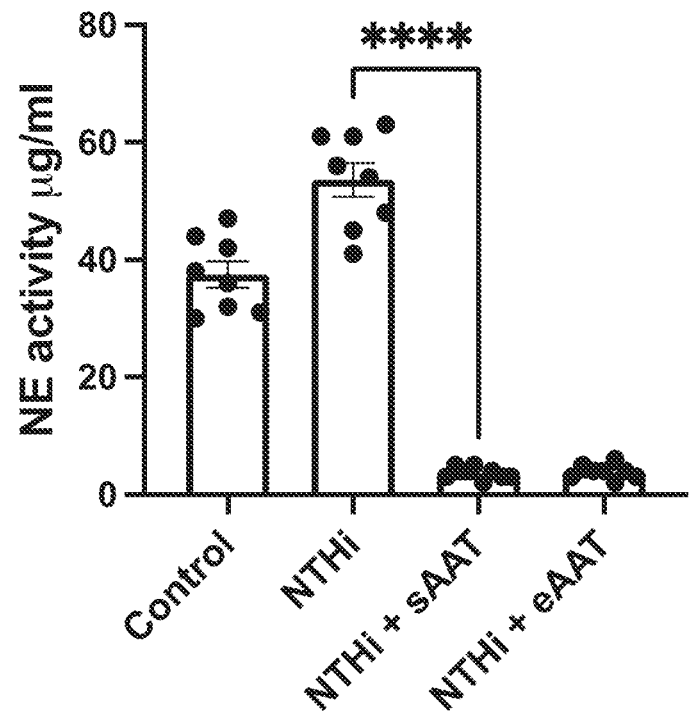

FIG. 7 shows a chart showing the results of an in-vitro NET model with NTHi infection, and shows that administration of an AAT polypeptide of the present disclosure (sAAT) which was produced in an *E. coli* expression system, or administration of eluted wildtype AAT (referred to as eAAT), significantly reduces neutrophil elastase activity.

Figure 8:
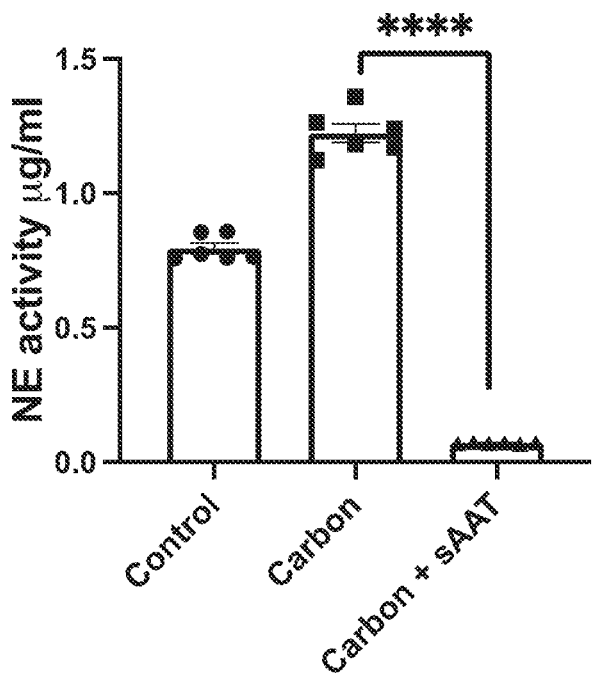

FIG. 8 shows a chart showing the change in neutrophil elastate activity in human blood neutrophils following incubation with carbon black nanoparticles, and then following administration of an AAT polypeptide according to the present disclosure (sAAT), which was produced in an *E. coli* expression system.

Figure 9:
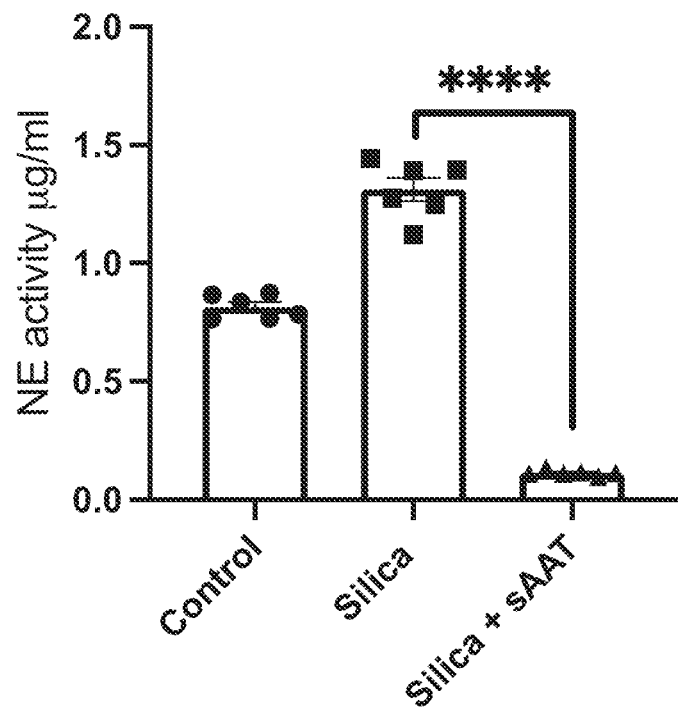

FIG. 9 shows a chart showing the change in neutrophil elastate activity in human blood neutrophils following incubation, with silica nanoparticles, and then following administration of an AAT polypeptide according to the present disclosure (sAAT), which was produced in an *E. coli* expression system.

Figure 10:
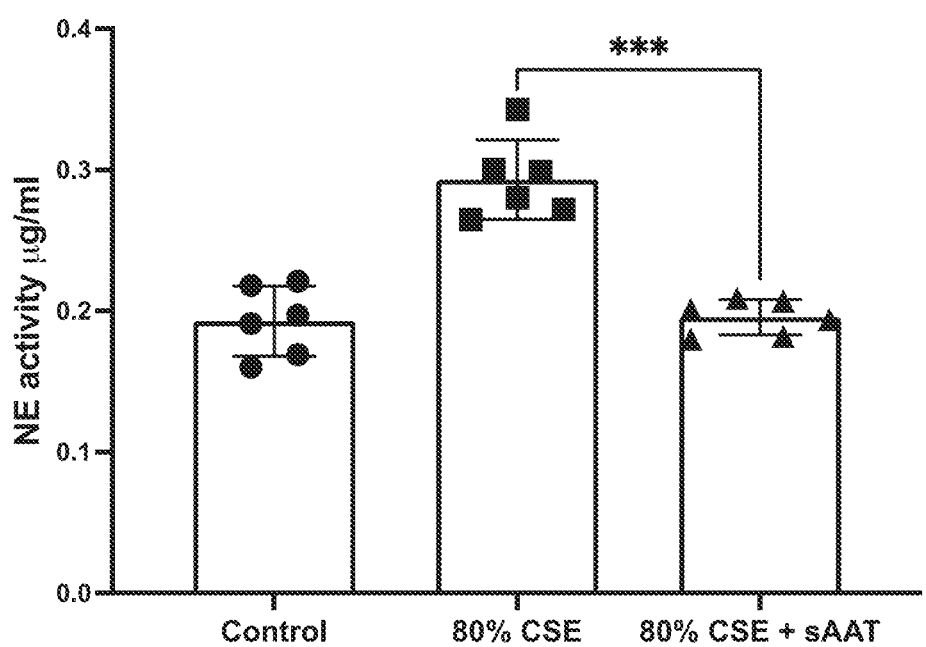

FIG. 10 shows a chart showing the change in neutrophil elastate activity in human blood neutrophils following incubation with cigarette smoke extract (CSE), and then following administration of an AAT polypeptide according to the present disclosure (sAAT), which was produced in an *E. coli* expression system.

Figure 11:
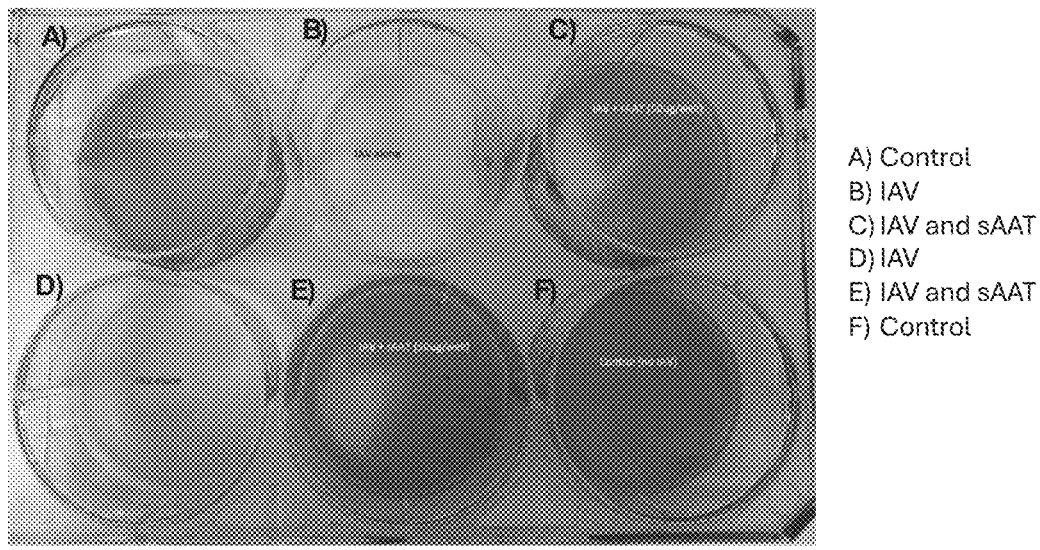

FIG. 11 shows a photograph of plaque assays showing the ability of a recombinant AAT polypeptide according to the present disclosure (sAAT), which was produced in an *E. coli* expression system, to reduce/prevent influenza A virus infection in an epithelial model. Assays which are purple/dark show no infection.

Figure 12:
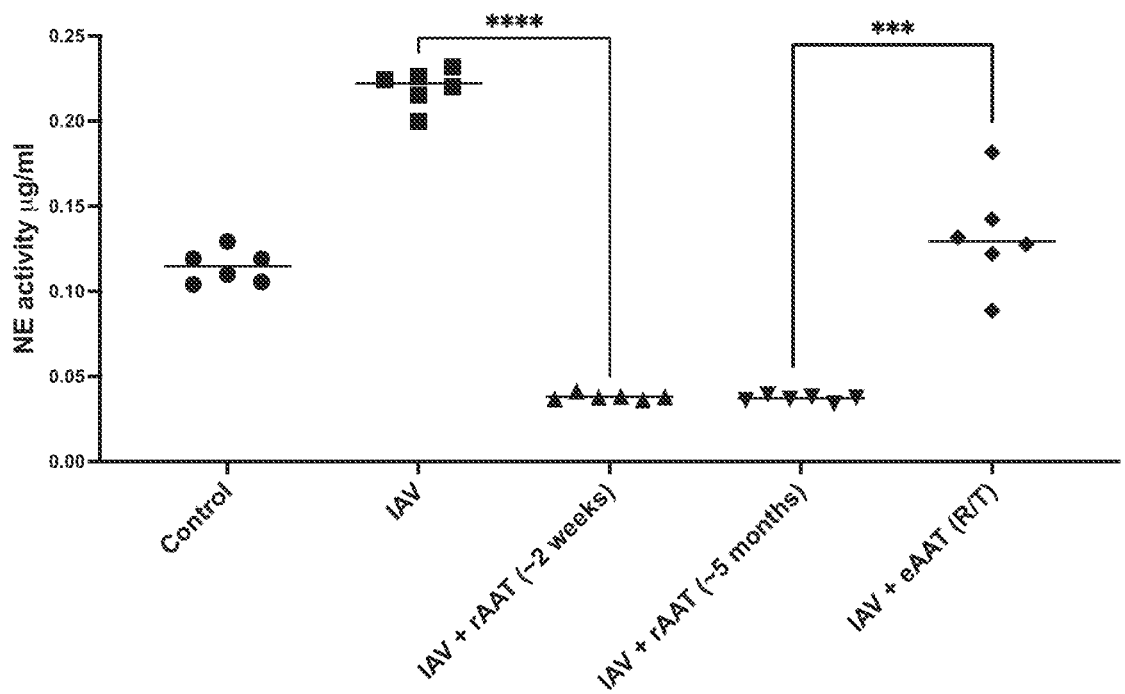

FIG. 12 shows a chart showing the results of an assay showing the ability of an AAT polypeptide according to the present disclosure (sAAT), which was produced in an *E. coli* expression system, and eluted wild type AAT (referred to as eAAT), to inhibit neutrophil elastase activity following influenza A infection of neutrophils, following storage of the AAT polypeptide for 2 weeks or 5 months in the refrigerator.

Figure 13:
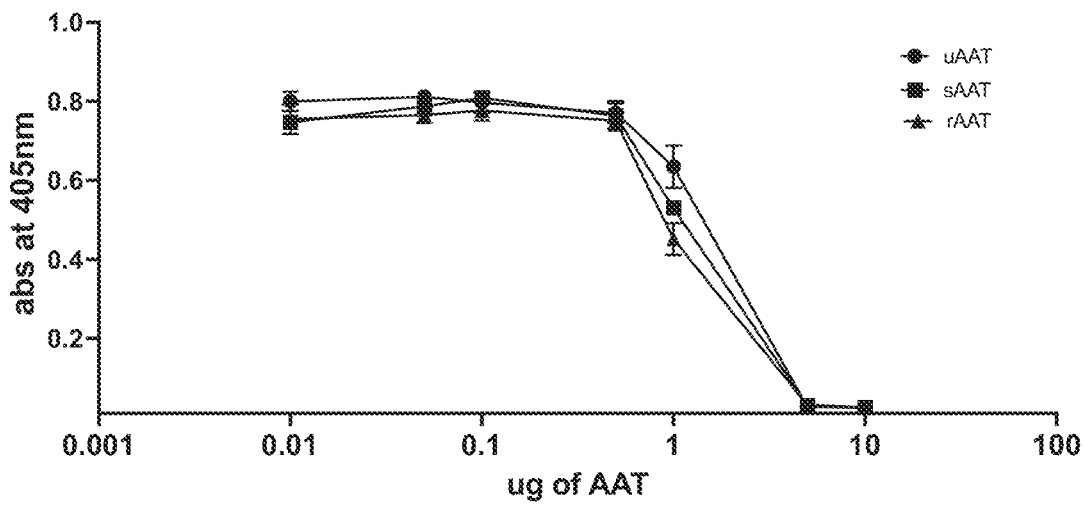

FIG. 13 shows a graph showing the results of an assay showing dose-response for three AAT polypeptides according to the present disclosure (uAAT, sAAT, rAAT) produced in a CHO expression system and their ability to inhibit neutrophil elastase activity.

Figure 14:
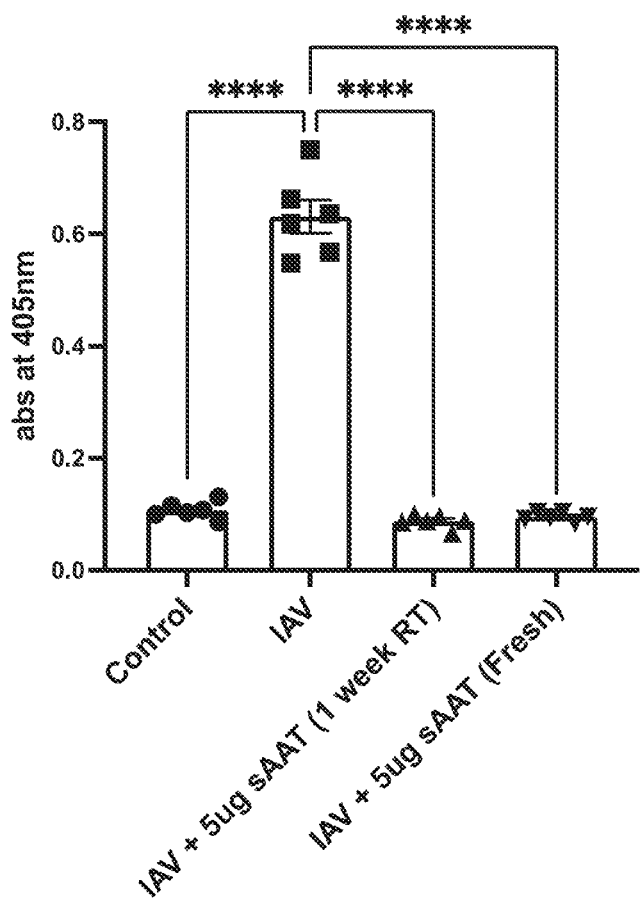

FIG. 14 shows a chart showing the results of an assay showing the ability of an AAT polypeptide according to the present disclosure (sAAT) which was produced in a CHO expression system, to inhibit neutrophil elastase activity in influenza A treated neutrophils, when treated fresh and after 1 week storage at ambient temperature.

Figure 15:
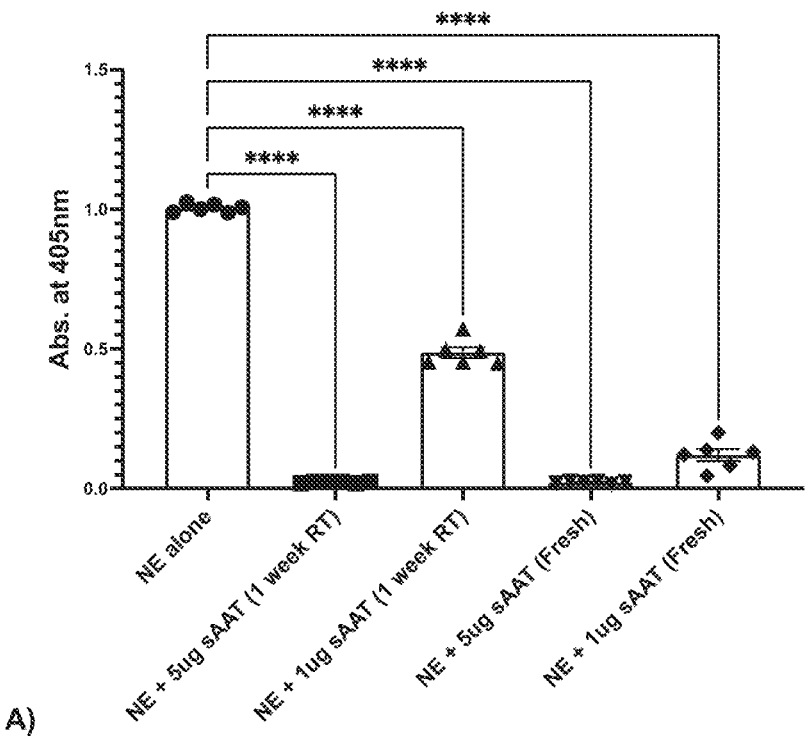
Figure 15:
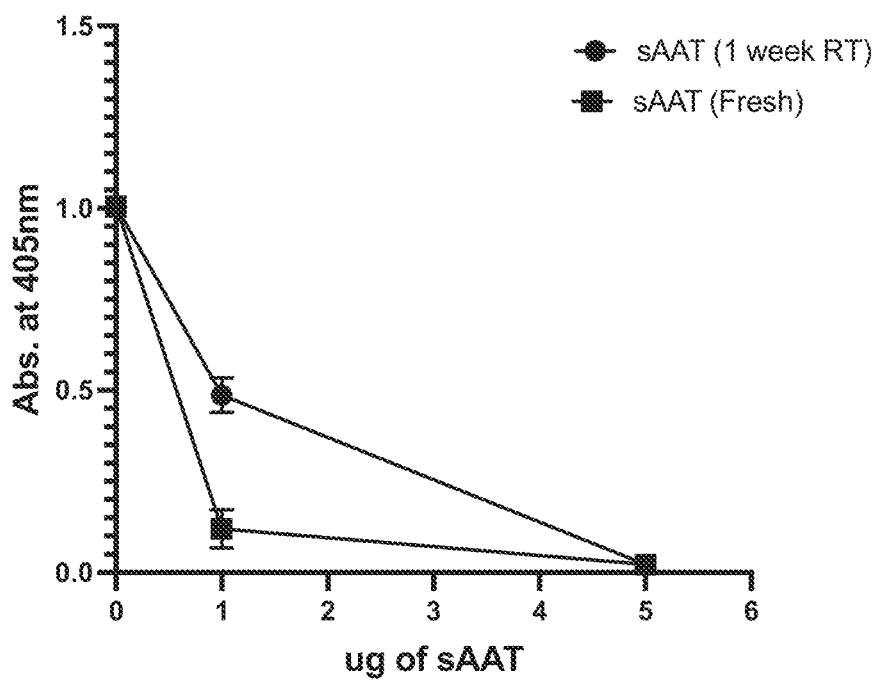

FIG. 15 A) shows a chart showing the results of an assay showing the ability of an AAT polypeptide according to the present disclosure (sAAT), which was produced in a CHO expression system, to reduce neutrophil elastate activity, when treated fresh and after 1 week storage at ambient temperature, at different dosage amounts; and B) shows a graph showing the results of an assay showing dose-response for an AAT polypeptide according to the present disclosure (sAAT), which was produced in a CHO expression system, to inhibit neutrophil elastase activity when treated with fresh sAAT or sAAT used following 1 week's storage at ambient temperature.

Figure 16:
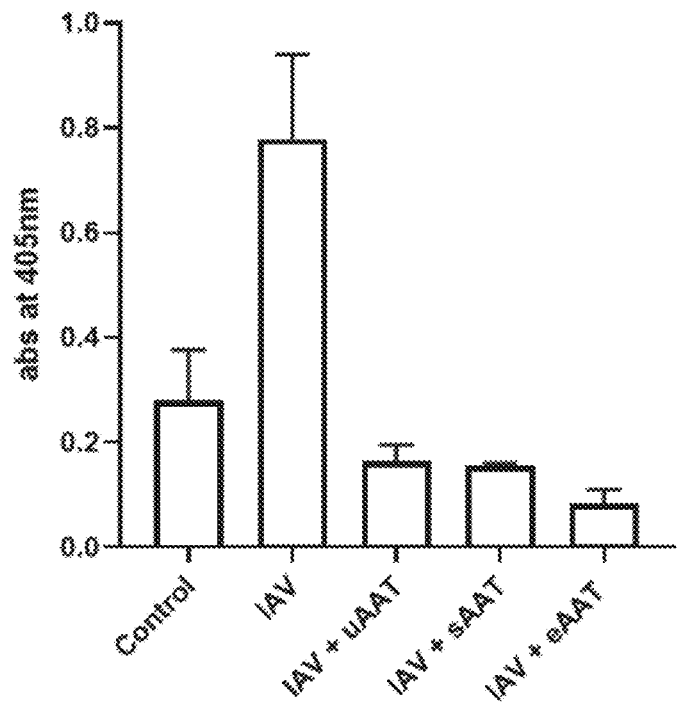

FIG. 16 shows a chart showing the results of an assay showing the ability of AAT polypeptides according to the present disclosure (sAAT, uAAT) produced in a CHO expression system and wild type AAT (referred to as eAAT) to inhibit neutrophil elastase activity in influenza A-treated neutrophils, when used in nebulised form.

Figure 17:
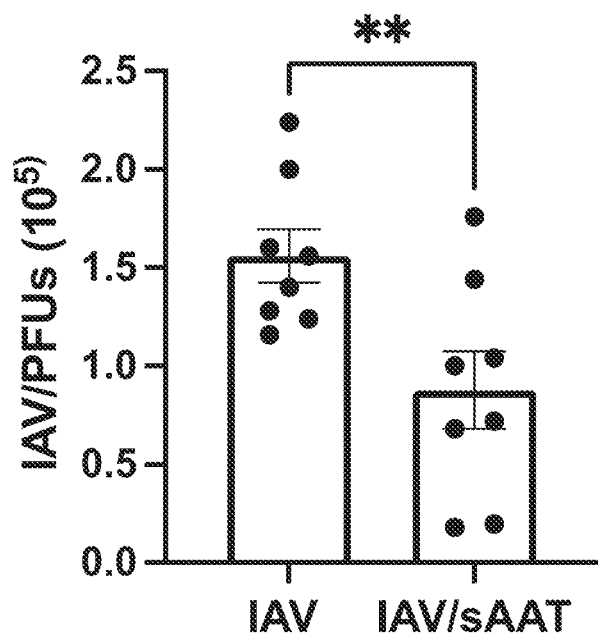

FIG. 17 shows the effect of the AAT polypeptide (sAAT) produced in a CHO expression system to reduce infection of human lung epithelial cells by IAV.

Figure 18:
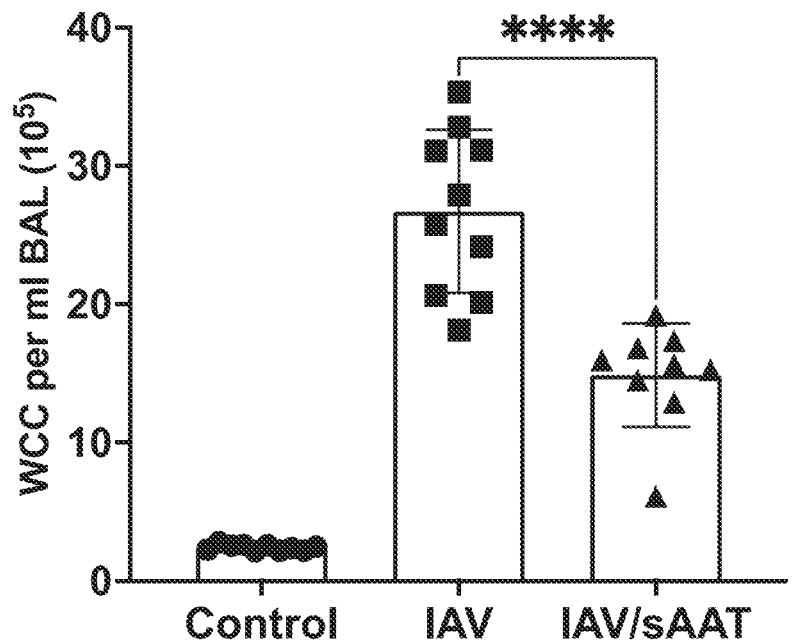

FIG. 18 shows the effect of the AAT polypeptide (sAAT) produced in a CHO expression system to treat lung inflammation by reduce lung airway white cell counts in mice infected with IAV (3 day exposure model).

Figure 19:
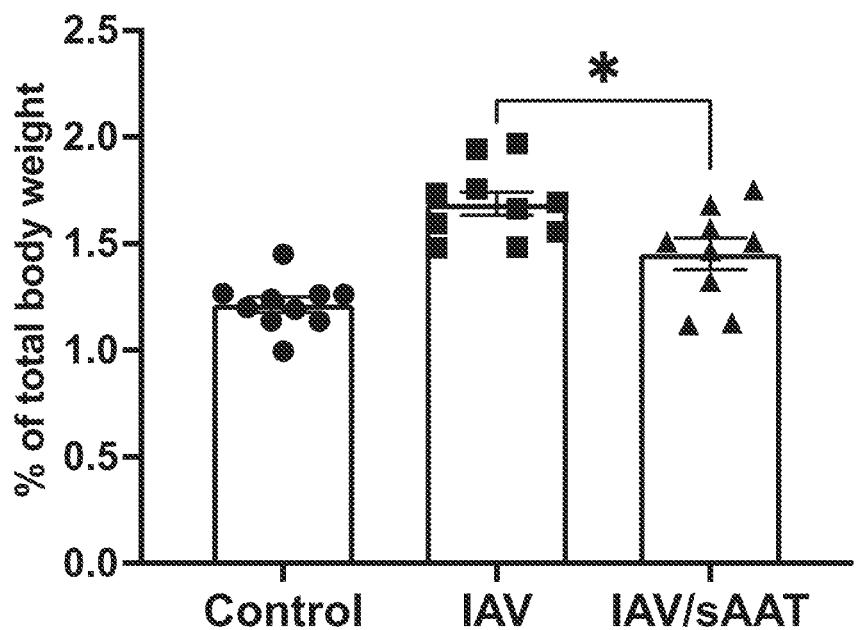

FIG. 19 shows the effect of the AAT polypeptide (sAAT) produced in a CHO expression system to treat lung inflammation by decreasing lung weight in mice infected with IAV (3 day exposure model).

Figure 20:
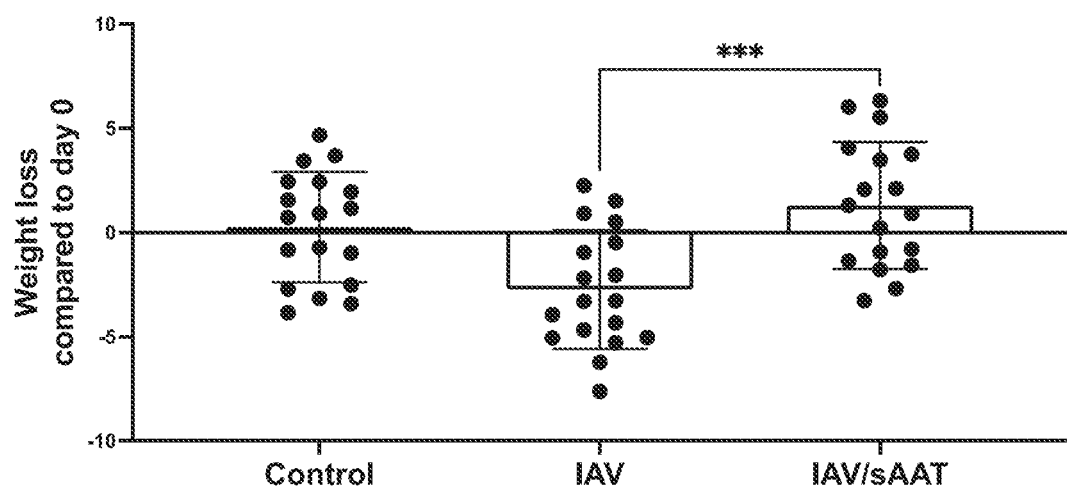

FIG. 20 shows the effect of the AAT polypeptide (sAAT) produced in a CHO expression system to treat lung inflammation by decreasing body weight loss in mice infected with IAV (5 day exposure model).

Figure 21:
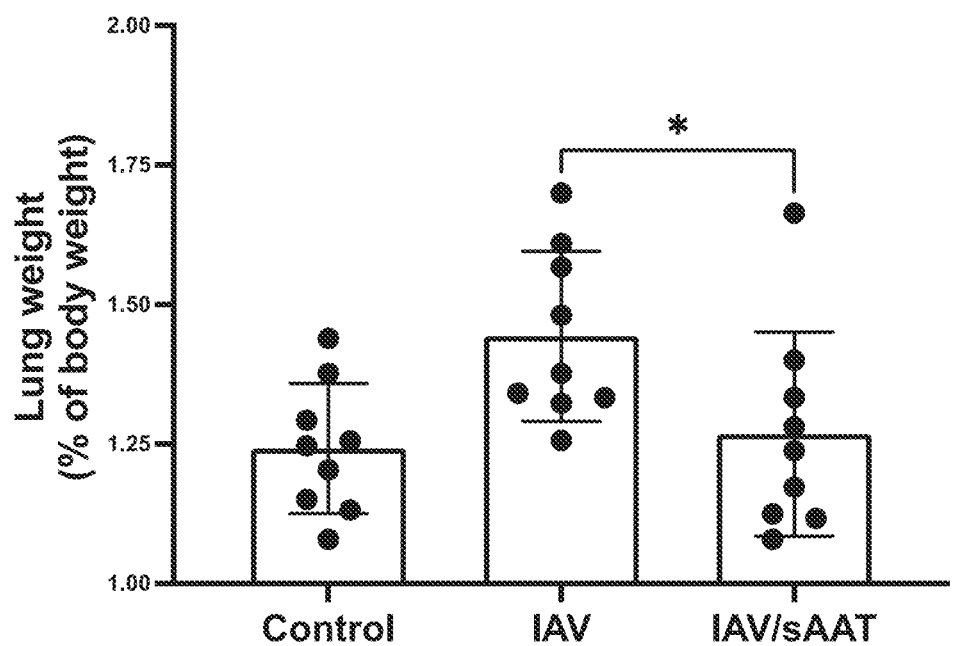

FIG. 21 shows the effect of the AAT polypeptide (sAAT) produced in a CHO expression system to treat lung inflammation by decreasing lung weight in mice infected with IAV (5 day exposure model).

Figure 22:
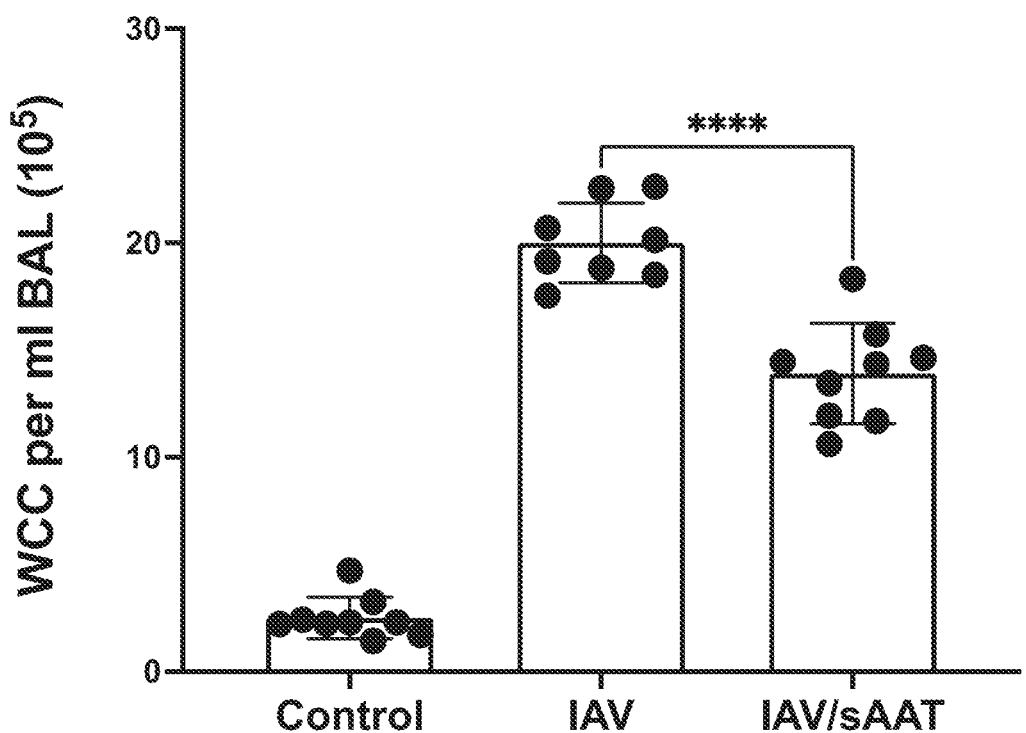

FIG. 22 shows the effect of the AAT polypeptide (sAAT) produced in a CHO expression system to treat lung inflammation by decreasing lung white cell count in bronchoalveolar (BAL) fluid in mice infected with IAV (5 day exposure model).

Figure 23:
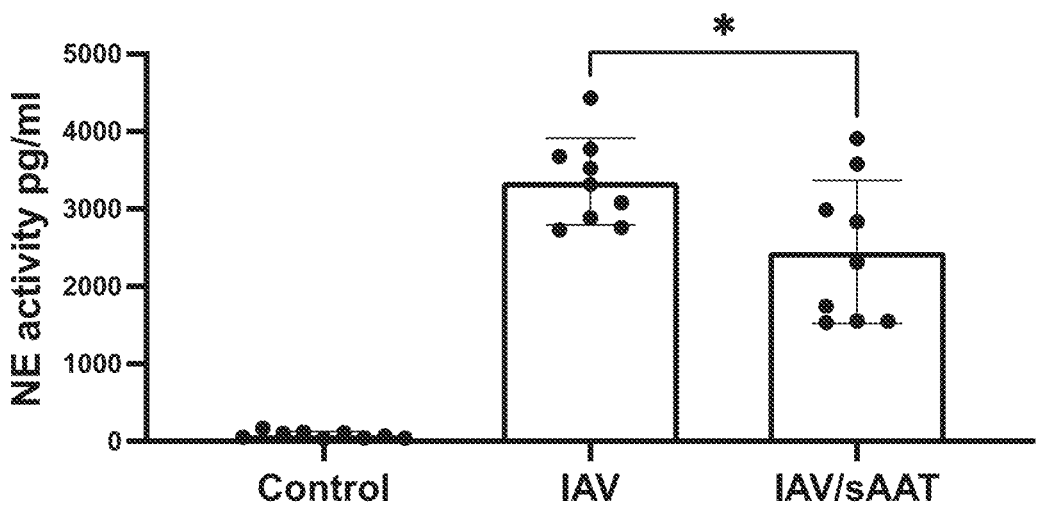

FIG. 23 shows the effect of the AAT polypeptide (sAAT) produced in a CHO expression system to treat lung inflammation by decreasing lung NE in mice infected with IAV (5 day exposure model).

Figure 24:
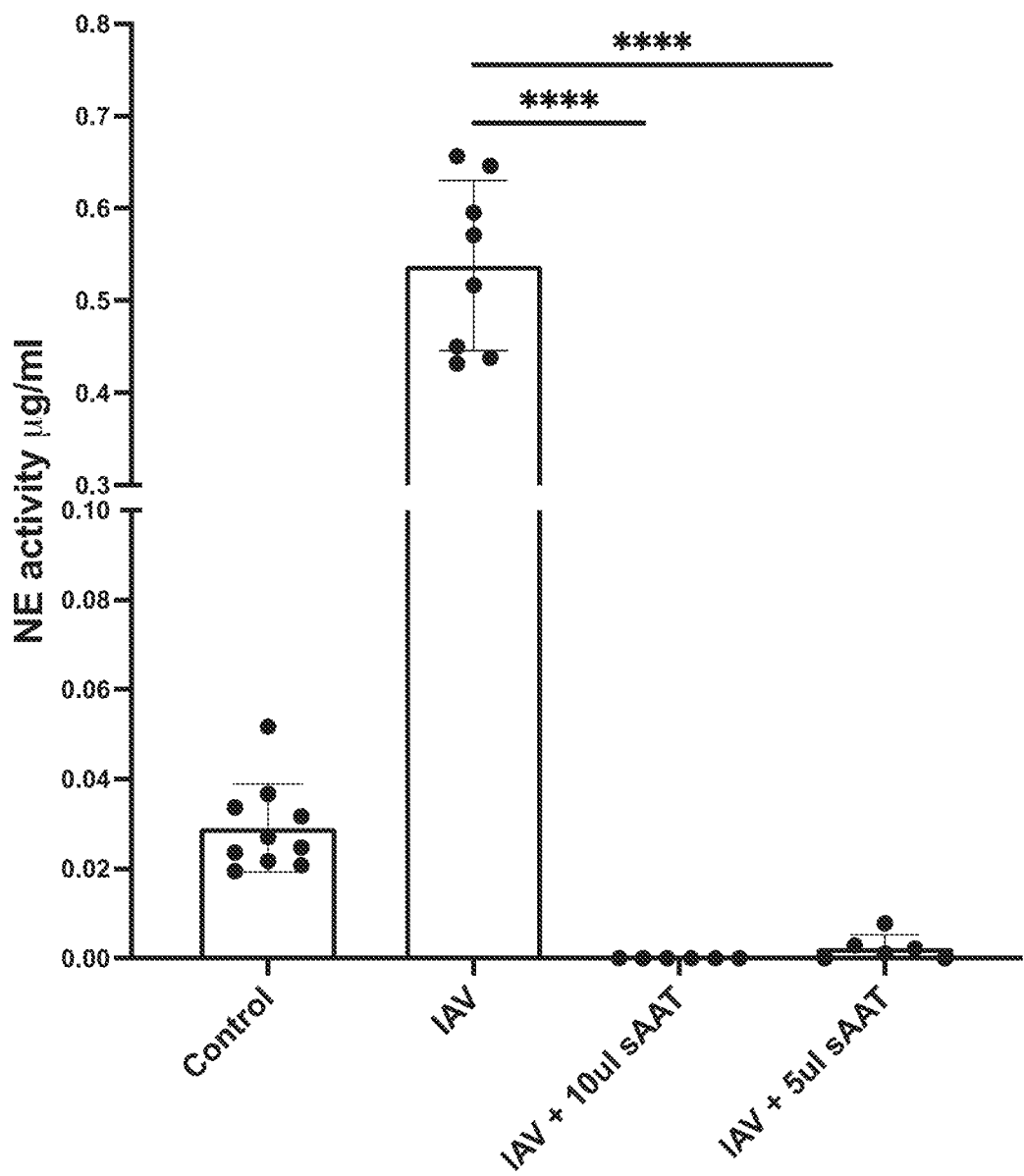

FIG. 24 shows the effect of lyophilised (freeze dried) AAT polypeptide (sAAT) produced in a CHO expression system that was reconstituted and its ability to reduce NE activity in vitro is assessed. The NET assay of NE expression was used as listed above and cells were exposed to IAV to increase NE activity. Two concentrations of the AAT used both abolished the NE activity.

DETAILED DESCRIPTION

Definitions

Unless otherwise defined, all technical and scientific terms used herein have the same meaning as commonly understood by one of ordinary skill in the art to which this disclosure belongs (e.g., molecular biology, structural biology, cell culture, protein synthesis, protein chemistry, medicinal chemistry, biochemistry).

It is to be understood that if any prior art publication is referred to herein, such reference does not constitute an admission that the publication forms a part of the common general knowledge in the art.

As used herein, the term "and/or", e.g., "X and/or Y" shall be understood to mean either "X and Y" or "X or Y" and shall be taken to provide explicit support for both meanings or for either meaning.

As used herein, the term about, unless stated to the contrary, refers to +/−10%, of the designated value.

Throughout this specification, unless specifically stated otherwise or the context requires otherwise, reference to a single step, composition of matter, group of steps or group of compositions of matter shall be taken to encompass one and a plurality (i.e. one or more) of those steps, compositions of matter, groups of steps or groups of compositions of matter. Thus, as used herein, the singular forms "a", "an" and "the" include plural aspects unless the context clearly dictates otherwise. For example, reference to "a" includes a single as well as two or more; reference to "an" includes a single as well as two or more; reference to "the" includes a single as well as two or more and so forth.

Unless otherwise indicated, terms such as "first," "second," etc. are used herein merely as labels, and are not intended to impose ordinal, positional, or hierarchical requirements on the items to which these terms refer. Moreover, reference to a "second" item does not require or preclude the existence of lower-numbered item (e.g., a "first" item) and/or a higher-numbered item (e.g., a "third" item).

As used herein, the phrase "at least one of", when used with a list of items, means different combinations of one or more of the listed items may be used and only one of the items in the list may be needed. The item may be a particular object, thing, or category. In other words, "at least one of" means any combination of items or number of items may be used from the list, but not all of the items in the list may be required. For example, "at least one of item A, item B, and item C" may mean item A; item A and item B; item B; item A, item B, and item C; or item B and item C. In some cases, "at least one of item A, item B, and item C" may mean, for example and without limitation, two of item A, one of item B, and ten of item C; four of item B and seven of item C; or some other suitable combination.

As used herein, the word "comprise" and other forms of the word, such as "comprising" and "comprises," means including but not limited to, and is not intended to exclude, for example, other additives, components, integers, or steps.

Each embodiment of the present disclosure described herein is to be applied mutatis mutandis to each and every other embodiment unless specifically stated otherwise or required otherwise by context.

Abbreviations

AECOPD Acute exacerbations of COPD
α1-AT α1-antitrypsin
AAT α1-antitrypsin
arb Arbitrary units
BAL Bronchoalveolar
bis-ANS 4,4'-Dianilino-1,1'-Binaphthyl-5,5'-Disulfonic Acid, Diphosphate salt
β-ME 2-mercaptoethanol
CD Circular dichroism
CT Computed tomography
CF Cystic fibrosis
COPD Chronic obstructive pulmonary disease
CSE Cigarette smoke exposure
D Denatured
DTT 1,4-Dithiothreitol
DMSO Dimethyl sulfoxide
eAAT eluted wild type AAT
E. coli Escherichia coli
EDTA ethylenediaminetetraacetic acid
GCS Glucocorticosteroids
GndHCl Guanidinium hydrochloride
GVHD Graft versus host disease
ΔG Gibbs free energy
ΔΔG Difference in Gibbs free energy
HNE Human neutrophil elastase
HPAI Highly pathogenic avian influenza
IAV Influenza A virus
IPTG Isopropyl ß-D-thiogalactoside
MD Molecular Dynamics
MET Macrophage extracellular trap
min Minute
MRI Magnetic resonance imaging
N Native
NET Neutrophil extracellular trap
NTHi Nontypeable *Haemophilus influenzae*
$OD_{600}$ Optical density at 600 nm
PAI-1 Plasminogen activator inhibitor-1
PCA Principle component analysis
PCLS Precision cut lung slices
PDB ID: Protein Data Bank identifier
PEG-3350/8000 Polyethylene glycol 3350/800
PFU Plaque-forming units
rAAT recombinant wild-type AAT
sAAT a mutated recombinant AAT
RCL Reactive centre loop
ROS Reactive oxygen species
RT, R/T Room temperature
SI Stoichiometry of inhibition
s Second
SDS-PAGE Sodium dodecyl sulfate polyacrylamide gel electrophoresis
Serpin Serine protease inhibitor
smFRET single-molecule Förster resonance energy transfer
Tm Midpoint of thermal denaturation
TEMED Tetramethylethylenediamine
TLR Toll-like receptor
uAAT a mutated recombinant AAT
WCC White cell count
WT Wild-type
wtAAT Wild-type AAT Sequences The amino acid sequences herein are shown with the N-terminus to the left, and where sequences are set out across multiple lines, the N-terminus is to the top left. Unless indicated otherwise, the amino acid residues in the sequences are L-amino acids.

The amino acid sequences listed in the application are shown using standard letter abbreviations for amino acids.

The specific sequences given herein relate to specific embodiments of the present disclosure.

AAT Polypeptides

The present disclosure is based on the surprising discovery that certain mutations in the sequence of AAT, and in particular combinations of mutations, can provide for improved stability of the resulting polypeptides whilst retaining functional properties. To date it has been challenging to stabilize the native state of AAT without compromising its function. The inventors have now identified combinations of mutations that interact and provide for improved properties such as stability, aggregation resistance and protein yields. These properties facilitate easier manufacture and distribution of AAT polypeptides, as well as facilitating increased ease of use and lifetime.

Accordingly in one aspect, there is provided an alpha-1 antitrypsin (AAT) polypeptide, comprising:
an amino acid sequence having at least 90% sequence identity to SEQ ID NO: 2;
wherein the amino acid sequence differs from SEQ ID NO: 2 in that it includes 3 or more amino acid substitutions from SEQ ID NO: 2 which are independently selected from the group consisting of G99A, Y144W, Y171A, L275F, S276K, T278E, T323E, I324V, D325N, K327E, and M358I.

Human wildtype AAT has the amino acid sequence shown in SEQ ID NO: 1, set out in FIG. 1. The AAT metastable native conformation consists of 3 β-sheets (A-C), 9 α-helices (A-I) and a protruding mobile loop, noted as the reactive centre loop (RCL). The largest element of the serpin structure is a central β-sheet, β-sheet A, which lies behind Helix-F. The hydrophobic core is comprised of strands 2-6 of β-sheet B (s2B, s3B, s4B, s5B and s6B) and helix-B, while β-sheet B also forms the B/C barrel with β-sheet C. The protruding RCL is important to the AAT inhibitory mechanism, acting as a bait for the target protease to bind. The loop is connected from strand 5 of β-sheet A and stand 1 of β-sheet C.

The AAT polypeptides of the present disclosure contain a portion of their amino acid sequence which is based on the amino acid residues from positions 41 to 418 of human AAT (SEQ ID No. 2), with at least 90% sequence identity to SEQ ID NO: 2, and also having at least three mutations from G99A, Y144W, Y171A, L275F, S276K, T278E, T323E, I324V, D325N, K327E, and M358I (and optionally further amino acid modifications, as long as the AAT polypeptide has a portion of its amino acid sequence which has at least 90% sequence identity to SEQ ID NO: 2).

Example polypeptides based on positions 41 to 418 with the amino acid modifications indicated have been shown to have improved stability whilst retaining functional potency, e.g. inhibiting neutrophil elastase activity.

In some embodiments, the amino acid sequence has 3, 4, 5, 6, 7, 8, 9, 10 or 11 mutations from SEQ ID NO: 2 which are independently selected from the group consisting of G99A, Y144W, Y171A, L275F, S276K, T278E, T323E, I324V, D325N, K327E, and M358I.

In some embodiments, the amino acid sequence has 4 or more, or 5 or more, or 6 or more, or 7 or more, or 8 or more, or 9 or more, or 10 or more, or 11 amino acid substitutions from SEQ ID NO: 2 which are independently selected from the group consisting of G99A, Y144W, Y171A, L275F, S276K, T278E, T323E, I324V, D325N, K327E, and M358I.

In some embodiments, the amino acid sequence has one, two or all of the following groups of amino acid substitutions from SEQ ID NO: 2:
  S276K, T278E, T323E, D325N and K327E;
  L275F, I324V and M358I; and
  G99A, Y144W and Y171A.

In some embodiments, the amino acid sequence includes the following amino acid substitutions from SEQ ID NO: 2:
  S276K, T278E, T323E, D325N and K327E.

In some embodiments, the amino acid sequence includes the following amino acid substitutions from SEQ ID NO: 2:
  L275F, I324V and M358I.

In some embodiments, the amino acid sequence includes the following amino acid substitutions from SEQ ID NO: 2:
  G99A, Y144W and Y171A.

In some embodiments, the amino acid sequence includes the following amino acid substitutions from SEQ ID NO: 2:
  L275F, S276K, T278E, T323E, I324V, D325N, K327E and M358I.

In some embodiments, the amino acid sequence includes the following amino acid substitutions from SEQ ID NO: 2:
  G99A, Y144W, Y171A, S276K, T278E, T323E, D325N and K327E.

In some embodiments, the amino acid sequence includes the following amino acid substitutions from SEQ ID NO: 2:
  G99A, Y144W, Y171A, L275F, I324V and M358I.

In some embodiments, the amino acid sequence includes the following amino acid substitutions from SEQ ID NO: 2:
  G99A, Y144W, Y171A, L275F, S276K, T278E, T323E, I324V, D325N, K327E, and M358I.

In some embodiments, the amino acid sequence includes 1 or more further amino acid substitutions from SEQ ID NO: 2 which are independently selected from the group consisting of F35L, T43A, T52A, A54G, S365A, and K371R.

In some embodiments, the amino acid sequence includes 2 or more, or 3 or more, or 4 or more, or 5 or more, or each of the following further amino acid substitutions from SEQ ID NO: 2: F35L, T43A, T52A, A54G, S365A, and K371R.

In some embodiments, the amino acid sequence includes the following further amino acid substitutions from SEQ ID NO: 2
  F35L, T43A, T52A, A54G, S365A, and K371R.

In some embodiments, the amino acid sequence includes the following amino acid substitutions from SEQ ID NO: 2:
  one, two or all of the following groups of amino acid substitutions:
  S276K, T278E, T323E, D325N and K327E;
  L275F, I324V and M358I; and
  G99A, Y144W and Y171A;
  and 1 or more further amino acid substitutions from SEQ ID NO: 2 which are independently selected from the group consisting of F35L, T43A, T52A, A54G, S365A, and K371R.

In some embodiments, the amino acid sequence includes the following amino acid substitutions from SEQ ID NO: 2:
  one, two or all of the following groups of amino acid substitutions:
  S276K, T278E, T323E, D325N and K327E;
  L275F, I324V and M358I; and
  G99A, Y144W and Y171A;
  and 2 or more, or 3 or more, or 4 or more, or 5 or more, or each of the following further amino acid substitutions from SEQ ID NO: 2 which are independently selected from the group consisting of F35L, T43A, T52A, A54G, S365A, and K371R.

In some embodiments, the amino acid sequence includes the following amino acid substitutions from SEQ ID NO: 2
  F35L, T43A, T52A, A54G, G99A, Y144W, Y171A, L275F, S276K, T278E, T323E, I324V, D325N, K327E, M358I, S365A and K371R.

The AAT polypeptide comprises an amino acid sequence having at least 90% sequence identity to SEQ ID NO: 2, and which differs from SEQ ID NO:2 in that it includes 3 or more amino substitutions as specified herein.

The AAT polypeptide may if desired contain additional amino acid sequence to the amino acid sequence based on SEQ ID NO: 2. For example, in some embodiments it may contain additional N-terminal amino acid sequence and/or C-terminal amino acid sequence, in addition to comprising an amino acid sequence which has at least 90% sequence identity to SEQ ID NO:2.

In some embodiments, the AAT polypeptide comprises additional N-terminal amino acid sequence.

In some embodiments, the AAT polypeptide comprises additional C-terminal amino acid sequence.

In some embodiments, the AAT polypeptide comprises a CHO N-terminus sequence.

In some embodiments, the AAT polypeptide comprises an *E. Coli* N-terminus sequence.

In some embodiments, the AAT polypeptide comprises the N-terminal sequence MENLYFQGAAS (SEQ ID NO: 7).

In some embodiments, the AAT polypeptide comprises the N-terminal sequence MPSSVSWGILLLAGLC-CLVPVSLAEDPQGDAAQKTDTSHH (SEQ ID NO: 8).

In some embodiments, the AAT polypeptide comprises the N-terminal sequence MPSSVSWGILLLAGLC-CLVPVSLAE (SEQ ID NO:9).

In some embodiments, the AAT polypeptide comprises a His-tag sequence, for example an N-terminal His-tag sequence.

The AAT polypeptide amino acid sequence which is based on SEQ ID NO: 2 has at least 90% sequence identity to SEQ ID NO: 2.

In some embodiments, the portion of the AAT polypeptide which is the amino acid sequence based on SEQ ID NO: 2 has no amino acid modifications from SEQ ID NO: 2, other than:
  including 3 or more amino acid substitutions from SEQ ID NO: 2 which are independently selected from the group consisting of G99A, Y144W, Y171A, L275F, S276K, T278E, T323E, I324V, D325N, K327E, and M358I; and
  optionally including 1 or more further amino acid substitutions from SEQ ID NO: 2 which are independently selected from the group consisting of F35L, T43A, T52A, A54G, S365A, and K371R. In other words, the portion of the AAT polypeptide which is based on SEQ ID NO: 2 has no modifications to the amino acid sequence other than at those specific positions.

However, it will be understood that AAT polypeptides which contain amino acid sequences that are further variants of SEQ ID NO: 2, having amino acid modifications (e.g. substitutions, deletions, insertions) at other positions, may share the beneficial stability properties observed for the example AAT polypeptides and also retain functional activity.

Accordingly, in some embodiments, the AAT polypeptide contains an amino acid sequence based on SEQ ID NO:2, but having one or more further modifications from the sequence of SEQ ID NO: 2, in addition to any substitutions at the positions defined above.

In some embodiments, the one or more further modifications are one or more substitutions. In some embodiments, the one or more further modifications are one or more conservative substitutions.

A conservative substitution is the replacement of an amino acid residue by another, biologically similar residue in a polypeptide. The term "conservative variation" also includes the use of a substituted amino acid, i.e. an amino acid with one or more atoms replaced with another atom or group, in place of a parent amino acid provided that the polypeptide substantially retains its activity or provided that antibodies raised to the substituted polypeptide also immunoreact with the unsubstituted polypeptide.

Typical but not limiting conservative substitutions are the replacements, for one another, among the aliphatic amino acids Ala, Val, Leu and Iie; interchange of hydroxyl-containing residues Ser and Thr, interchange of the acidic residues Asp and Glu, interchange between the amide-containing residues Asn and Gln, interchange of the basic residues Lys and Arg, interchange of the aromatic residues Phe and Tyr, and interchange of the small-sized amino acids Ala, Ser, Thr, Met and Gly. Additional conservative substitutions include the replacement of an amino acid by another of similar spatial or steric configuration, for example the interchange of Asn for Asp, or Gln for Glu. Non-limiting examples of conservative amino acid substitutions include the following:

Original Residue Conservative Substitutions
Ala Gly, Val, Leu, Ile, Ser, Thr, Met
Arg Lys
Asn Asp, Gln, His
Asp Glu, Asn
Cys Ser
Gln Asn, His, Lys, Glu Glu Asp, Gln
Gly Ala, Ser, Thr, Met
His Asn, Gln
Ile Ala, Leu, Val, Met
Leu Ala, Ile, Val, Met
Lys Arg
Met Leu, Ile, Ala, Ser, Thr, Gly
Phe Leu, Tyr, Trp
Ser Thr, Cys, Ala, Met, Gly
Thr Ser, Ala, Ser, Met, Gly
Trp Tyr, Phe
Tyr Trp, Phe
Val Ala, Ile, Leu Oxidation of methione in the reactive center loop can reduce the inhibitory activity of AAT.

In some embodiments, the AAT polypeptide has an additional modification from the sequence of SEQ ID NO: 2 (i.e. other than the possible modifications discussed above at positions 35, 43, 52, 54, 99, 144, 171, 275, 276, 278, 323, 324, 325, 327, 358, 365 and/or 371) in that the amino acid at position 335 is other than Met.

In some embodiments, the AAT polypeptide has an additional modification from the sequence of SEQ ID NO: 2 in that the amino acid at position 335 is an amino acid with a hydrophobic side chain, e.g. selected from Val, Leu, Ile and Ala. In some embodiments, the amino acid residue is Val. In some embodiments, the amino acid residue is Leu.

In some embodiments, the AAT polypeptide has an additional modification from the sequence of SEQ ID NO: 2 in that the amino acid at position 335 is glycine.

In some embodiments, the AAT polypeptide has an additional modification from the sequence of SEQ ID NO: 2 in that the amino acid at position 335 is a charged residue, e.g. selected from Glu and Asp. In some embodiments, the amino acid residue is Glu.

In some embodiments, the AAT polypeptide has an additional modification from the sequence of SEQ ID NO: 2 (i.e. other than the possible modifications discussed above at positions 35, 43, 52, 54, 99, 144, 171, 275, 276, 278, 323, 324, 325, 327, 358, 365 and/or 371) in that the amino acid at position 342 is other than Met, In some embodiments, the AAT polypeptide has an additional modification from the sequence of SEQ ID NO: 2 in that the amino acid at position 342 is an amino acid with a hydrophobic side chain, e.g. selected from Val, Leu, Ile and Ala. In some embodiments, the amino acid residue is Val. In some embodiments, the amino acid residue is Leu.

In some embodiments, the AAT polypeptide has an additional modification from the sequence of SEQ ID NO: 2 in that the amino acid at position 342 is glycine.

In some embodiments, the AAT polypeptide has an additional modification from the sequence of SEQ ID NO: 2 in that the amino acid at position 342 is a charged residue, e.g. selected from Glu and Asp. In some embodiments, the amino acid residue is Glu.

In some embodiments, the only additional modifications in the amino acid sequence of the AAT polypeptide from the sequence of SEQ ID NO: 2 (i.e. other than the possible modifications discussed above at positions 35, 43, 52, 54, 99, 144, 171, 275, 276, 278, 323, 324, 325, 327, 358, 365 and/or 371) in that the amino acid at position 335 is other than Met and/or the amino acid at position 342 is other than Met. For example, the amino acid at position 335 may be Val, Leu or Glu, and the amino acid at position 342 may be Leu.

In some embodiments, the portion of the AAT polypeptide which is the amino acid sequence based on SEQ ID NO: 2 has not more than 5 amino acid modifications (e.g. not more than 5 conservative substitutions) from SEQ ID NO: 2, other than:
    including 3 or more amino acid substitutions from SEQ ID NO: 2 which are independently selected from the group consisting of G99A, Y144W, Y171A, L275F, S276K, T278E, T323E, I324V, D325N, K327E, and M358I; and
    optionally including 1 or more further amino acid substitutions from SEQ ID NO: 2 which are independently selected from the group consisting of F35L, T43A, T52A, A54G, S365A, and K371R.

In some embodiments, the portion of the AAT polypeptide which is the amino acid sequence based on SEQ ID NO: 2 has not more than 10 amino acid modifications (e.g. not more than 10 conservative substitutions) from SEQ ID NO: 2, other than:

including 3 or more amino acid substitutions from SEQ ID NO: 2 which are independently selected from the group consisting of G99A, Y144W, Y171A, L275F, S276K, T278E, T323E, I324V, D325N, K327E, and M358I; and optionally including 1 or more further amino acid substitutions from SEQ ID NO: 2 which are independently selected from the group consisting of F35L, T43A, T52A, A54G, S365A, and K371R.

In some embodiments, the portion of the AAT polypeptide which is the amino acid sequence based on SEQ ID NO: 2 has up to 19 amino acid substitutions from SEQ ID NO 2 which are:

3 or more amino acid substitutions from SEQ ID NO: 2 which are independently selected from the group consisting of G99A, Y144W, Y171A, L275F, S276K, T278E, T323E, I324V, D325N, K327E, and M358I;

optionally 1 or more further amino acid substitutions from SEQ ID NO: 2 which are independently selected from the group consisting of F35L, T43A, T52A, A54G, S365A, and K371R; and optionally 1 or more additional amino acid substitutions from SEQ ID NO: 2 which are independently selected from the group consisting of M335V, M335L, M335I, M335A, M335E or M335D, and M342L.

In some embodiments, the portion of the AAT polypeptide which is the amino acid sequence based on SEQ ID NO: 2 has at least 91%, at least 92%, at least 93%, at least 94%, at least 95%, at least 96%, at least 97%, at least 98% or at least 99% sequence identity to SEQ ID NO: 2.

In some embodiments, the portion of the AAT polypeptide which is the amino acid sequence based on SEQ ID NO: 2 has not more than 35, not more than 30, not more than 25, not more than 20 amino acid modifications, not more than 19 amino acid modifications, not more than 18 modifications, or not more than 17 modifications, from SEQ ID NO:2.

In some embodiments, any modifications other than the specific modification set out above, are conservative substitutions.

In some embodiments, the AAT polypeptide has an amino acid sequence consisting of the amino acid sequence of any of the example AAT polypeptides, e.g. it has the amino acid sequence of SEQ ID NO: 3, SEQ ID NO: 4, SEQ ID NO: 5 and SEQ ID NO: 6.

In some embodiments, the AAT polypeptide has an amino acid sequence which is based on the amino acid sequence of SEQ ID NO:2, which has 3 or more amino acid substitutions from SEQ ID NO: 2 which are independently selected from the group consisting of G99A, Y144W, Y171A, L275F, S276K, T278E, T323E, I324V, D325N, K327E, and M358I;

which optionally has 1 or more further amino acid substitutions from SEQ ID NO: 2 which are independently selected from the group consisting of F35L, T43A, T52A, A54G, S365A, and K371R;

which optionally has an additional amino acid substation from SEQ ID NO: 2 which is selected from the group consisting of M335V, M335L, M335I, M335A, M335E or M335D;

which optionally has an additional amino acid substation from SEQ ID NO: 2 which is selected from the group consisting of M342L;

which optionally has additional N-terminal amino acid sequence and/or C-terminal amino acid sequence;

which is optionally a derivative, selected from the group consisting of amidation, glycosylation, carbamylation, acylation, sulfation, phosphorylation, cyclization, lipidization, pegylation and fusion to another peptide or protein to form a fusion protein;

and which does not have other modifications from the amino acid sequence of SEQ ID NO: 2.

AAT Polypeptide Derivatives and Salts

The present disclosure encompasses AAT polypeptides in all forms in which they can be produced, including derivatives, salts and/or solvates.

Whilst in some embodiments, the present disclosure relates to an AAT polypeptide which is not a derivative, in other embodiments the present disclosure relates to an AAT polypeptide in which the amino acid sequence has been derivatised.

The AAT polypeptide may for example comprise one or more derivatisations selected from amidation, glycosylation, carbamylation, acylation, sulfation, phosphorylation, cyclization, lipidization, pegylation and fusion to another peptide or protein to form a fusion protein.

For example, the derivative may comprise one or more derivatisations selected from amidation, esterification, glycosylation, carbamylation, acylation, sulfation, phosphorylation, cyclization, lipidization and PEGylation.

In some embodiments, the AAT polypeptide comprises a modification selected from the group consisting of glycosylation, PEGylation, prenylation, acylation, a biotinylation, phosphorylation, and conjugation to a lipid moiety.

The structure may in some embodiments be modified at random positions within the molecule or, in some other embodiments, at predetermined positions within the molecule and may include one, two, three or more attached chemical moieties.

For example, pharmaceutically acceptable esters and amides of the AAT polypeptides of the present disclosure may comprise a C1.20 alkyl-, C2-20 alkenyl-, C5-10 aryl-, C5-10 ar-Ci-20 alkyl-, or amino acid-ester group or amide group attached at an appropriate site, for example formed by reaction of an alkyl, alkenyl aryl, aralkyl or amino alkyl group containing an alcohol or amino moiety with an acid moiety present in the AAT polypeptide amino acid sequence, or formed by reaction of an alkyl, alkenyl aryl, aralkyl or amino alkyl group containing an activated acyl group with an alcohol or amine group present in the AAT polypeptide amino acid sequence. Examples of suitable moieties are hydrophobic substituents with 4 to 26 carbon atoms. Suitable lipid groups include fatty acids (e.g. lauroyl, palmityl, oleyl or stearyl (C17H35)) and bile acids (e.g. cholate or deoxycholate).

The AAT polypeptide may for example be PEGylated. Derivatives which are PEGylated may provide additional advantages such as increased solubility, stability and circulating time of the polypeptide, or decreased immunogenicity.

Chemical moieties for derivatisation may also be selected from water soluble polymers such as polyethylene glycol, ethylene glycol/propylene glycol copolymers, carboxymethylcellulose, dextran, polyvinyl alcohol and the like. A polymer moiety for derivatisation of an AAT polypeptide of the present disclosure may be of any molecular weight and may be branched or unbranched.

Salt forms of AAT polypeptides also form part of the present disclosure. Salts of AAT polypeptides of the present disclosure include those which are pharmaceutically acceptable, i.e. which are suitable for use in medicine. Suitable salts according to the present disclosure include those formed with organic or inorganic acids or bases.

Pharmaceutically acceptable acid addition salts include those formed with hydrochloric, hydrobromic, sulphuric, nitric, citric, tartaric, acetic, phosphoric, lactic, pyruvic, acetic, trifluoroacetic, succinic, perchloric, fumaric, maleic, glycolic, salicylic, oxaloacetic, methanesulfonic, ethanesulfonic, p-toluenesulfonic, formic, benzoic, malonic, naphthalene-2-sulfonic, benzenesulfonic, and isethionic acids.

Pharmaceutically acceptable salts with bases include ammonium salts, alkali metal salts, for example potassium and sodium salts, alkaline earth metal salts, for example calcium and magnesium salts, and salts with organic bases, for example dicyclohexylamine and N-methyl-D-glucomine.

Those skilled in the art will appreciate that many organic compounds can form complexes with solvents in which they are reacted or from which they are precipitated or crystallized. Such complexes are known as "solvates". For example, a complex with water is known as a "hydrate". The present disclosure also encompasses solvated forms of the AAT polypeptides, solvates of derivatives of the compounds, and solvates of salts of the derivatives. Those skilled in the art will also appreciate than many organic compounds can exist in different forms, including as amorphous material and/or in one or more crystalline forms. Different physical forms of organic compounds are known as polymorphs. The present disclosure also encompasses all such different physical forms of the AAT polypeptides, as well as different physical forms of their derivatives and salts.

Properties of AAT Polypeptides

The AAT polypeptides of the present disclosure have activity similar to wild type alpha-1 antitrypsin, e.g. in inhibiting neutrophil elastase, downregulating proteases and/or in mediating anti-inflammatory effects. The AAT polypeptides thus find use in therapeutic applications, including diseases and disorders associated with AAT deficiency. Neutrophil-driven inflammation is specifically targeted by the action of AAT.

In some embodiments, the AAT polypeptides have at least $\frac{1}{100}^{th}$ of the activity of wild type human AAT in inhibiting neutrophil elastase, or at least $\frac{1}{50}^{th}$ of the activity of wild type human AAT in inhibiting neutrophil elastase, or at least $\frac{1}{20}^{th}$ of the activity of wild type human AAT in inhibiting neutrophil elastase, or at least $\frac{1}{10}^{th}$ of the activity of wild type human AAT in inhibiting neutrophil elastase, or at least 50% of the activity of wild type human AAT in inhibiting neutrophil elastase, or at least 80% of the activity of wild type human AAT in inhibiting neutrophil elastase, to at least 90% of the activity of wild type human AAT in inhibiting neutrophil elastase, or at least 95% of the activity of wild type human AAT in inhibiting neutrophil elastase, or at least 100% of the activity of wild type human AAT in inhibiting neutrophil elastase.

In some embodiments, neutrophil elastase inhibitory activity is determined according to an assay as referred to in the examples.

Example AAT polypeptides according to the present disclosure have been found to have improved thermal stability compared to wild-type human AAT. Thus, in some embodiments, the AAT polypeptide has improved thermal stability compared to wild-type human AAT.

Example AAT polypeptides according to the present disclosure have been found to have improved re-fold yield compared to wild-type human AAT, providing access to higher yield of the polypeptide. Thus, in some embodiments, the AAT polypeptide has improved re-fold yield compared to wild-type human AAT. In some embodiments, the AAT polypeptide can be obtained with a refold yield of at least 25%, or at least 30%, or at least 35%, or at least 40%, or at least 45%, or at least 50%, or at least 55%, or at least 60%.

In some embodiments, the AAT polypeptide retains at least 50%, at least 60%, at least 70%, at least 80%, or at least 90% of its activity in inhibiting neutrophil elastase (e.g. using an assay described in the examples) following storage at 4° C. for a period of 2 weeks.

In some embodiments, the AAT polypeptide retains at least 50%, at least 60%, at least 70%, at least 80%, or at least 90% of its activity in inhibiting neutrophil elastase (e.g. using an assay described in the examples) following storage at 4° C. for a period of 1 month.

In some embodiments, the AAT polypeptide retains at least 50%, at least 60%, at least 70%, at least 80%, or at least 90% of its activity in inhibiting neutrophil elastase (e.g. using an assay described in the examples) following storage at 4° C. for a period of 2 months.

In some embodiments, the AAT polypeptide retains at least 50%, at least 60%, at least 70%, at least 80%, or at least 90% of its activity in inhibiting neutrophil elastase (e.g. using an assay described in the examples) following storage at 4° C. for a period of 3 months.

In some embodiments, the AAT polypeptide retains at least 50%, at least 60%, at least 70%, at least 80%, or at least 90% of its activity in inhibiting neutrophil elastase (e.g. using an assay described in the examples) following storage at 4° C. for a period of 4 months.

In some embodiments, the AAT polypeptide retains at least 50%, at least 60%, at least 70%, at least 80%, or at least 90% of its activity in inhibiting neutrophil elastase (e.g. using an assay described in the examples) following storage at 4° C. for a period of 5 months.

In some embodiments, the AAT polypeptide retains at least 50%, at least 60%, at least 70%, at least 80%, or at least 90% of its activity in inhibiting neutrophil elastase (e.g. using an assay described in the examples) following storage at 4° C. for a period of 6 months.

Preparation of AAT Polypeptides

The AAT polypeptides of the present disclosure may be produced by recombinant methods which are known in the art or alternatively they may be produced by synthetic methods, again which are known in the art.

For example, the AAT polypeptides may for instance be produced by classical peptide synthesis, e.g., solid phase peptide synthesis using t-Boc or Fmoc chemistry or other well established techniques, see, e.g., Greene and Wuts, "Protective Groups in Organic Synthesis", John Wiley & Sons, 1999, Florencio Zaragoza DOrwald, "Organic Synthesis on solid Phase", Wiley-VCH Verlag GmbH, 2000, and "Fmoc Solid Phase Peptide Synthesis", Edited by W. C. Chan and P. D. White, Oxford University Press, 2000.

Also, or alternatively, the AAT polypeptides may be produced by recombinant methods, viz. by culturing a host cell containing a DNA sequence encoding the fragment and capable of expressing the peptide in a suitable nutrient medium under conditions permitting the expression of the peptide. Non-limiting examples of host cells suitable for expression of these peptides are: *Escherichia coli. Saccharomyces cerevisiae*, as well as mammalian BHK or CHO cell lines.

Accordingly, there is provided a nucleic acid molecule encoding the AAT polypeptide as defined herein.

There is also provided a vector comprising a nucleic acid sequence encoding the AAT polypeptide as defined herein.

In some embodiments, the nucleic acid sequence is linked to an expression control sequence suitable for expression in a host cell.

There is also provided a cell comprising a nucleic acid as defined herein. In some embodiments, the cell comprises a vector as defined herein. In some embodiments, the cell is a mammalian cell or a bacterial cell. In some embodiments, the cell is a DH5α, BL21 (DE3) pLysS, SG13009 or Rosetta Blue DE3 cell.

In another aspect, there is provided a method of producing an AAT polypeptide as defined herein, comprising:
a. transfecting a host cell with a nucleic acid sequence encoding the AAT polypeptide as defined herein;
b. culturing the transfected host cell in a cell culture media and expressing the AAT polypeptide, and
c. recovering the AAT polypeptide from the cell culture media.

Specific examples of methods for producing AAT polypeptides according to the present disclosure are provided in the examples.

Pharmaceutical Compositions

Whilst in some embodiments, the AAT polypeptide of the present disclosure may if desired be administered by itself, typically it is administered in the form of a pharmaceutical composition, containing the AAT polypeptide and a pharmaceutically acceptable excipient.

Accordingly, there is provided a pharmaceutical composition comprising the AAT polypeptide as defined herein and a pharmaceutically acceptable carrier.

Any suitable pharmaceutical composition may be utilised.

The pharmaceutical compositions may for example contain one or more pharmaceutically acceptable carriers, excipients, such as a solvent or diluent, a buffer, a pH adjusting agent, an antioxidant, and/or a tonicity modifier.

Pharmaceutically suitable compositions of AAT polypeptides can be prepared according to methods known to those skilled in the art (see Remington's Pharmaceutical Sciences, 18th edition, AR Gennaro, Ed., Mack Publishing Company (1990); Pharmaceutical Formution Development of Peptides and Proteins, S. Frokjaer and L. Hovgaard, Eds., Taylor & Francis—(2000); and Handbook of Pharmaceutical Excipients, 31d edition, A. Kibbe, Ed, Pharmaceutical Press (2000)). These formulations include, for example, powders, pastes, ointments, jellies, waxes, oils, lipids, lipid (cationic or anionic) containing vesicles (such as LIPOFECTIN™), semi-solid gels, and semi-solid mixtures. See also Powell et al. "Compendium of excipients for parenteral formulations" PDA (1998) J Pharm Sci Technol 52:238-311.

The AAT polypeptides of the present disclosure may for example be prepared in a pharmaceutical composition in the form of a solution, suspension, emulsion solid (e.g. powder).

In some embodiments, the pharmaceutical composition is in the form of a lyophilized powder. In some embodiments, the pharmaceutical composition is in the form of a micronised powder.

In some embodiments, the pharmaceutical composition is in the form of a powder for reconstitution.

In some embodiments, the pharmaceutical composition is in liquid form, e.g. in the form of a solution.

The AAT polypeptide can be administered by any suitable route, and a pharmaceutical composition formulated to facilitate delivery of the AAT polypeptide by that route may be utilised.

In some embodiments, the pharmaceutical composition is in the form of an injectable formulation, e.g. for intravenous injection. In some embodiments, the pharmaceutical composition is in the form of an inhalable formulation, e.g. a powder for inhalation, or a nebulised pharmaceutical composition. it may for example be in the form of a composition suitable for producing an aerosolised form of the AAT polypeptide.

In some embodiments, the pharmaceutical composition is in the form of a composition for infusion, a composition for subcutaneous injection, or a composition for intratumoral injection.

Pharmaceutical compositions may be prepared by known methods. For example, the pharmaceutical compositions may be prepared, e.g., by dissolving, dispersing, suspending or emulsifying the polypeptide or its salt described above in a sterile aqueous medium conventionally used for injections. As aqueous media, examples include saline, water for injection, Ringer's solution, dextrose solution, 1-10% human serum albumin, an isotonic solution containing glucose and other auxiliary agents, which may if desired be used in combination with an appropriate solubilizing agent such as an alcohol (e.g., ethanol), a polyalcohol (e.g., propylene glycol, polyethylene glycol), a nonionic surfactant, or similar.

If a solid formulation is used, a solid carrier and/or other excipients may for example be used.

The pharmaceutical compositions may be administered in a number of dosage forms including time released or slow-release compositions. The pharmaceutical compositions may for example be in the form of powders, tablets, pills, capsules, microparticles, injections (ampoules), dispersions or similar. Tablets, pills, capsules or similar may also for example contain one or more of: a binder such as gum or gelatin, excipients, a disintegrating agent, a sweetening agent, a flavouring agent, an additive such as maltose, dextran, sucrose, lactose, mannitol, trehalose, albumin, collagen, gelatin, albumin, a preservative such as sobric acid, ascorbic acid, alpha-tocopherol, a thickener, buffer, a lubricant and so on. The tablets, pills, capsules or similar may be coated with an enteric coating if desired.

If desired, the AAT polypeptide may be encapsulated prior to administration to the subject. The encapsulation step is intended to protect the AAT polypeptide from degradation, thus further retaining stability of the polypeptide and retaining biological activity. For example, the AAT polypeptide may be encapsulated in liposomes, or similar.

In some embodiments, the AAT polypeptide may be administered in combination with a further therapeutic agent. In some embodiments, the AAT polypeptide and the further therapeutic agent are contained in the same pharmaceutical composition. In other words, in some embodiments, the pharmaceutical composition comprising the AAT polypeptide and a pharmaceutically acceptable excipient also comprises a further therapeutic agent.

The AAT polypeptides of the present disclosure have good stability properties meaning that they can be stored for long periods of time and/or at high temperatures whilst retaining good activity properties.

In some embodiments, the pharmaceutical composition retains at least 80%, or at least 90%, or at least 95% of its initial neutrophil elastase inhibitory activity upon storage at 4° C. for a period of 3 months, or for a period of 6 months (for example using a neutrophil elastase inhibitory assay as described in the examples).

Therapeutic Applications of AAT Polypeptides

The AAT polypeptides of the present disclosure find use in various therapeutic applications, including preventing or treating AAT deficiency or diseases and disorders associated with AAT deficiency as well as a variety of anti-inflammatory effects particularly against neutrophils.

Accordingly, there is also provided an AAT polypeptide as defined herein, or a pharmaceutical composition comprising the AAT polypeptide, for use as a medicament, e.g. for use in therapy. There is also provided an AAT polypeptide as defined herein, or a pharmaceutical composition comprising the AAT polypeptide, for use in preventing or treating AAT deficiency, or a disease or disorder associated with AAT deficiency.

There is also provided a method of preventing or treating AAT deficiency, or a disease or disorder associated with AAT deficiency, in a subject, comprising administering an effective amount of an AAT polypeptide as defined herein, or a pharmaceutical composition as defined herein, to the subject.

There is also provided use of an AAT polypeptide as defined herein, for the manufacture of a medicament for preventing or treating AAT deficiency, or a disease or disorder associated with AAT deficiency.

As used herein, the term "treating" includes curing a disease or disorder, as well as alleviation of or reduction of symptoms associated with a disease or disorder or condition. The term treating also includes slowing the progression of a disease or disorder.

As used herein, the term "prevention" includes prophylaxis, and includes reducing the likelihood of contracting a disease or disorder or a symptom thereof.

The term "subject" encompasses mammals and non-mammals. Examples of mammals include, but are not limited to, any member of the Mammalian class: humans; non-human primates such as chimpanzees, and other apes and monkey species; farm animals such as cattle, horses, sheep, goats, swine; domestic animals such as rabbits, dogs, and cats; and laboratory animals including rodents, such as rats, mice and guinea pigs, and the like. Examples of non-mammals include, but are not limited to, birds, fish and the like.

In some embodiments, the subject is a mammal. In some embodiments, the subject is a human. In some embodiments, the subject is a non-human animal. In some embodiments, the subject is male. In some embodiments, the subject is female. In some embodiments, the subject is an adult subject. In some embodiments, the subject is a juvenile or child subject.

As used herein, the term "effective amount" refers to a sufficient amount of AAT polypeptide or pharmaceutical composition containing the same, which provides a desired therapeutic or preventative effect. The effect includes, but is not limited to, the reduction and/or alleviation of the causes, symptoms or changes in underlying physiological pathways that underlie the development of a disease or condition. The use of the term "effective amount" in some embodiments refers to a sufficient amount of AAT polypeptide that provides a clinically relevant change in disease status, presence or absence of symptoms, or medical condition.

The term "medicament" refers to a form of formulation, composition or preparation, including medical preparations, that is suitable for administration to a subject. The medicament may for example comprise one or more pharmaceutically acceptable excipients. It may for example comprise a further therapeutic agent.

The AAT polypeptides have been shown to have potent anti-inflammatory and therapeutic activity which find utility in the treatment or prevention of a number of diseases or conditions. In particular, the AAT polypeptides of the present disclosure have been shown to significantly reduce neutrophil extracellular traps (NETs) and/or macrophage extracellular traps (METs).

Examples of the present engineered AAT polypeptides have improved stability and protein folding properties compared with wild type AAT, whilst retaining beneficial activity, making them desirable for the treatment of various diseases and conditions. For example, the present AAT polypeptides may find used in the treatment of diseases or conditions where the pathogenesis of disease is related to increased formation of NETs and/or METs.

Additionally, the present AAT polypeptides may also find utility in the treatment of diseases or conditions related to an imbalance of pro-inflammatory cytokines or increased inflammation.

The present AAT polypeptides may also find utility in the treatment of diseases or conditions related to or associated with protease activity.

Accordingly, in some embodiments, the disease or disorder is an inflammatory disease, a respiratory disease, a cancer and/or a viral infection.

In some embodiments, the disease or disorder is selected from the group consisting of: sepsis, autoimmune disease (e.g. inflammatory arthritis, vasculitis), acute respiratory disease, emphysema, pulmonary fibrosis, chronic obstructive pulmonary disease (e.g. acute exacerbated chronic obstructive pulmonary diseases), asthma, emphysema, a respiratory disease associated with air pollution, a cancer associated with protease activity (e.g. lung cancer, liver cancer), influenza A virus (IAV) and highly pathogenic avian influenza (HPAI).

Neutrophil-driven inflammation is specifically targeted by the action of AAT. In some embodiments, the disease or disorder is an inflammatory disease or disorder, and is a neutrophil-associated inflammatory disease or disorder. Further examples of disease or disorders include include cystic fibrosis (CF), bronchitis, liver disease, liver failure, rheumatoid arthritis, transplant rejection, graft versus host disease (GVHD), type 1 and 2 diabetes, and allergic airways disease.

The various conditions listed above may be characterised by a neutrophilic inflammatory response that is resistant to standard immunosuppression.

Experimental data has been generated to support the hypothesis that ROS/TLRs are involved in NET/MET trap formation. In particular, NTHi, cigarette smoke exposure (CSE), and influenza A virus all induce ROS production by phagocytes such as neutrophils and macrophages.

Thus, the present disclosure also relates to the administration of the present AAT polypeptides in order to reduce ROS/TLR activity. The present disclosure also relates to administration of the present AAT polypeptides in the treatment of a disease or disorder related to oxidative stress.

COPD is characterised by chronic inflammation that results in progressive lung damage. One of the main risk factors for the development of COPD is cigarette smoke exposure (CSE). However, once this inflammatory process is established, it tends to persist and progress, even after smoking cessation (potential causes of this effect include embedded smoking related substances, autoimmunity and infection). The main anti-inflammatory therapy used are glucocorticosteroids (GCS), which are only partially effective and have extensive side-effects.

The excessive production of proteases by lung innate immune cells (e.g. macrophages and neutrophils) and/or deficiency of inhibitors (e.g. AAT) results in protease imbalance. This imbalance usually occurs when there are relatively low levels of lung antiproteases and is a primary mechanism for the development of emphysema. The most important proteases include neutrophil elastase (NE) and macrophage metalloproteinases (MMP) 9 and 12, which are very pro-inflammatory and chemotactic.

Acute exacerbations of COPD (AECOPD) are most commonly triggered by bacterial and viral infections and typically increase lung inflammation. Even with the use of best available treatment, they frequently result in death and are a major cause of excess morbidity. AECOPD are the most common cause of hospitalisation in Australia. Nontypeable *Haemophilus influenzae* (NTHi) is the most common bacterium isolated in patients with COPD, particularly during exacerbations. Viral infections such as influenza A virus (IAV), are also a major cause of AECOPD.

Viral infections can also result in pronounced inflammatory responses in a subject, in particular in the lungs. These symptoms can be exacerbated by the subject's prior history such as being a smoker or having chronic respiratory disorders. Viral infections include IAV comprising the seasonal H1N1 and H3N2 strains and strains with pandemic potential, such as HPAI H5N1, H7N9, H9N2.

The AAT polypeptides are understood to reduce and dismantle NETs and METs, resulting in reduced inflammation and lead to improvement or cessation of symptoms related to inflammatory or protease imbalances. The present AAT polypeptides are also considered to have potent anti-inflammatory properties which can reduce circulating pro-inflammatory cytokine or chemokine levels in a subject. Exemplary cytokine or chemokines include IL-1β, IL-6, TNF-α and IFN-γ. The present AAT polypeptides are also considered to reduce leukocyte infiltrate in a subject, reducing their destructive pro-inflammatory effects in organs and tissue during chronic and acute disease.

The present AAT polypeptides find utility in the treatment of AAT deficiency, or a disease or disorder associated with AAT deficiency. One form of AAT deficiency is congenital AAT deficiency. Individuals have two copies of the AAT gene which allows the liver to produce AAT. However, in certain individuals, one copy of the AAT gene may comprise a mutation which affects that individual's ability to produce normal levels of AAT. In some individuals, the levels of AAT may be sufficiently low such that they manifest in on-going symptoms and health issues. AAT deficiency (AATD) is also referred to as genetic or inherited emphysema. AATD has been shown to cause chronic lung and liver disease.

There is currently no cure for AATD. Clinical management of AATD involves managing the symptoms by administration of antibiotics for lung infection such as influenza or pneumonia, or inhaled bronchodilators for relieving the symptoms of the emphysema such as breathlessness. AAT replacement or augmentation therapy can also be used in certain subjects. However, native AAT replacement or augmentation therapy is expensive given the instability of native AAT and the cost of production. Thus, many healthcare systems around the world do not cover the subject's costs of AAT replacement or augmentation therapy. The present AAT polypeptides have improved stability and higher yield over native AAT and therefore desirable.

The present AAT polypeptides are also considered to have utility in the treatment of cancer. Native AAT has been shown to inhibit angiogenesis and tumour growth. The AAT polypeptides may also be administered in combination with one or more other cancer treatments, such as surgery, radiotherapy, chemoradiotherapy, chemotherapy, treatment with cytotoxic agents, treatment with an antibody therapy, treatment with an antibody-drug conjugate, and/or cell therapies such as CAR-T cell therapies.

Surgery may be utilised to partially or fully remove the tumour by excision, debulking or cytoreductive surgery. Radiotherapy (or radiation therapy) utilises controlled doses of radiation to kill or damage cancer cells. Radiotherapy is frequently used in combination with chemotherapy, surgery or administration of other pharmaceutical compounds. When administered in combination with chemotherapy, the procedure is referred to as chemoradiation. Radiotherapy may be administered as external beam radiation therapy, or internal radiation therapy. Radiotherapy may also be administered systemically, through ingestion or injection of radioactive material.

In some embodiments, administration of the AAT polypeptide or pharmaceutical composition containing the same, achieves one or more of the following: reduced cytokine levels in a subject, reduced formation of extracellular traps in an organ of a subject, reduced protease activity, and reduced leukocyte infiltrate in an organ of a subject. These can broadly be considered as anti-neutrophil effects.

Any suitable administration route or dosage regimen may be utilised for the AAT polypeptides. For example, they may be administered intravenously, or by inhalation. In some embodiments, the AAT polypeptides are administered by inhalation, e.g. in nebulised form.

Any suitable dosing regimen of the AAT polypeptide may be utilised. For example, it may be administered once daily, twice daily, three times daily, four times daily, or as needed. It may for example be administered once per two days, once per three days, once per four days, once per five days, once per six days, weekly, once every 2 weeks, once every three weeks, once every four weeks, monthly, or at any other suitable dosing interval.

Any suitable dosage amount of the AAT polypeptide may be administered. For example an amount of AAT polypeptide in the range of from 0.001 mg to 1 g AAT polypeptide/kg bodyweight of the subject may be administered, or from 0.01 mg to 250 mg/kg, or from 0.01 mg to 50 mg/kg, or from 0.01 mg to 10 mg/kg, or from 0.01 mg to 1 mg/kg, or from 0.1 mg to 250 mg/kg, or from 0.1 mg to 50 mg/kg, or from 0.1 mg to 10 mg/kg, or from 0.1 mg to 1 mg/kg, or from 1 mg to 250 mg/kg, or from 1 mg to 50 mg/kg, or from 1 mg to 10 mg/kg, or up to 1 g/kg, or up to 250 mg/kg, or up to 50 mg/kg, or up to 10 mg/kg, or up to 5 mg/kg, or up to 1 mg/kg, or up to 0.5 mg/kg, or up to 0.1 mg/kg.

Whilst in some embodiments, the AAT polypeptide of the present disclosure may be administered as a sole therapeutic agent, in other embodiments it may be administered together with one or more further therapeutic agents.

Thus, in some embodiments, the AAT polypeptide, or pharmaceutical composition, is administered in combination with a further therapeutic agent.

The AAT polypeptide and the further therapeutic agent may be administered according to any dosage regimen which is suitable for treating or preventing the relevant disease or disorder. For example, the AAT polypeptide and the further therapeutic agent may be administered simultaneously (e.g. the AAT polypeptide and the further therapeutic agent may be administered in the same composition, or via different compositions administered at the same time), sequentially (e.g. one medicine is administered first, followed by the other) or separately (e.g. different medicaments may be administered at different times and/or on different days).

Examples of further therapeutic agents include agents for treatment of an inflammatory disease, a respiratory disease, a cancer, and/or a viral infection. In some embodiments, the further therapeutic agent is a therapeutic agent for treatment of a disease or disorder selected from the group consisting of: sepsis, autoimmune disease (e.g. inflammatory arthritis, vasculitis), acute respiratory disease, emphysema, pulmonary fibrosis, chronic obstructive pulmonary disease (e.g. acute exacerbated chronic obstructive pulmonary diseases), asthma, emphysema, a respiratory disease associated with air pollution, a cancer associated with protease activity (e.g. lung cancer, liver cancer), influenza A virus (IAV) and highly pathogenic avian influenza (HPAI).

Examples of further therapeutic agents include steroidal active agents, an NSAID, an anti-viral agent, an anti-fibrotic agent, and an anti-cancer agent.

Also provided herein is a kit comprising a) an AAT polypeptide according to the present disclosure; and b) a further therapeutic agent.

Also provided herein is a kit comprising a) a first pharmaceutical composition comprising an AAT polypeptide according to the present disclosure and a pharmaceutically acceptable carrier and/or excipient; and b) a second pharmaceutical composition comprising a further therapeutic agents and a pharmaceutically accetypable carrier and/or excipient.

The present disclosure is further illustrated by the following non-limiting examples.

EXAMPLES

Materials and Methods

Determination of AAT Polypeptide Inhibitory Activity
  Assay buffer: 50 mM Tris-HCL, 150 mM NaCl, 0.2% (v/v) PEG 8000, pH 7.4
  Proteases: Trypsin (1 mM HCl), HNE (50 mM sodium acetate, 150 mM NaCl, pH 5.5)
  Chromogenic substrate for trypsin: Na-Benzyol-L-arginine 4-nitroanilide hydrochloride (in DMSO)
  Chromogenic substrate for HNE: N-Methoxysuccinyl-Ala-Ala-Pro-Val p-nitroanilide (in DMSO)
  BMG FLUOstar Optima plate reader (405 nm)
Stoichiometry of Inhibition (SI)
Protocol:
  The stoichiometry of inhibition (SI) of each AAT polypeptide against protease was performed as previously described (Horvath et al). Different concentrations of AAT polypeptide were incubated with a constant concentration of protease (producing a range of 0-2:1 ratios) at 37° C. for 30 minutes in assay buffer to allow an AAT polypeptide: protease complex to form. The residual protease activity was measured for 1 hour with the addition of a target substrate (200 µM), using an Optima plate reader set at 405 nm. The change in absorbance from addition of substrate to the final reading after 1 hour was plotted as the percentage of active protease against the serpin: protease ratio. The data was normalized, with full protease activity (0:1 AAT polypeptide: protease) at 100%, and fit with a linear regression, where the interaction with the X-axis determining the SI.
Refolding and Determining the Stoichiometry of Inhibition
  Unfolding buffer: 6M GndHCl, 50 mM Tris-HCl, 150 mM NaCl pH 8.0
  Refolding buffer: 50 mM Tris-HCl, 150 mM NaCl pH 8.0
Protocol:
  AAT polypeptides were unfolded in unfolding buffer, consisting of 6M GndHCl, for 2 hours before refolding by dilution for another 2 hours. Any aggregate formed was pelleted by centrifugation (desktop centrifuge, 16,000×g for 5 minutes at 4° C.) and refolded sample dialysed against the refolding buffer to remove remaining GndHCl. The SI was performed as stated above.
AAT Polypeptide:Protease Complex SDS-PAGE gels
  10% SDS-PAGE gel
  6× Laemmli SDS loading dye Protocol:
  Different concentrations of AAT polypeptides to a constant concentration of protease (producing a 1:1 and 2:1 ratio) was incubated at 37° C. for 30 minutes to allow for a AAT polypeptide: protease complex to form. This reaction was stopped after 30 minutes with the addition of 6× reducing sample buffer and quenching the samples on ice. The samples were subjected to SDS-PAGE, using a 10% acrylamide gel, as stated above. The gel was stained with Commassie Blue stain and destained to observe any SDS-stable AAT polypeptide: protease complex formation.
Biophysical Analysis of AAT Polypeptides
Circular Dichroism (CD)
  Protein buffer: 1×Phosphate-buffered saline (1×PBS) (136 mM NaCl, 2.7 mM KCl, 10 mM $Na_2HPO_4$, 1.8 mM $KH_2PO_4$, pH 7.4)
  All circular dichroism techniques were performed on a Jasco J-815 circular dichroism spectrometer at a protein concentration of 0.2 mg/ml in 1×PBS, pH 7.4, using a path-length of 0.1 cm in a quartz cell.
Spectral Scan
  The observation of AAT polypeptide secondary structure was performed with Far-UV spectra (195-250 nm), scanning 100 nm/min. The concentration of AAT polypeptides was 0.2 mg/ml and the temperature held constant at 20° C.
Thermal Denaturation
  Thermal denaturation was performed with an increase in temperature from 25° C.-100° C. (unless otherwise stated), at a rate of 1° C./min, recording the change in signal at 222 nm. The AAT polypeptides remained at a concentration of 0.2 mg/ml. The sample was the cooled from 100° C. to 25° C. to observe if any thermal refolding occurred. The midpoint of transition ($T_m$) was obtained by fitting the data with a Boltzmann sigmoidal curve for both the melting and reverse melting/cooling denaturation experiments.
  For AAT polypeptides that did not undergo an unfolding transition from heating to 100° C., 2M GndHCl was added to aid in the unfolding. The sample with 2M GndHCl was again subjected to an increase in temperature from 25° C.-100° C. to determine the midpoint of transition.
Determining the Thermodynamic Properties Using Thermal Melts
  The thermodynamic properties of the AAT polypeptides were determined using the unfolding transition slope of the thermal melts. First, the ellipticity signal was normalized, producing a Y-axis of 'Fraction of unfolded' against temperature. The 'fraction of unfolded' when then converted into Keq using the following equation:

$$K_{eq} = \frac{f_u}{1 - f_u}$$

where $f_u$ is the fraction of unfolded protein. $K_{eq}$ was then converted into log $K_{eq}$. The temperature was converted into kelvin (° C.+273.15), then transformed into 1/temperature (K). Next, the log $K_{eq}$ was plotted against the corresponding 1/Temperature (K) to produce a van't Hoff analysis (John et al; Greenfield et al; Matthews et al). The resulting plot was fitted to a linear equation, with the Y-intercept producing the change in entropy, ΔS, using the gas constant, R (8.314 J/K/mol) and the following equation:

$$\frac{\Delta S}{R}$$

The change in enthalpy, ΔH, was calculated using the slope of the line and the gas constant, R, and the equation:

$$\frac{-\Delta H}{R}$$

The Gibbs free energy determined by thermal denaturation was calculated at room temperature (25° C.) using the Gibbs free energy equation:

$$\Delta G = \Delta H - T\Delta S$$

The change in Gibbs free energy (ΔΔG) between the WT and exemplary AAT polypeptides was calculated using the equation:

$$\Delta\Delta G = \Delta G_{WT} - \Delta G_{Grafts}$$

Analysis of Protein Refold by Gel Filtration
AKTA FPLC (GE Healthcare)
Superdex 200 increase 10/300 GL (GE Healthcare)
Protein/refolding buffer: 1×Tris-buffered saline (1×TBS) (150 mM NaCl, 25 mM Tris-HCL, pH 7.4)
Unfolding buffer: 8M GndHCl (in 1×TBS pH 7.4)
Protocol:
Analysis of refold was performed by comparing the absorbance peak (at 280 nm) of native and refolded protein using a Superdex 200 10/300 column at a final concentration of 2 µM. For refolding, the AAT polypeptides were unfolded in 5M GndHCl for 1.5 hours, then refolded by diluting the sample 10 times with refolding buffer until the final concentration of protein was 2 µM. The refolded sample was centrifuged to remove any aggregate and a total volume of 500 µl loaded onto the column. The yield was analysed by comparing the peak absorbance between native and refolded AAT polypeptides, normalizing the refolded peak against the top absorbance for wtAAT (where top absorbance of native protein is 100%).
Bis-ANS Unfolding
Cary Eclipse Fluorescence spectrophotomer (Agilent Technologies)
Native buffer: 1×Phosphate-buffered saline (1×PBS)
8M GndHCl (in 1×PBS, pH 7.4)
4,4'-Dianilino-1,1'-Binaphthyl-5,5'-Disulfonic Acid, Diphosphate salt (Bis-ANS) Protocol:
Bis-ANS unfolding experiment was performed in a similar manner to equilibrium unfolding, but in the presence of Bis-ANS. The protein sample (2 µM concentration) was incubated for at least 3 hours in different concentrations of GndHCl (ranging from 0-6M) and a 5-molar excess of Bis-ANS (final concentration of 10 µM). Reading of Bis-ANS fluorescence was obtained from a 1 cm pathlength cuvette with the excitation wavelength was 390 nm and emission detected from 400-700 nm (5 nm slits for both excitation and emission wavelengths). The peak fluorescence was plotted against the corresponding GndHCl concentration to analyse the chemical unfolding intermediate.

Validation experiments are expressed generally as mean and standard error of the mean (or median) and standard parametric/non parametric analysis has been used as appropriate.

Effect of AAT Polypeptides in Primary Human Cells (In Vitro)

Methods have been developed to study extracellular traps an inflammation in vitro and in vivo, see for example (King et al, PLoS One 2015; 10: e0120371; King et al, Sci Rep 2017; 7; 12128; Dousha et al, J Vis Exp 2021; King et al, ERJ Open Res, 2021, 7.

In King et al, ERJ Open Res, wild type AAT (wtAAT) was derived by column isolation from human serum. Neutrophils from peripheral blood or lung macrophages from bronchoscopy were infected with bacteria (NTHi) or influenza to induce extracellular trap with protease co-expression.

Bronchoalveolar (BAL) macrophages and paired blood samples for neutrophils were obtained from subjects having a bronchoscopy as part of standard clinical care. Non-smoking subjects were chosen without detectable lung disease who are being investigated for a chronic cough.

Human BAL macrophages and blood neutrophils (isolated from peripheral blood by centrifugation) on coverslips were infected (alongside uninfected controls) with a range of IAV strains in 24 well plates in culture medium with $10^5$ cells per well.

The following parameters were measured:
Expression of METs/NETs:
These were analysed using confocal microscopy with multiple methods: 1) extracellular chromatin with co-expression of proteases/histone/PAD2/4, and 2) the % of cells with enlarged nucleus with extracellular chromatin, 3) % of extracellular DNA staining for SYTOX and 4) and indirectly by the presence of extracellular DNA and using staining to confirm cellular viability using eFluor/Capase-3. The expression of traps will be analysed using defined software including IMARIS and Fuji Image J.
NE Activity:
Measured in neutrophils in periods starting from every 30 minutes to up to 4 hrs using a standard chromogenic assay).
Generation of Animal Model:
Mice were infected intranasally with IAV (1000 PFU of H3N2 for mild disease and 50 PFU of H1N1 for severe disease) or uninfected as control. In initial experiments mice were infected on the same day as IAV infection. However to mimic clinical practice subsequent detailed experiments one day after infection, mice were treated (Rx) with nebulised medications delivered intranasally on a daily basis with recombinant AAT: Mice were culled at days 4 and 11 to cover the spectrum of inflammatory changes. The peak inflammatory response typically occurs at day 3 post infection.
Effects of Storage on AAT Polypeptides Tests were performed on human neutrophils collected from healthy donors, and neutrophils seeded at 100,000 neutrophils per well in a 96 well plate. With the exception of the control group, all samples were inoculated with 10MOI of H1N1 (Brazil 78) influenza (+/−treatments), and incubated at 37° C. for one hour, after which the NE substrate was added, and cells further incubated at 37° C. for another hour. Reading was taken at 405 nm with a background reading at 550 nm.
Treatment Groups:
wtAAT from human plasma (R/T)—removed directly from −20° C. storage and stored at room temperature for up to 3 days.
uAAT (~2 weeks)—stored at 4° C. for 2 weeks
uAAT (~5 months)—stored at 4° C. for approximately 5 months.

To prepare the dose response curve, the effect of a range of different concentrations of recombinant AAT were tested against 0.5 ug of porcine neutrophil elastase (Sigma) and activity assessed using the same NE substrate and absorbance settings as described above).

Example 1: Preparation of AAT Polypeptides

The amino acid sequences of recombinant AAT polypeptides sAAT (SEQ ID NOs: 3 and 4) and uAAT (SEQ ID NOs: 5 and 6), of wildtype human AAT (SEQ ID NO: 1), and of the sequence from wildtype human AAT upon which the AAT polypeptides of the present disclosure are based (SEQ ID NO. 2), are provided in FIG. 1.

Wildtype human AAT was either purified from human plasma or made in a CHO or *E. coli* cell system.

Recombinant AAT polypeptides sAAT (SEQ ID NO: 3) and uAAT (SEQ ID NO: 5) were prepared as described below.

Bacterial Cell Lines

TABLE 1

A list of bacterial cell lines used to generate AAT polypeptides.

| Cell line | Genotype | Reference |
|---|---|---|
| DH5α | F– endA1 hsdR17 ($r_K^-$, $m_K^+$) supE44 thi-1 λ– recA1 gyrA96 relA1 deoR Δ(lacZYA-argF) U169 φ80lacZΔM15 | Grant et al |
| BL21 (DE3) pLysS | F–, ompT, $hsdS_B$ ($r_B^-$, $m_B^-$), dcm, gal, λ(DE3), pLysS, $Cm^r$ | Davanloo et al; Studier et al |
| SG13009 (Qiagen) | F–, $Nal^s$, $Str^s$, $Rif^s$, Thi–, Lac–, $Ara^+$, $Gal^+$, Mtl–, $RecA^+$ $Uvr^+$, $Lon^+$, $Km^r$ | Gottesman |
| Rosetta Blue DE3 | endA1, hsdR17 (rK12–mK12+), supE44, thi-1, recA1, gyrA96, relA1, lacF'[proA + B + acIqZΔM15::Tn109tetR)] ($DE_3$)pLysSRARE (CmR) | Novagen |

Transformation of DNA Into *E. Coli* Cells
Vectors

The vectors used to express recombinant wtAAT were pLIC-His and pQE-31 (Qiagen). Gene sequences for two exemplary alpha-1 anti-trypsin AAT polypeptides—sAAT and uAAT—were synthesized and cloned into the pQE-31 vector by Genscript (USA).

TABLE 2

A list of DNA vectors used to generate AAT polypeptides.

| DNA vector | | Transformed into: | Reference |
|---|---|---|---|
| pLIC-His | T7 promotor, ampicillin resistance, N-terminal 6xHis-tag | DH5α (storage) BL21 (DE3) pLysS (expression) | Levina et al; Cabrita et al |
| pQE-31 | T5 promotor, ampicillin resistance, N-terminal 6xHis-tag | DH5α (storage) SG13009 (expression) | Pearce et al; Qiagen |

Buffers:
  LB media: Yeast extract (5 g/L), peptone (tryptone, 10/L), NaCl (10 g/L)
  LB Agar: Yeast extract (5 g/L), peptone (tryptone, 10/L), NaCl (10 g/L), 1.5% agar
  Antibiotics: Ampicillin (100 mg/ml), Chloramphenicol (34 mg/ml) and Kanamycin (50 mg/ml).
Protocol:
  20 µl of competent cells was thawed, mixed with 1 µl of DNA and incubated on ice for 30 min. The competent cells were heat shocked at 42° C. for 45 seconds, followed by incubating on ice for 2 minutes. 100 µl of LB media was added to the cells, and cells recovered at 37° C. for 1 hour. The cells were plated onto LB agar (with appropriate antibiotics) and incubated overnight at 37° C.
Protein Expression
Buffers:
  2×YT media: Yeast extract (10 g/L), peptone (tryptone, 16 g/L), NaCl (5 g/L)
  2×YT agar: Yeast extract (10 g/L), peptone (tryptone, 16 g/L), NaCl (5 g/L), agar (1.5%)
  Antibiotics: Ampicillin (100 mg/ml), Chloramphenicol (34 mg/ml), Kanamycin (50 mg/ml) and tetracycline (12.5 mg/ml)
  Isopropyl B-D-thiogalactoside (IPTG): 1M
Protocol:
  A single colony from a transformation (as per the protocol above), inoculated an overnight culture of 10 ml 2×YT media (with appropriate antibiotics) and incubated at 37° C. overnight with constant shaking. This overnight culture inoculated 1 litre of 2×YT, then incubated at 37° C. with shaking until the cells reached an $OD_{600}$ of 0.6. Protein expression was induced with IPTG to a final concentration of 1 mM, and cells left to express protein for a 4 hours at 37° C. After the designated protein expression timeframe, the cells were harvested by centrifugation (4,000×g for 15 minutes at 4° C.) and cell pellets stored at –20° C.
Protein Purification Wildtype α1-antitrypsin (wtAAT), sAAT and uAAT were expressed both solubly and insolubly in *E. coli*, depending on type of the vector used for protein expression. wtAAT in the pQE-31 vector expressed in the soluble fraction/bacterial cytoplasm (Pearce et al), while AAT expressed in the pLIC-His vector was expressed insolubly in the inclusion bodies. sAAT and uAAT expressed into inclusion bodies, despite the DNA sequence cloned into pQE-31 vector.
Soluble Expressed Protein:
  Cell lysis buffer: 25 mM $NaH_2PO_4$, 500 mM NaCl, 1 mM β-ME, 10 mM Imidazole, pH 8.0
  Nickel-NTA (Ni-NTA) Affinity chromatography (native conditions):
    Loose Nickel-NTA resin (Qiagen)
    Ni-NTA wash buffer: 25 mM $NaH_2PO_4$, 150 mM NaCl, 1 mM β-ME, 10 mM Imidazole, pH 8.0
    Ni-NTA elution buffer: 25 mM $NaH_2PO_4$, 150 mM NaCl, 1 mM β-ME, 250 mM Imidazole, pH 8.0
Ion-Exchange Chromatography:
  AKTA FPLC (GE Healthcare)
  HiTrap Q FF anion chromatography column (GE Healthcare)

Dilution buffer: 50 mM Tris-HCl pH 8.0
Anion buffer A: 50 mM Tris-HCl, 50 mM NaCl, 1 mM EDTA, pH 8.0
Anion buffer B: 50 mM Tris-HCl, 1M NaCl, 1 mM EDTA, pH 8.0

Protocol:

The cell pellets containing soluble AAT were re-suspended in cell lysis buffer and incubated on ice for 20 minutes. Cells were disrupted by sonication on ice (6× 25 seconds on/35 seconds off) followed by centrifugation at 48,000×g for 20 minutes (4° C.) to pallet cellular debris. The soluble fraction was loaded onto pre-equilibrated loose Ni-NTA resin and incubated at 4° C. for 1 hour to allow batch binding to occur. Any protein that did not bind was eluted and collected, while loose binding protein was eluted with Ni-NTA wash buffer. Soluble AAT was eluted with Ni-NTA elution buffer into 1 ml fractions. The fractions that contained protein (as detected by 1:10 protein: Bradford reagent assay), were pooled and diluted with dilution buffer at a 1:1 ratio. The diluted sample was loaded onto a pre-equilibrated HiTrap Q FF anion exchange chromatography column. Ion-exchange chromatography separates the different conformations that serpins can adopt (i.e. separates active native from inactive latent and aggregate conformations). Any protein that did not bind was collected, and native AAT was eluted with an increasing sodium chloride (NaCl) concentration. Fractions that contained protein were run on an SDS-PAGE to ensure purity and tested against trypsin for inhibitory activity. Pure, active protein was either snap frozen and stored at −80° C. for long term storage or at 4° C. for use.

Insoluble Expressed Protein:
Cell lysis buffer: 50 mM $NaH_2PO_4$, 300 mM NaCl, 10 mM Imidazole pH 8.0
Unfolding inclusion body buffer: 8M Urea, 50 mM $NaH_2PO_4$, 300 mM NaCl, 10 mM Imidazole, 10 mM β-ME, pH 8.0
Nickel-NTA (Ni-NTA) Affinity chromatography (denaturing conditions):
Loose Nickel-NTA resin (Qiagen)
Ni-NTA wash buffer: 8M Urea, 50 mM $NaH_2PO_4$, 300 mM NaCl, 10 mM Imidazole, 10 mM β-ME, pH 8.0
Ni-NTA elution buffer: 8M Urea, 50 mM $NaH_2PO_4$, 300 mM NaCl, 250 mM Imidazole, 10 mM β-ME, pH 8.0
Refolding buffer: 50 mM Tris-HCl, 50 mM NaCl, 5 mM DTT, pH 8.0

Ion-Exchange Chromatography:
AKTA FPLC (GE Healthcare)
HiTrap Q FF anion chromatography column (GE Healthcare)
Anion buffer A: 50 mM Tris-HCl, 50 mM NaCl, 1 mM EDTA pH 8.0
Anion buffer B: 50 mM Tris-HCl, 1M NaCl, 1 mM EDTA pH 8.0

Protocol:

The cell pellets that contained insoluble AAT polypeptides (AAT expressed into inclusion bodies) were resuspended in cell lysis buffer and incubated on ice for 20 minutes. Cells were disrupted by sonication on ice (30 seconds on/off) and inclusion bodies harvested by centrifugation (48,000×g for 20 minutes at 4° C.). As the protein has a 6×His-tag, an inclusion body preparation was not necessary. Instead, Nickel-NTA (Ni-NTA) affinity chromatography was performed under denaturing conditions to partly purify AAT polypeptides from the inclusion body. The AAT polypeptides within the inclusion body were resuspended in unfolding inclusion body buffer by constant stirring with a magnetic stirrer for 2 hours at room temperature (approximately 21° C.). Any protein that was not resuspended was pelleted by centrifugation (35,000×g for 20 minutes at 4° C.). The soluble was filtered through 0.8 μm filter, loaded onto pre-equilibrated loose Ni-NTA resin and left to batch bind for 1 hour at 4° C. with rocking. Any protein that did not bind was collected, while loosely bound protein was eluted with Ni-NTA wash. α1-AT was batch eluted with Ni-NTA elution buffer. To ensure protein was present in the eluted sample, a 1:10 protein: Bradford reagent assay was performed.

The eluted AAT polypeptides were refolded by 1:200 dilution into refold buffer. The refold buffer contains DTT to reduce the cysteine residues and prevent disulphide-driven aggregation to occur. The refold was left to occur overnight at 4° C. with constant stirring to minimize concentration-dependent aggregation. Any aggregation that occurred was removed through filtering the refold buffer through 0.22 μm filter before loading the refold onto a pre-equilibrated HiTrap Q FF anion chromatography column. Any protein that did not bind was collected. Protein detected in the fractions were run on an SDS-PAGE to check for purity and tested against trypsin for inhibitory activity. Pure, active AAT polypeptides were pooled, and either snap frozen and stored at −80° C. for long term storage or at 4° C. for use.

Protein Buffer Exchange
AKTA FPLC (GE Healthcare)
HiTrap Desalting column (GE Healthcare)

Protocol:

To buffer exchange all proteins into a specific buffer, a HiTrap desalting column was used. The column was pre-equilibrated with the buffer of interest, and protein was loaded onto the HiTrap desalting column through the AKTA FPLC at a 1 ml volume. The fractions containing protein were pooled and stored at 4° C. for use.

Determination of Protein Concentration

The concentration of each protein sample was performed using a NanoDrop ND-1000 spectrophotometer (Thermo Scientific), measuring the absorbance at $A_{280}$. The extinction coefficient of each protein was included when measuring the A280, calculated by ExPASy ProtParam online tool (https://web.expasy.org/protparam/).

Sodium Dodecyl Sulfate-Polyacrylamide Gel Electrophoresis (SDS-PAGE)

An SDS-PAGE gel was run at the end of each protein purification procedure to check the purity of the protein. The gel was subjected to Western Blot only during trial expressions to check if the protein of interest was in the soluble (cell cytoplasm) or insoluble (inclusion bodies) fraction of the bacterial cells.

Reagents:
37.5% (40%) acrylamide solution
4× Resolving buffer: 0.5M Tris-HCL, 0.4% (w/v) SDS, pH 6.8
4× Stacking buffer: 1.5M Tris-HCL, 0.4% (w/v) SDS, pH 8.8
$ddH_2O$
20% (w/v) APS
TEMED
1×SDS Running buffer: 25 mM Tris base, 192 mM glycine, 0.1% (w/v) SDS
6×Laemmli SDS sample loading dye: 375 mM Tris-HCl, 9% SDS, 50% glycerol, 60 mM DTT and 0.03% bromophenol blue Precision Plus Protein dual colour standards (Bio-Rad)
Staining solution: 50% (v/v) ddH$_2$O, 40% (v/v) Methanol, 10% (v/v) acetic acid, 0.1% (w/v) Commassie brilliant Blue G-250
Destaining solution: 50% (v/v) ddH$_2$O, 40% (v/v) Methanol, 10% (v/v) acetic acid
Bio-Rad Mini-PROTEAN Tetra System
SDS-PAGE gels were constructed with 10% resolving gel and 4% stacking gel. Each gel was constructed as below:

| Reagent | 10% Resolving gel | 4% Stacking gel |
|---|---|---|
| 37.5% (40%) acrylamide solution (ml) | 2.5 | 0.325 |
| 4x Resolving buffer (ml) | 1.87 | — |
| 4x Stacking buffer (ml) | — | 0.625 |
| ddH$_2$O (ml) | 2.62 | 1.57 |
| 20% APS (µl) | 25 | 12.5 |
| TEMED (µl) | 10 | 5 |

Protocol:

Each sample subjected to electrophoresis were diluted with 6× reducing sample dye and boiled at 90° C. for 5 minutes before loading into the stacking wells of the SDS-PAGE gel. The gel was run at 250V for 30 minutes, or when the dye front reached the bottom of the gel, whichever was first. The gel was either stained with Commassie Blue protein stain or subjected to Western Blot. If the gel was to be stained with Commassie Blue, Commassie Blue protein stain was added to the gel and left to incubate for 30 minutes while rocking (at room temperature). The stain was then removed and destain added until the background of the gel has destained.

Western Blot

Reagents:
  TBS-T: 1×Tris-buffered saline (150 mM NaCl, 25 mM Tris-HCl, pH 7.4), 0.1% (v/v) Tween 20
  Blocking buffer: TBS-T, 5% (w/v) powdered skim milk
  Transfer buffer: 25 mM Tris base, 190 mM glycine, 15% methanol
  Anti-His HRP-labelled mouse monoclonal IgG
  ECL western blot detection reagents (Amersham)
  Fuji medical X-ray film (Fujifilm)
Protocol:

After an SDS-PAGE gel was performed, the proteins were transferred onto a pre-methanol soaked PVDF membrane in transfer buffer using a Bio-Rad transfer system, with a 100V current for 1 hour. The membrane containing the transferred proteins was blocked with blocking buffer for 1.5 hours, followed by the removal of the blocking buffer and addition of anti-His HRP-labelled antibody in TBST (1:10,000) for another 1 hour. Following antibody binding, the PVDF membrane was washed 4 times for 3 minutes with TBST. The ECL western Blot reagents were mixed and added to the membrane and the membrane exposed to X-ray film for 30 seconds, 1 minute and 30 minutes in a light proof cassette. The film was developed by an X-ray developer.

Production of AAT Polypeptides by CHO Expression

A total of 3× Alpha1-Anti-Trypsin (AAT) protein variants were expressed in ExpiCHO cells and purified through IMAC affinity purification followed by TEV cleavage of the His tag, in the aim of performing glycan profiling.

Outline

Protein production of 3×AAT proteins by transient CHO expression
  DNA for protein (with N-terminal His tag) synthesised by ThermoFisher Geneart and cloned into mammalian expression vector (pcDNA3.4)
  Purification of sterile DNA
  Transient transfection of ExpiCHO cells at 0.5 L scale each
  Purification using IMAC followed by a desalting step and TEV cleavage Expression Vectors DNA synthesis was outsourced along with cloning into a mammalian expression vector. The sequence design and relevant biophysical properties of the proteins of interest are summarised in the Table below, and the sequences are shown in FIG. 1. A mammalian Ig-derived leader sequence was added to the sequence design, along with a 5' Kozak sequence. DNA synthesis, along with cloning into an expression vector (pcDNA 3.4 TOPO), and preparation of transfection-grade DNA was outsourced to Geneart. Codon optimisation for expression in *Cricetulus griseus* was applied. The plasmids were given the internal designation NBF6401, NBF6402 and NBF6403 for uAAT, sAAT and rAAT respectively. uAAT and sAAT are mutant recombinant AAT polypeptides in accordance with the present disclosure. rAAT is recombinant wild type AAT.

| NBF ID | Protein name | MW (full length) | MW (after TEV) | Mass Exct. Coefficient (full length/after TEV) | Theoretical pI (full length/after TEV) |
|---|---|---|---|---|---|
| NBF6401 | uAAT | 45,977 Da | 44,359 Da | 0.521/0.506 | 5.50/5.26 |
| NBF6402 | sAAT | 46,073 Da | 44,455 Da | 0.520/0.505 | 5.50/5.26 |
| NBF6403 | rAAT | 46,029 Da | 44,411 Da | 0.466/0.449 | 5.62/5.37 |

DNA Preparation
Transformation

The AAT expression plasmids was transformed into chemically—competent *E. coli* cells (prepared in-house from Sigma Sig10 chemically-competent cells) via heat-shock treatment. Briefly, 100 ng of DNA was added to thawed competent cells and chilled on ice for 30 min. Cells were then heat-shocked at 42° C. for 45 sec prior to incubation on ice for 2 min. Luria Bertani medium (250 µL) was subsequently added and cells incubated at 37° C. for 1 hr to allow for recovery. The culture was then transferred to a flask containing 400 mL LB medium supplemented with 100 µg/L Ampicillin and grown overnight in a shaking incubator at 37° C., 200 rpm.

DNA Extraction and Purification

Plasmid DNA was purified using NucleoBond XtraMidi Kit (Macherey-Nagel Cat. 740410.100, Lot: 21011007) as per manufacturer's instructions. DNA clean-up with 70% v/v ethanol (Merck Absolute Ethanol #1.00983.2511, Invitrogen UltraPure Distilled Water #10977-015, Lot: 2323159) was carried out under sterile conditions to allow plasmids to be transfection-ready. DNA yields and purity obtained from the extraction are shown in the Table below.

| Plasmid | Concentration (µg/µL) | Volume (µL) | 260/280 (acceptable range 1.8-2.0) | 260/320 (acceptable range 2.0-2.2) |
|---|---|---|---|---|
| NBF6401 (uAAT) | 1.506 | 679.5 | 1.92 | 2.28 |
| NBF6402 (sAAT) | 1.792 | 535.2 | 1.93 | 2.28 |
| NBF6403 (rAAT) | 1.655 | 599.7 | 1.92 | 2.19 |

Transient Transfection

ExpiCHO™ cells from Thermo Fisher Scientific were thawed and grown in ExpiCHO Expression Medium (Thermo Fisher Scientific #A29100-01, Lot: 2455144) as per manufacturer's recommendations in a 37° C. shaking incubator at 130 rpm with 81% relative humidity and 7.5% CO2.

For each AAT variant, 2× 211 mL starting volume of ExpiCHO culture was transfected with ExpiFectamine CHO reagent (Thermo Fisher Scientific #100033021, Lot: 2418917) as outlined in the table below. Cells were cultured in Erlenmeyer Flasks (Corning #431147). Cultures were fed with ExpiFectamine™ CHO Enhancer (Thermo Fisher Scientific #100033018, Lot: 2430255) and ExpiCHO Feed (Thermo Fisher Scientific #A29101-02, Lot: 2378107) 22 hr post-transfection, with final culture volumes totalling to approximately 2× 280 mL. Cultures were then maintained in a 32° C. shaking 10 incubator at 130 rpm with 81% relative humidity and 7.5% CO2. Cultures were harvested on Day 5 post-transfection via centrifugation. The supernatant was further clarified through a 0.22 µm PES sterile filter unit vacuum (Nalgene #567-0020, Lot: 1266567, Nalgene #595-4520, Lot: 1333032) and was stored at −80° C. until purification.

|  | Process Target | Result/Comment |
|---|---|---|
| Cell Line | ExpiCHO Cells | ExpiCHO Cells |
| Medium | ExpiCHO Expression Medium | ExpiCHO Expression Medium |
| Target culture volume | 500 mL (each variant) | 2 × 280 mL (each variant) |
| Cell density at transfection | 6 × 10$^6$ cells/mL, ≥95% viability | 6.2 × 10$^6$ cells/mL, ≥99.6% viability |
| Transfection conditions | Reagents per 750 mL transfection Plasmid DNA: 0.5-1.0 µg/mL ExpiFectamine ™ CHO reagent: 2400 µL. OptiPRO ™ SFM: 28 & 30 mL ExpiFectamine ™ CHO Enhancer: 4.5 mL ExpiCHO ™ Feed: 180 mL | Transfection condition for 3 × 750 mL 1. 3 × 170 µg DNA was diluted in 3 × 8.4 mL of cold OptiPRO ™ SFM. 2. 3 × 657 µL of ExpiFectamine CHO reagent was diluted in 3 × 7.8 mL OptiPRO ™ SFM. Diluted ExpiFectamine CHO reagent was added to diluted DNA and incubated at RT for 5 mins. 4. ExpiFectamine CHO reagent-DNA complex was added to the ExpiCHO culture. 5. Transfected cells were incubated in a 37° C. shaking incubator at 130 rpm with 82% relative humidity and 7.5% CO$_2$. 6. 3 × 1.3 mL ExpiFectamine CHO Enhancer and 3 × 50.6 mL ExpiCHO Feed was added to cell culture 23 hours post-transfection. 7. Cells were transferred to a 32° C. shaking incubator at 130 rpm with 81% relative humidity and 7.5% CO$_2$. |
| Viable cell density | Viable cell density at harvest | NBF6401 (uAAT): Avg. 8.4 × 10$^6$ cells/mL NBF6402 (sAAT): Avg. 7.9 × 10$^6$ cells/mL NBF6403 (rAAT): Avg. 8.3 × 10$^6$ cells/mL |
| Cell viability at harvest | Cell viability at harvest: >75% | NBF6401 (uAAT): Avg. 74.15% NBF6402 (sAAT): Avg. 75.8% NBF6403 (rAAT): Avg. 80.4% |

Purification

Immobilized Metal Affinity Chromatography (IMAC) Affinity

Initial purifications have been performed on only 30 mL of the 500 mL harvest. The remaining harvest is stored at −80° C. for future purification.

All purification steps took place at room temperature and were performed using an ÄKTA Pure 25 chromatography system (GE Healthcare) using a flow rate of 2 mL/min.

The cell culture harvests (30 mL for each AAT variant) were first filtered using a 0.22 µm bottle top filter (Thermo Scientific), then purified were purified using a 1xmL Ni Sepharose column (HisTrap Excel—Cytiva).

For each harvest, the column was cleaned and sanitized with 0.5 M NaOH with a contact time of 60 minutes prior to the purification then equilibrated with DPBS with 500 mM NaCl (salty PBS). The column was first equilibrated with 5CV of binding buffer (pH 7.4), then loaded with the filtered culture supernatant. The column was washed with 5CV of salty DPBS (supplemented with 25 mM imidazole) and the protein was eluted from the Ni-Sepaharose using a salty DPBS (supplemented with 500 mM imidazole). The eluate was frozen at −20° C. prior to the desalting step. The thawed material was buffer exchanged using a diafiltration via Spin filter step (Amicon Ultra 10 kDa (Merck, UFC 901024) into the final buffer 50 mM Tris (pH 8.0), 150 mM NaCl. A list of all the buffers used is shown in the table below.

| Buffer Solution and Line | Components |
|---|---|
| Sanitising buffer | 0.5M NaOH (60 minutes contact time) |
| Equilibration buffer | 1 × DPBS (supplemented to 500 mM NaCl) |
| Wash buffer | 1 × DPBS (supplemented to 500 mM NaCl and 25 mM imidazole) |
| Elution buffer | 1 × DPBS (supplemented to 500 mM NaCl and 500 mM imidazole) |
| Desalting buffer | 50 mM Trus (pH 8.0), 150 mM NaCl |

The protein concentration of the final product was determined by UV/VIS absorbance at 280 nm (Thermo scientific, NanoDrop 2000 UV-Vis Spectrophotometer).

TEV Cleavage

The N-terminal His-tag of each purified AAT protein was removed using TEV enzymatic cleavage (NEB P81125, Lot No. E2103001). Briefly, the purified proteins (each ~6.5 mL at ~1.7 mg/mL) was cleaved overnight using 0.4 U of enzyme per µg of protein for 18 hours at +4° C. with gentle stirring in the presence of 50 mM Tris (pH 7.5), 0.5 mM EDTA, 1 mM DTT and 150 mM NaCl. An initial small scale TEV cleavage was performed to optimize the enzyme conditions (incubation temperature and amount of enzyme) (data not shown).

The IMAC eluate (in high imidazole) was frozen during processing of the material.

For the large-scale, ~1 mg of each AAT variant was TEV cleaved. The reactions were then passed through an IMAC affinity column to capture the His-tagged TEV enzyme and allow the untagged AAT material to be collected in the flowthrough (chromatograms not shown). The efficiency of the cleavage and the structural integrity of the purified material was verified by SDS-PAGE (stain free, Anti-His Western blot) and SE-UPLC. The final protein details including protein concentration, final volume and yield are recorded in the Table below.

| Sample | Cell culture Supernatant volume | IMAC affinity capture yield | Reverse IMAC Elution volume | Cleaved final product concentration | Final yield (mg) |
|---|---|---|---|---|---|
| uAAT | 30 mL | 10.5 mg | 1.0 mL | 0.75 mg/mL | 0.75 mg |
| sAAT | 30 mL | 10.8 mg | 0.6 mL | 0.92 mg/mL | 0.55 mg |
| rAAT | 30 mL | 8.3 mg | 0.7 mL | 0.92 mg/mL | 0.64 mg |

Analysis of In-Process Samples

SDS-PAGE analysis was performed under reducing conditions only, using 4-15% Mini-PROTEANR TGX Stain-Free Protein Gels (Biorad, Catalog No.: 4568095), ran at 200V for 35 minutes. A total of 5 µL of protein ladder was loaded to assess correct separation (Biorad Precision Plus unstained, Catalog No.: 1610363).

The same SDS-PAGE gel was subsequently transferred onto a PVDF membranes and blocked overnight at 4° C. with PBS-T (1×PBS supplemented with 0.05% Tween-20 and 2% skim milk). The membrane was then washed three times in PBS-T for 15 minutes and subsequently probed with Anti-His-HRP conjugate antibody (Miltenyi Biotec, Catalog No.: 130-092-785), at a dilution of 1:10,000 for 1.5 hour at room temperature. Finally, the membrane was washed three times in PBS-T for 15 minutes and analysed using the Novex chemiluminescent substrate kit (ThermoFisher, Catalog No.: WP20005). The membrane was then imaged using the Bio-Rad Chemi-Doc™ XRS+ imaging system.

Summary

A total of three AAT variants were successfully expressed in ExpiCHO cells with yields of ~300 mg/L (yields estimated post IMAC affinity capture). The N-terminal His tag was fully available for TEV cleavage and successfully removed for the 3 variants.

Example 2—Effect of Wild Type AAT

The effect of wtAAT on neutrophil elastase activity was assessed.

Nebulised wtAAT was administered to mice infected with IAV to measure the influence on lung inflammation. This reduced lung white cell numbers and lung weight (FIG. 2).

In addition levels of wtAAT in the airways of children with severe lung inflammation (such as cystic fibrosis) were found to be approximately $10^4$ times lower than in the blood. Therefore severe lung neutrophilic inflammation overwhelms the amount of blood circulation derived AAT in the lung, Therefore administering wtAAT by inhalation may provide a higher/appropriate dose to the site of disease/inflammation.

Example 3—Design of AAT Polypeptides

Engineering Stability Into AAT

Various clusters of amino acids that were hypothesized to contribute to thermostability were identified through determining the X-ray crystallography structure. These amino acids were found to contribute to the thermostability through improved packing in the hydrophobic core, the addition of favourable interactions throughout various regions or increased number of salt bridges. To improve the biophysical properties of wtAAT, each amino acid cluster or mutation was grafted onto wtAAT. All clusters were modelled to ensure all incoming amino acids fit and did not produce any unfavourable interactions. A total of eight grafts were produced, with a varying number of mutated amino acids; from two to six residues (FIGS. 3a and 3b, Table 3). Below is information of each graft, clustered based on the amino acid position:

Hydrophobic Core:
  T43S: introduction of three polar, uncharged side chains to create favourable polar and non-polar interactions. Present on Helix-A and Helix-B
  F35: contrary to the name, phenylalanine 35 was not mutated. Present on β-sheet A facing towards the hydrophobic core, three residues surrounding residue 35 were mutated. Two involved a decrease in side chains, while 1 has an increase in size chain size. This improves the packing against β-sheet A.

B/C Barrel:
  B/C barrel: Removal of two charged residues on Helix-H, facing into the B/C barrel, and a decrease in a side chain on β-sheet B facing towards Helix-H. This is to improve the hydrophobic packing within this region.
  Helix-H: An addition of six residues between Helix-H and β-sheet B, four of which include the addition of a charged residue. This creates a coordinated salt bridge network to stabilise the native structure. The remaining two residues involve either an increase (valine to phenylalanine) or decrease (phenylalanine to alanine) in side chain size. A combination of all mutations improves the residue packing, providing further stabilization (along with the salt bridge network).
  Citrate-binding: Two mutations were introduced in the B/C barrel, one on β-sheet B and another on β-sheet C. These mutations are in the region where citrate binds and stabilizes the native state of α1-AT through binding into a surface pocket. Introducing the two mutations, both of which contain a larger side chain, fill this surface pocket, stabilizing the native state.
  β-sheet C stapling: The addition of two charged residues on strands 2 and 3 of β-sheet C (s2C and s3C) creates a salt bridge, rigidifying and stabilizing β-sheet C.

Functional Regions:
  Breach: based at the top of β-sheet A and base of the RCL, five mutations were introduced to increase the salt bridge network already present. The additional salt bridges will prevent β-sheet A from opening up as easily as in wtAAT, stabilizing the native conformation.
  Helix-F: Laying in front of β-sheet A, three mutations introduced to improve the packing between Helix-F and β-sheet A, through the increase of 1 side chain and a decrease of the other two. This will rigidify the helix, possibly preventing easy shifting when β-sheet A opens.

TABLE 3

A list of the mutations introduced for each graft

| Graft | Mutations (positions based on SEQ ID No. 2) |
|---|---|
| Breach | S276K, T278E, T323E, D325N, K327E |
| B/C barrel | F237I, F259W, E263L |
| β-sheet C stapling | L208K, S269E |
| Citrate-binding | N212Y, L225E |
| F35 | L275F, I324V, M358I |
| Helix-F | G99A, Y144W, Y171A |
| Helix-H | L216D, K218E, V348F, F350A, N351D |
| T43S | L14N, A42S, T43S |

Improving AAT Thermostability

The aim for grafting regions onto wtAAT was to increase the thermostability of the native state, while not affecting AAT function. As a reference point, native AAT exhibits a $T_m$ of 60° C. To pinpoint the regions that are important in improving thermostability, each of the 8 grafts, including the latent grafts, underwent circular dichroism thermal melts (Table 4). Each sample was heated from 25-95° C. and cooled back down to 25° C. Out of the six natively folded grafts, three grafts improved the thermostability of AAT (Breach and Helix-F grafts). The F35 graft undergoes two unfolding transitions, an initial unfolding transition at 65° C., and a second transition that continues until 95° C.

TABLE 4

The thermodynamics of each graft in comparison to wtAAT.

| Graft | $T_m$ (° C.) | ΔTm (° C.) | $\Delta G^{(unfold)}$ (kcal/mol) | $\Delta\Delta G^{(unfold)}$ kcal/mol |
|---|---|---|---|---|
| wtAAT | 60 ± 2.26 | — | 8.79 ± 0.85 | — |
| Breach | 67.38 ± 0.34 | 7.38 ± 1.92 | 10.33 ± 0.279 | −1.54 ± 0.58 |
| B/C Barrel | 57.51 ± 0.39 | −2.49 ± 1.86 | 6.27 ± 0.26 | 2.52 ± 0.59 |
| Citrate | 58.11 ± 0.17 | −1.88 ± 2.1 | 4.672 ± 0.98 | 4.12 ± 0.12 |
| Helix-F | 62.08 ± 0.14 | 2.08 ± 2.11 | 12.86 ± 0.94 | −4.06 ± 0.8 |
| F35 | 65.48 ± 0.766 | 5.49 ± 1.49 | — | — |
| T43S | 56.96 ± 1.45 | −3.03 ± 0.8 | 8.007 ± 0.415 | 0.719 ± 0.444 |

Using the thermal denaturation curves to calculate the stability, 3 grafts are more stable than wtAAT.

An increase in thermostability is correlated with an increase in thermodynamic stability[271]. The thermodynamic stability of each graft was estimated using the thermal denaturation curves and van't Hoff analysis, and compared to wtAAT. The thermodynamics of each graft is suggestive, providing a rough estimate of how stable each graft is in comparison to wtAAT. Using the thermal denaturation curves, the Breach and Helix-F are suggested to be more thermodynamically stable than wtAAT (−1.54±0.58 and −4.06±0.8, respectively). Due to the nature of its folding transition, the thermodynamic stability of the F35 graft could not be calculated.

Increasing the Thermostability did not Significantly Compromise Function

To ensure increasing the thermostability did not compromise its function, the inhibitory activity of the three most thermostable grafts (Breach, Helix-F and F35) was tested against AAT's target protease human neutrophil elastase (HNE) through a stoichiometry of inhibition (SI) assay. The stoichiometry of inhibition calculates the number moles of AAT polypeptide it takes to inhibit one mole of protease. AAT has a stoichiometry of inhibition (SI) of 1:1 against HNE. The stoichiometry of inhibition of the Breach and F35 grafts are identical to that of wtAAT, while the Helix-F has an increased SI (Table 5).

TABLE 5

The stoichiometry of inhibition of the three thermostable grafts.

| Graft | SI against HNE (n = 3) |
|---|---|
| wtAAT | 1.0 ± 0.1 (Levina et al) |
| Breach | 1.09 ± 0.07 |
| F35 | 1.11 ± 0.05 |
| Helix-F | 1.35 ± 0.16 |

All three grafts did not significantly affect the inhibitory function, compared to wtAAT.

The Thermostable Grafts Yield More Monomeric Protein Post-Refold

AAT folds through at least one aggregation prone intermediate, which also increases the propensity to aggregate upon refolding (Kwon et al). As it is difficult to calculate and compare the amount of monomeric protein refolded during protein purification (due to inconsistent weight of bacterial cells), the most accurate way to determine the yield of monomeric AAT post-refold is by starting with a known protein concentration. Each protein was unfolded in 5M guanidine hydrochloride (GndHCl) for 2 hours, followed by refolding by dilution (1:10 dilution) until the final protein concentration was 2 μM. wtAAT largely aggregates upon refolding, yielding 11% of monomeric protein. The yield of each of the three thermostable grafts was higher than that of wtAAT. The F35 graft yields the most monomeric protein, followed by the Breach and lastly the Helix-F graft.

The Folding Intermediate is Populated at a Higher Denaturant Concentration wtAAT folds through at least one aggregation-prone folding intermediate. Introducing mutations onto the peptide could possibly affect the folding intermediate, thus affecting the folding pathway. An extrinsic fluorescent dye, Bis-ANS, binds to the hydrophobic regions of the protein and allows the detection of the folding intermediates. AAT's folding intermediate is populated over a wide denaturant concentration. The three thermostable grafts also have an intermediate that is populated over a wide concentration and have a fluorescent profile similar to wtAAT. The difference, however, is the concentration in which the fluorescence increases. For each of the three grafts, the maximum fluorescent intensity occurs at a higher denaturant concentration than wtAAT. Therefore, each graft requires a slightly higher chemical denaturation concentration to promote unfolding.

Discussion

Each of the grafts that increased the thermostability of α1-AT (AAT) are in regions that play a role in folding. The F35 graft introduced mutations in the hydrophobic core, which is the first region to fold, while mutations in the breach region lead to misfolding and polymerization during folding (as observed in the Z mutation). During folding, the Helix-F is highly disrupted and undergoes a conformational change during unfolding and polymerization. During α1-AT's folding pathway, the folding intermediate is aggregation-prone, which can lead to aggregation during refolding. The yield post-refold for each of the grafts increased in comparison to wtAAT, with the F35 graft increasing the yield the most, while the Helix-F graft only slightly increased yield. This is plausible, as the F35 graft was modelled with improved packing and introduction of favourable interactions, possibly increasing the folding rate and decreasing the time the aggregation-prone intermediate is present. Furthermore, the increase in yield of the Breach graft could be a result of the increase number of salt bridges forcing the closure of β-sheet A during the last stages of folding.

The modelled improved packing in the Helix-F graft seems not contribute to the yield post-refold as much as the other two grafts. This suggests that this graft, and Helix-F does not contribute to a decrease in aggregation propensity during folding. Since the three highly thermostable grafts provide for desirable interactions within wtAAT, the three grafts were next used to design further combined grafts.

Example 4—Design of Further AAT Polypeptides and Their Biophysical Analysis

Grafting different amino acid clusters onto AAT produced three grafts that contained an increase in thermostability and monomeric protein post-refold, all while not substantially affecting the inhibitory function against HNE (only Helix-F graft has a slightly higher SI). Therefore, it was hypothesized that combining these three grafts would produce an additive thermostability effect. The combined graft, termed "sAAT" was designed, synthesized and cloned in the same way as the single grafts. The sequence of sAAT is shown in FIG. 1.

Recombinant expression of the sAAT graft produced a majority of the protein in the insoluble fraction (as with all the previous grafts), with a small amount remaining soluble. The sAAT graft successfully refolded into the active, native conformation.

The addition of the three thermostable grafts onto sAAT produced an additive midpoint of thermal denaturation of sAAT, which was determined by circular dichroism thermal melts (25 to 95° C., followed by cooling). The sAAT graft exhibited a $T_m$ with an unfolding midpoint of 73.4° C. (FIG. 4B). There have been many attempts to increase the thermal stability of AAT, but the sAAT polypeptide has the highest thermostability (as calculated by circular dichroism thermal denaturation curves) of an engineered native AAT to date. sAAT did not reversibly refold upon cooling from 95° C., instead, produced precipitate similarly to wtAAT (FIG. 4A).

To observe if it is possible to increase the thermostability even further, further mutations were introduced to the sAAT graft to produce a further engineered AAT polypeptide, uAAT. The mutations were as follows:

| Additional mutations in uAAT (positions based on SEQ ID No. 2) |
|---|
| F35L |
| T43A |
| T52A |
| A54G |
| S365A |
| K371R |

The amino acid sequence of uAAT is provided in FIG. 1.

Unlike sAAT which expressed predominantly in the insoluble fraction, uAAT expresses solubly during recombinant expression.

The thermodynamic stability was estimated using the van't Hoff analysis in an identical manner to above. The thermodynamic stability of sAAT graft was 8.66 kcal mol$^{-1}$ above WT (Table 6).

TABLE 6

The thermodynamic stability analysis of the sAAT and uAAT polypeptides.

| AAT polypeptide | $T_m$ (° C.) | $\Delta T_m$ (° C.) | $\Delta G^{(unfold)}$ (kcal/mol) | $\Delta\Delta G^{(unfold)}$ (kcal/mol) |
|---|---|---|---|---|
| wtAAT | 60 ± 2.26 | — | 8.79 ± 0.85 | — |
| sAAT | 73.4 ± 0.9 | 13.38 ± 1.36 | 17.46 ± 3.27 | −8.66 ± 2.41 |
| uAAT | 87 | 27 | ND | — |

The sAAT polypeptide has an increased midpoint of thermal denaturation (Tm) and Gibbs free energy (ΔG) compared to wtAAT.

As the stability of the sAAT polypeptide was increased, there is a possibility of a stability-function trade-off. To ensure the sAAT polypeptide remained as an active inhibitor against HNE, the SI was calculated, with sAAT inhibiting HNE with an SI of 1.28±0.1 (FIG. 4C & Table 7). This SI was only slightly higher than that of wtAAT, but was not significantly higher.

Experiments subjecting uAAT to thermal denaturation revealed a large increase in thermostability over wtAAT (Table 7). This is a highly thermostable AAT.

TABLE 7

The SI of the molecules calculated against HNE.

| Protein | SI against HNE (n = 3) |
|---|---|
| wtAAT | 1.0 ± 0.1[75] |
| sAAT | 1.28 ± 0.1 |
| uAAT | ND |

Each of the exemplary AAT polypeptides have an increase in yield post-refold. Under the same conditions, the sAAT graft produced a yield of 63%, confirming the hypothesis (FIG. 4D). The folding intermediate was not affected, with the intermediate present over a wide concentration. The largest difference in studying the folding intermediate is the denaturant concentration of the peak fluorescence (peak fluorescence at approximately 2M GndHCl), compared to wtAAT and each thermostable graft (FIG. 4E). Therefore, a higher denaturant concentration is required to unfold the sAAT polypeptide without affecting the intermediate.

Enhanced Thermostability Increased Yield of Monomeric Protein Post Refold

The post-refold yield of the presently described AAT polypeptides indicates a relationship between thermostability and refold yield. sAAT and uAAT yielded significantly more monomeric protein post-refold than wtAAT. uAAT also follows this relationship. The yield obtained post-refold was a maximum of 70%. uAAT is the more thermostable of the two, and yields the most monomeric protein, strongly emphasising a relationship between thermostability and refold yield.

TABLE 8

Refolding yields

| Graft | Refold Yield (%) |
|---|---|
| wtAAT | 11 |
| sAAT | 63 |
| uAAT | 70 |

Example 5—Anti-Inflammatory and Immunomodulatory Effect of AAT Polypeptides

Recombinant AATs according to the present disclosure (sAAT, uAAT, rAAT) were produced. In vitro experiments in neutrophils stimulated with IAV (influenza A virus) to produce NETs showed in a variety of stimulation models that the AAT polypeptides according to the present disclosure reduced NE expression (FIG. 5).

Further experiments were conducted using sAAT. Recombinant AAT (sAAT) was produced by a bacterial expression system. sAAT reduced NE activity using a standard curve of increasing doses (FIG. 6). The engineered AAT polypeptide of the present disclosure was observed both in vitro and in vivo to be highly effective in reducing NE activity at different concentrations.

In vitro experiments in stimulated neutrophils to produce NETs showed in a variety of stimulation models (NTHi (nontypeable *Haemophilus influenzae* (NTHi) infection), IAV (influenza A virus), black carbon (for air pollution), silica (for pulmonary fibrosis) and cigarette smoke extract (CSE) that the sAAT reduced NE expression (FIGS. 7-10).

Example 6—Anti-Viral Effects of AAT Polypeptides

A recombinant AAT polypeptide according to the present disclosure was shown to reduce infection of, human epithelial cells (FIG. 11). Epithelial cells were infected with IAV and with rAAT and a plaque assay was used to determine intracellular infection.

Human lung epithelial cell lines were infected with IAV for 1 hour with and without rAAT (sAAT), before being lysed and the supernatant cultured for the levels of IAV using a plaque assay (n=6). The sAAT reduced the infection of the lung epithelial cells (FIG. 17).

Example 7—AAT Polypeptides Retain Activity on Storage

A key factor that differentiates recombinant AAT polypeptides according to the present disclosure from wtAAT is its stability. This is particularly important for nebulisation.

The neutrophil NET assay described above was used again.

The effect of sAAT (that had been in the fridge for 2 weeks and 5 months; then left at room temperature (RT) was compared to fresh wtAAT (referred to as eluted AAT or eAAT) at RT. Both sAAT stored samples were effective in reducing NE activity and were better than fresh wtAAT. The results are shown in FIG. 12. The figure shows influenza A infection (IAV) of neutrophils which induces increased neutrophil elastase (NE) activity. This is markedly reduced by both 2 week- and 5 month-old sAAT (stored in the fridge) and effect is more pronounced than blood plasma derived eluted AAT (wtAAT, referred to as eAAT) (stored in fridge for 2 days). This result demonstrates the stability of the AAT polypeptide of the present disclosure, which was still potent after 5 months in the fridge.

3 subtypes of recombinant AAT were produced by the National Biologics Facility at the University of Queensland. This allowed production of the recombinant AAT in much larger quantities than by a bacterial expression system using a Chinese hamster Ovarian (CHO) expression system. The 3 variants had a similar effect in reducing NE activity (FIG. 13). The effectiveness of the variants of recombinant AAT left at room temperature for a week to reduce NE activity was also assessed using the NET assay (FIG. 14) and standard curve (FIG. 15) and demonstrated effectiveness.

Nebulised recombinant AAT (sAAT) was obtained and its effectiveness in reducing NE activity was assessed using the NET assay (FIG. 16). This again demonstrates the stability of the recombinant AAT polypeptide according to the present disclosure.

In vivo experiments were performed to assess the effect on lung inflammation. Mice were infected with IAV. Mice were then given nebulised rAAT (sAAT) or untreated (as control) on a daily basis for 3 days. After this time the mice were culled. The weight and lung BAL cell count of each mouse was then measured. The sAAT reduced inflammation by decreasing both the lung white cell count (FIG. 18) and the lung weight (FIG. 19).

Subsequent more detailed experiments were done with mice that were infected with either seasonal or virulent IAV then administered the recombinant AAT on a daily basis one day after infection (to mimic clinical practice). Mice were administered the nebulised AAT for 5 days and culled at days 4 or 11 post infection. In both IAV infections the recombinant AAT had striking anti-inflammatory effects with: 1) decreased weight loss (FIG. 20), 2) decreased lung weight (FIG. 21), 3) decreased lung white cell count (FIG. 22) and 4) decreased lung neutrophil elastase (FIG. 23). Other preliminary results have demonstrated decreased lung cytokine expression (e.g., interleukin 6) and less inflammation on lung histology (including decreased lung oedema and area of the lung with changes of bronchopneumonia). Preliminary results have demonstrated some mild decrease in IAV load, but as AAT was administered one day after infection the primary effect was likely to be anti-inflammatory.

Finally, in order to increase the usefulness of the invention the recombinant AAT was lyophophilised (freeze dried) and then reconstituted and used in the in vitro NET assays described above. This results demonstrated that the lyophilised AAT remained highly effective in reducing NE activity in vitro (FIG. 24).

Summary

The above results demonstrate that the exemplary AAT polypeptides reduce inflammatory responses to a variety of prevalent disease-causing infections and atmospheric pollutants (such as cigarette smoke and air pollution). Further, the present engineered AAT polypeptides are highly stable and aggregation-resistant, which are both advantageous properties for administration via inhalation. Such an administration route is preferred to improve its potent anti-inflammatory effects. The stability of the present engineered AAT polypeptides also provide for benefits during distribution and storage of the AAT polypeptides, allowing for maintenance of its therapeutic effects for a prolonged period of time. The high protein stability of the AAT polypeptides of the present disclosure are also advantageous for particular routes of administration such as aerosol delivery.

Those skilled in the art will appreciate that the disclosure herein is susceptible to variations and modifications other than those specifically described. It is to be understood that the disclosure includes all such variations and modifications.

REFERENCES

Levina, V., Dai, W., Knaupp, A. S., Kaiserman, D., Pearce, M. C., Cabrita, L. D., Bird, P. I., and Bottomley, S. P. (2009) Expression, purification and characterization of recombinant Z α1-Antitrypsin—The most common cause of α1-Antitrypsin deficiency. *Protein Expr. Purif.* 68, 226-232.

Grant, S. G. N., Jesseet, J., Bloomt, F. R., and Hanahan, D. (1990) Differential plasmid rescue from transgenic mouse DNAs into *Escherichia coli* methylation-restriction mutants 87, 4645-4649.

Davanloo, P., Rosenberg, A. H., Dunn, J. J., and Studier, F. W. (1984) Cloning and expression of the gene for bacteriophage T7 RNA polymerase. *Proc. Natl. Acad. Sci.* 81, 2035-2039.

Studier, F. W., and Moffattf, B. A. (1986) Use of Bacteriophage T7 RNA Polymerase to Direct Selective High-level Expression of Cloned Genes 113-130.

Gottesman, S., Halpern, E., and Trisler, P. (1981) Role of sulA and sulB in Filamentation by Lon Mutants of *Escherichia coli* K-12 148, 265-273.

Cabrita, L. D., Dai, W., and Bottomley, S. P. (2006) A family of *E. coli* expression vectors for laboratory scale and high throughput soluble protein production. *BMC Biotechnol.* 6, 12.

Pearce, M. C., and Cabrita, L. D. (2011) Production of Recombinant Serpins in *Escherichia coli*, in *Methods in Enzymology* 1st ed., pp 13-28. Elsevier Inc.

Qiagen. (2003) The QIA expressionist Handbook, 5th Ed. *Diagen GmbH, Düsseldorf, Ger.* Bachman, J. (2013) Site-directed mutagenesis. *Methods Enzymol.* 1st ed. Elsevier Inc.

Horvath, A. J., Lu, B. G. C., Pike, R. N., and Bottomley, S. P. (2011) Methods to measure the kinetics of protease inhibition by serpins. *Methods Enzymol.* 1st ed. Elsevier Inc.

John, D. M., and Weeks, K. M. (2000) Van't Hoff enthalpies without baselines. *Protein Sci.* 9, 1416-1419.

Greenfield, N. J. (2009) Using circular dichroism collected as a function of temperature to determine the thermodynamics of protein unfolding and binding interactions. *Nat. Protoc.* 1, 2527-2535.

Matthews, B. W., Nicholson, H., and Becktel, W. J. (1987) Enhanced protein thermostability from site-directed mutations that decrease the entropy of unfolding. *Proc. Natl. Acad. Sci. U.S.A.* 84, 6663-7.

Seo, E. J., Lee, C., and Yu, M. H. (2002) Concerted regulation of inhibitory activity of α1-antitrypsin by the native strain distributed throughout the molecule. *J. Biol. Chem.* 277, 14216-14220.

Kwon, K. S., Lee, S., and Yu, M. H. (1995) Refolding of alpha 1-antitrypsin expressed as inclusion bodies in *Escherichia coli*: characterization of aggregation. *Biochim. Biophys. Acta* 1247, 179-84.

King PT, Sharma R, O'Sullivan K, Selemidis S, Lim S, Radhakrishna N, Lo C, Prasad J, Callaghan J, McLaughlin P, Farmer M, Steinfort D, Jennings B, Ngui J, Broughton BR, Thomas B, Essilfie AT, Hickey M, Holmes PW, Hansbro P, Bardin PG, Holdsworth SR. Nontypeable *Haemophilus influenzae* induces sustained lung oxidative stress and protease expression. *PLoS One* 2015; 10: e0120371.

King PT, Sharma R, O'Sullivan KM, Callaghan J, Dousha L, Thomas B, Ruwanpura S, Lim S, Farmer MW, Jennings BR, Finsterbusch M, Brooks G, Selemidis S, Anderson GP, Holdsworth SR, Bardin PG. Deoxyribonuclease 1 reduces pathogenic effects of cigarette smoke exposure in the lung. *Sci Rep* 2017; 7:12128.

Dousha L, Sharma R, Lim S, Ngui J, Buckle AM, King PT. Assessing Respiratory Immune Responses to *Haemophilus Influenzae*. *J Vis Exp* 2021.

King PT, Dousha L, Clarke N, Schaefer J, Carzino R, Sharma R, Wan KL, Anantharajah A, O'Sullivan K, Lu ZX, Holdsworth SR, Ranganathan S, Bardin PG, Armstrong DS. Phagocyte extracellular traps in children with neutrophilic airway inflammation. *ERJ Open Res* 2021; 7.

Janciauskiene S, Wrenger S, Immenschuh S, Olejnicka B, Greulich T, Welte T, Chorostowska-Wynimko J. The Multifaceted Effects of Alpha1-Antitrypsin on Neutrophil Functions. *Front Pharmacol* 2018; 9:341.

Bai X, Hippensteel J, Leavitt A, Maloney JP, Beckham D, Garcia C, Li Q, Freed BM, Ordway D, Sandhaus RA, Chan ED. Hypothesis: Alpha-1-antitrypsin is a promising treatment option for COVID-19. *Med Hypotheses* 2021; 146:110394.

The invention claimed is:

1. An alpha-1 antitrypsin (AAT) polypeptide, comprising:
an amino acid sequence having at least 90% sequence identity to SEQ ID NO: 2;
wherein the amino acid sequence includes one, two, or all of the following groups of amino acid substitutions from SEQ ID NO: 2:
S276K, T278E, T323E, D325N, and K327E;
L275F, I324V, and M358I; and
G99A, Y144W, and Y171A.

2. The AAT polypeptide of claim 1, wherein the amino acid sequence includes each of the following amino acid substitutions from SEQ ID NO: 2: G99A, Y144W, Y171A, L275F, S276K, T278E, T323E, I324V, D325N, K327E, and M358I.

3. The AAT polypeptide of claim 1, wherein the amino acid sequence includes 1 or more further amino acid substitutions from SEQ ID NO: 2 which are independently selected from the group consisting of: F35L, T43A, T52A, A54G, S365A, and K371R.

4. The AAT polypeptide of claim 3, wherein the amino acid sequence includes 2 or more, or 3 or more, or 4 or more, or 5 or more, or each of the following further amino acid substitutions from SEQ ID NO: 2: F35L, T43A, T52A, A54G, S365A, and/or K371R.

5. The AAT polypeptide of claim 1, wherein the amino acid sequence comprises at least 91%, at least 92%, at least 93%, at least 94% or at least 95% sequence identity to SEQ ID NO: 2.

6. The AAT polypeptide of claim 1, wherein the amino acid sequence comprises not more than 35, not more than 30, not more than 25, or not more than 20 amino acid modifications from SEQ ID NO:2.

7. The AAT polypeptide of claim 1, wherein the amino acid sequence comprises not more than 10, not more than 5, or no amino acid modifications from SEQ ID NO: 2, other than:
including one, two, or all of the following groups of amino acid substitutions from SEQ ID NO: 2:
S276K, T278E, T323E, D325N, and K327E;
L275F, I324V, and M358I; and
G99A, Y144W, and Y171A; and
optionally including 1 or more further amino acid substitutions from SEQ ID NO:
2 which are independently selected from the group consisting of F35L, T43A, T52A, A54G, S365A, and K371R.

8. The AAT polypeptide of claim 1, wherein the polypeptide comprises an additional N-terminal and/or C-terminal amino acid sequence.

9. The AAT polypeptide of claim 8 wherein, prior to the amino acid sequence, the AAT polypeptide comprises the N-terminal sequence MENLYFQGAAS (SEQ ID NO: 7) or MPSSVSWGILLLAGLCCLVPVSLAE-DPQGDAAQKTDTSHH (SEQ ID NO: 8).

10. The AAT polypeptide of claim 1 which comprises the amino acid sequence of SEQ ID NO: 3, SEQ ID NO: 4, SEQ ID NO: 5 or SEQ ID NO: 6.

11. The AAT polypeptide of claim 1, wherein the AAT polypeptide has improved thermal stability compared to wild-type human AAT.

12. The AAT polypeptide of claim 1, wherein the AAT polypeptide has improved re-fold yield compared to wild-type AAT.

13. The AAT polypeptide of claim 1, which comprises a modification selected from the group consisting of glycosylation, PEGylation, prenylation, acylation, biotinylation, phosphorylation, and conjugation to a lipid moiety.

14. The AAT polypeptide of claim 1, wherein the amino acid sequence comprises the following group of amino acid substitutions from SEQ ID NO: 2: S276K, T278E, T323E, D325N and K327E.

15. The AAT polypeptide of claim 1, wherein the amino acid sequence comprises the following group of amino acid substitutions from SEQ ID NO: 2: L275F, I324V and M358I.

16. The AAT polypeptide of claim 1, wherein the amino acid sequence comprises the following group of amino acid substitutions from SEQ ID NO: 2: G99A, Y144W and Y171A.

17. A pharmaceutical composition comprising:
the AAT polypeptide of claim 1; and
a pharmaceutically acceptable excipient.

18. A pharmaceutical composition as claimed in claim 17, wherein the pharmaceutical composition retains at least 80%, or at least 90%, or at least 95% of the initial neutrophil elastase inhibitory activity upon storage at 4° C. for a period of 3 months, or for a period of 6 months.

* * * * *

SEQUENCE LISTING

```
Sequence total quantity: 9
SEQ ID NO: 1            moltype = AA  length = 418
FEATURE                 Location/Qualifiers
source                  1..418
                        mol_type = protein
                        organism = synthetic construct
SEQUENCE: 1
MPSSVSWGIL LLAGLCCLVP VSLAEDPQGD AAQKTDTSHH DQDHPTFNKI TPNLAEFAFS   60
LYRQLAHQSN STNIFFSPVS IATAFAMLSL GTKADTHDEI LEGLNFNLTE IPEAQIHEGF  120
QELLRTLNQP DSQLQLTTGN GLFLSEGLKL VDKFLEDVKK LYHSEAFTVN FGDTEEAKKQ  180
INDYVEKGTQ GKIVDLVKEL DRDTVFALVN YIFFKGKWER PFEVKDTEEE DFHVDQVTTV  240
KVPMMKRLGM FNIQHCKKLS SWVLLMKYLG NATAIFFLPD EGKLQHLENE LTHDIITKFL  300
ENEDRRSASL HLPKLSITGT YDLKSVLGQL GITKVFSNGA DLSGVTEEAP LKLSKAVHKA  360
VLTIDEKGTE AAGAMFLEAI PMSIPPEVKF NKPFVFLMIE QNTKSPLFMG KVVNPTQK    418

SEQ ID NO: 2            moltype = AA  length = 378
```

```
FEATURE                 Location/Qualifiers
source                  1..378
                        mol_type = protein
                        organism = synthetic construct
VARIANT                 35
                        note = F35L
VARIANT                 43
                        note = T43A
VARIANT                 52
                        note = T52A
VARIANT                 54
                        note = A54G
VARIANT                 99
                        note = G99A
VARIANT                 144
                        note = Y144W
VARIANT                 171
                        note = Y171A
VARIANT                 275
                        note = L275F
VARIANT                 276
                        note = S276K
VARIANT                 278
                        note = T278E
VARIANT                 323
                        note = T323E
VARIANT                 324
                        note = I324V
VARIANT                 325
                        note = D325N
VARIANT                 327
                        note = K327E
VARIANT                 358
                        note = M358I
VARIANT                 365
                        note = S365A
VARIANT                 371
                        note = K371R
SEQUENCE: 2
DQDHPTFNKI  TPNLAEFAFS  LYRQLAHQSN  STNIFFSPVS  IATAFAMLSL  GTKADTHDEI   60
LEGLNFNLTE  IPEAQIHEGF  QELLRTLNQP  DSQLQLTTGN  GLFLSEGLKL  VDKFLEDVKK  120
LYHSEAFTVN  FGDTEEAKKQ  INDYVEKGTQ  GKIVDLVKEL  DRDTVFALVN  YIFFKGKWER  180
PFEVKDTEEE  DFHVDQVTTV  KVPMMKRLGM  FNIQHCKKLS  SWVLLMKYLG  NATAIFFLPD  240
EGKLQHLENE  LTHDIITKFL  ENEDRRSASL  HLPKLSITGT  YDLKSVLGQL  GITKVFSNGA  300
DLSGVTEEAP  LKLSKAVHKA  VLTIDEKGTE  AAGAMFLEAI  PMSIPPEVKF  NKPFVFLMIE  360
QNTKSPLFMG  KVVNPTQK                                                   378

SEQ ID NO: 3            moltype = AA  length = 389
FEATURE                 Location/Qualifiers
source                  1..389
                        mol_type = protein
                        organism = synthetic construct
REGION                  1..11
                        note = N-terminal E coli tag
SEQUENCE: 3
MENLYFQGAA  SDQDHPTFNK  ITPNLAEFAF  SLYRQLAHQS  NSTNIFFSPV  SIATAFAMLS   60
LGTKADTHDE  ILEGLNFNLT  EIPEAQIHEG  FQELLRTLNQ  PDSQLQLTTA  NGLFLSEGLK  120
LVDKFLEDVK  KLYHSEAFTV  NFGDTEEAKK  QINDWVEKGT  QGKIVDLVKE  LDRDTVFALV  180
NAIFFKGKWE  RPFEVKDTEE  EDFHVDQVTT  VKVPMMKRLG  MFNIQHCKKL  SSWVLLMKYL  240
GNATAIFFLP  DEGKLQHLEN  ELTHDIITKF  LENEDRRSAS  LHLPKFKIEG  TYDLKSVLGQ  300
LGITKVFSNG  ADLSGVTEEA  PLKLSKAVHK  AVLEVNEEGT  EAAGAMFLEA  IPMSIPPEVK  360
FNKPFVFLII  EQNTKSPLFM  GKVVNPTQK                                      389

SEQ ID NO: 4            moltype = AA  length = 418
FEATURE                 Location/Qualifiers
source                  1..418
                        mol_type = protein
                        organism = synthetic construct
REGION                  1..40
                        note = N-terminal CHO tag
SEQUENCE: 4
MPSSVSWGIL  LLAGLCCLVP  VSLAEDPQGD  AAQKTDTSHH  DQDHPTFNKI  TPNLAEFAFS   60
LYRQLAHQSN  STNIFFSPVS  IATAFAMLSL  GTKADTHDEI  LEGLNFNLTE  IPEAQIHEGF  120
QELLRTLNQP  DSQLQLTTAN  GLFLSEGLKL  VDKFLEDVKK  LYHSEAFTVN  FGDTEEAKKQ  180
INDWVEKGTQ  GKIVDLVKEL  DRDTVFALVN  AIFFKGKWER  PFEVKDTEEE  DFHVDQVTTV  240
KVPMMKRLGM  FNIQHCKKLS  SWVLLMKYLG  NATAIFFLPD  EGKLQHLENE  LTHDIITKFL  300
ENEDRRSASL  HLPKFKIEGT  YDLKSVLGQL  GITKVFSNGA  DLSGVTEEAP  LKLSKAVHKA  360
VLEVNEEGTE  AAGAMFLEAI  PMSIPPEVKF  NKPFVFLIIE  QNTKSPLFMG  KVVNPTQK    418
```

```
SEQ ID NO: 5              moltype = AA  length = 389
FEATURE                   Location/Qualifiers
source                    1..389
                          mol_type = protein
                          organism = synthetic construct
REGION                    1..11
                          note = N-terminal E coli tag
SEQUENCE: 5
MENLYFQGAA SDQDHPTFNK ITPNLAEFAF SLYRQLAHQS NSTNILFSPV SIAAAFAMLS    60
LGAKGDTHDE ILEGLNFNLT EIPEAQIHEG FQELLRTLNQ PDSQLQLTTA NGLFLSEGLK   120
LVDKFLEDVK KLYHSEAFTV NFGDTEEAKK QINDWVEKGT QGKIVDLVKE LDRDTVFALV   180
NAIFFKGKWE RPFEVKDTEE EDFHVDQVTT VKVPMMKRLG MFNIQHCKKL SSWVLLMKYL   240
GNATAIFFLP DEGKLQHLEN ELTHDIITKF LENEDRRSAS LHLPKFKIEG TYDLKSVLGQ   300
LGITKVFSNG ADLSGVTEEA PLKLSKAVHK AVLEVNEEGT EAAGAMFLEA IPMSIPPEVK   360
FNKPFVFLII EQNTKAPLFM GRVVNPTQK                                    389

SEQ ID NO: 6              moltype = AA  length = 418
FEATURE                   Location/Qualifiers
source                    1..418
                          mol_type = protein
                          organism = synthetic construct
REGION                    1..40
                          note = N-terminal CHO tag
SEQUENCE: 6
MPSSVSWGIL LLAGLCCLVP VSLAEDPQGD AAQKTDTSHH DQDHPTFNKI TPNLAEFAFS    60
LYRQLAHQSN STNILFSPVS IAAAFAMLSL GAKGDTHDEI LEGLNFNLTE IPEAQIHEGF   120
QELLRTLNQP DSQLQLTTAN GLFLSEGLKL VDKFLEDVKK LYHSEAFTVN FGDTEEAKKQ   180
INDWVEKGTQ GKIVDLVKEL DRDTVFALVN AIFFKGKWER PFEVKDTEEE DFHVDQVTTV   240
KVPMMKRLGM FNIQHCKKLS SWVLLMKYLG NATAIFFLPD EGKLQHLENE LTHDIITKFL   300
ENEDRRSASL HLPKFKIEGT YDLKSVLGQL GITKVFSNGA DLSGVTEEAP LKLSKAVHKA   360
VLEVNEEGTE AAGAMFLEAI PMSIPPEVKF NKPFVFLIIE QNTKAPLFMG RVVNPTQK    418

SEQ ID NO: 7              moltype = AA  length = 11
FEATURE                   Location/Qualifiers
source                    1..11
                          mol_type = protein
                          organism = synthetic construct
SEQUENCE: 7
MENLYFQGAA S                                                        11

SEQ ID NO: 8              moltype = AA  length = 40
FEATURE                   Location/Qualifiers
source                    1..40
                          mol_type = protein
                          organism = synthetic construct
SEQUENCE: 8
MPSSVSWGIL LLAGLCCLVP VSLAEDPQGD AAQKTDTSHH                          40

SEQ ID NO: 9              moltype = AA  length = 25
FEATURE                   Location/Qualifiers
source                    1..25
                          mol_type = protein
                          organism = synthetic construct
SEQUENCE: 9
MPSSVSWGIL LLAGLCCLVP VSLAE                                         25
```